US012594151B2

(12) United States Patent
Nikolskiy et al.

(10) Patent No.: US 12,594,151 B2
(45) Date of Patent: *Apr. 7, 2026

(54) PROCESSING CT SCAN OF DENTAL IMPRESSION

(71) Applicant: James R. Glidewell Dental Ceramics, Inc., Newport Beach, CA (US)

(72) Inventors: Sergey Nikolskiy, Coto de Caza, CA (US); Fedor Chelnokov, Khimki (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/649,448

(22) Filed: Apr. 29, 2024

(65) Prior Publication Data

US 2024/0277454 A1     Aug. 22, 2024

Related U.S. Application Data

(63) Continuation of application No. 18/069,473, filed on Dec. 21, 2022, now Pat. No. 11,998,422, which is a
(Continued)

(51) Int. Cl.
| | |
|---|---|
| *A61C 9/00* | (2006.01) |
| *A61C 13/00* | (2006.01) |
| *A61B 6/51* | (2024.01) |

(52) U.S. Cl.
CPC .......... *A61C 9/0053* (2013.01); *A61C 9/0006* (2013.01); *A61C 13/0004* (2013.01); *A61B 6/51* (2024.01)

(58) Field of Classification Search
CPC . A61C 9/0046; A61C 9/0053; A61C 13/0004; A61C 9/0006; A61B 6/5217;
(Continued)

(56) References Cited

U.S. PATENT DOCUMENTS

| | | | |
|---|---|---|---|
| 471,086 | A | 3/1892 | Raymond |
| 637,161 | A | 11/1899 | Ring |

(Continued)

FOREIGN PATENT DOCUMENTS

| | | |
|---|---|---|
| CN | 108024841 A | 5/2018 |
| CN | 108665533 A | 10/2018 |

(Continued)

OTHER PUBLICATIONS

Amberg et al., "Optimal Step Nonrigid ICP Algorithms for Surface Registration," Proceedings/CVPR, IEEE Computer Society Conference on Computer Vision and Pattern Recognition, Jun. 2007, 9 pages.
(Continued)

*Primary Examiner* — Congvan Tran
(74) *Attorney, Agent, or Firm* — Klarquist Sparkman, LLP

(57) ABSTRACT

A computer-implemented method and system of determining a material surface from a volumetric density file includes generating a density frequency distribution of a volumetric density file of a dental impression and determining an iso-value of density between air and a particular material in the density frequency distribution. A computer-implemented method and system of creating a digital model from a CT scan of a physical dental impression includes selecting an iso-value of density for a digital volumetric density file having one or more voxels, generating one or more digital surface points in virtual 3D space for each of one or more voxels, and selecting a subset of digital surface points from the one or more digital surface points. A computer-implemented method and system of optimizing a digital surface includes moving one or more digital surface points to satisfy a criteria of optimum digital surface selection.

15 Claims, 37 Drawing Sheets

Related U.S. Application Data continuation of application No. 16/451,315, filed on Jun. 25, 2019, now Pat. No. 11,534,271.

(58) Field of Classification Search
CPC ........... A61B 6/032; A61B 6/466; A61B 6/51; G06T 17/20; G06T 2210/56
See application file for complete search history.

(56) References Cited

U.S. PATENT DOCUMENTS

| | | | |
|---|---|---|---|
| D302,683 S | 8/1989 | Iwasaki et al. |
| 5,023,895 A | 6/1991 | McCroskey et al. |
| 5,270,827 A | 12/1993 | Kobayashi et al. |
| 5,368,478 A | 11/1994 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,605,459 A | 2/1997 | Kuroda et al. |
| D394,316 S | 5/1998 | Kodama et al. |
| 5,879,158 A | 3/1999 | Doyle et al. |
| 6,068,482 A | 5/2000 | Snow |
| 6,081,739 A | 6/2000 | Lemchen |
| 6,091,412 A | 7/2000 | Siminoff |
| 6,152,731 A | 11/2000 | Jordan et al. |
| 6,198,552 B1 | 3/2001 | Nagae |
| 6,217,334 B1 | 4/2001 | Hultgren |
| 6,227,850 B1 | 5/2001 | Chishti et al. |
| 6,244,861 B1 | 6/2001 | Andreiko et al. |
| 6,318,994 B1 | 11/2001 | Chisthi et al. |
| 6,322,359 B1 | 11/2001 | Jordan et al. |
| 6,350,120 B1 | 2/2002 | Sachdeva et al. |
| 6,386,867 B1 | 5/2002 | Durbin et al. |
| 6,386,878 B1 | 5/2002 | Pavlovskaia et al. |
| 6,406,292 B1 | 6/2002 | Chisthi et al. |
| 6,409,504 B1 | 6/2002 | Jones et al. |
| 6,450,807 B1 | 9/2002 | Chisthi et al. |
| 6,463,344 B1 | 10/2002 | Pavloskaia et al. |
| 6,512,994 B1 | 1/2003 | Sachdeva |
| 6,554,611 B2 | 4/2003 | Chisthi et al. |
| 6,582,225 B1 | 6/2003 | Bergesen |
| D476,658 S | 7/2003 | Adachi et al. |
| 6,602,070 B2 | 8/2003 | Miller et al. |
| 6,621,491 B1 | 9/2003 | Baumrind et al. |
| 6,632,089 B2 | 10/2003 | Rubbert et al. |
| 6,633,789 B1 | 10/2003 | Nikolskiy et al. |
| 6,648,640 B2 | 11/2003 | Rubbert et al. |
| 6,688,886 B2 | 2/2004 | Hughes et al. |
| 6,726,478 B1 | 4/2004 | Isiderio et al. |
| 6,767,208 B2 | 7/2004 | Kaza |
| 6,783,360 B2 | 8/2004 | Chishti |
| 7,013,191 B2 | 3/2006 | Rubbert et al. |
| 7,027,642 B2 | 4/2006 | Rubbert et al. |
| 7,029,275 B2 | 4/2006 | Rubbert et al. |
| 7,040,896 B2 | 5/2006 | Pavlovskaia et al. |
| 7,068,825 B2 | 6/2006 | Rubbert et al. |
| 7,080,979 B2 | 7/2006 | Rubbert et al. |
| 7,110,594 B2 | 9/2006 | Jones et al. |
| 7,134,874 B2 | 11/2006 | Chishti |
| 7,140,877 B2 | 11/2006 | Kaza |
| D533,555 S | 12/2006 | Odhe et al. |
| 7,156,655 B2 | 1/2007 | Sachdeva et al. |
| 7,234,937 B2 | 6/2007 | Sachdeva |
| 7,292,716 B2 | 11/2007 | Kim |
| 7,361,018 B2 | 4/2008 | Imgrund et al. |
| 7,361,020 B2 | 4/2008 | Abolfathi et al. |
| 7,373,286 B2 | 5/2008 | Nikolskiy et al. |
| D573,146 S | 7/2008 | Sukenari et al. |
| D580,962 S | 11/2008 | Sukenari et al. |
| 7,476,100 B2 | 1/2009 | Kuo |
| 7,545,372 B2 | 6/2009 | Kopelman et al. |
| 7,609,875 B2 | 10/2009 | Liu |
| D612,851 S | 3/2010 | Maruyama et al. |
| 7,717,708 B2 | 5/2010 | Sachdeva et al. |
| 7,740,476 B2 | 6/2010 | Rubbert et al. |
| 7,805,003 B1 | 9/2010 | Cohen et al. |

| | | | |
|---|---|---|---|
| 8,013,853 B1 | 9/2011 | Douglas et al. |
| 8,045,180 B2 | 10/2011 | Friemel |
| 8,075,306 B2 | 12/2011 | Kitching et al. |
| 8,229,180 B2 | 7/2012 | Baloch et al. |
| 8,308,481 B2 | 11/2012 | DiAngelo et al. |
| 8,332,061 B2 | 12/2012 | Baloch et al. |
| 8,342,843 B2 | 1/2013 | Perot et al. |
| 8,380,644 B2 | 2/2013 | Zouhar et al. |
| D678,383 S | 3/2013 | Park et al. |
| D714,940 S | 10/2014 | Kim |
| 8,855,375 B2 | 10/2014 | Macciola |
| 8,995,732 B2 | 3/2015 | Kaza et al. |
| 9,055,988 B2 | 6/2015 | Galgut et al. |
| 9,135,498 B2 | 9/2015 | Andreiko et al. |
| D742,010 S | 10/2015 | Metcalf |
| 9,421,074 B2 | 8/2016 | Sachdeva et al. |
| D776,818 S | 1/2017 | Metcalf |
| 9,626,462 B2 | 4/2017 | Somasundaram et al. |
| 9,629,698 B2 | 4/2017 | Lior et al. |
| 9,737,381 B2 | 8/2017 | Lee |
| 9,888,983 B2 | 2/2018 | Sachdeva et al. |
| 10,149,744 B2 | 12/2018 | Lior et al. |
| 10,624,717 B2 | 4/2020 | Wen |
| 10,945,812 B1 | 3/2021 | Raslambekov |
| 11,534,271 B2 | 12/2022 | Nikolskiy et al. |
| 11,540,906 B2 | 1/2023 | Nikolskiy et al. |
| 11,559,378 B2 | 1/2023 | Nikolskiy et al. |
| 11,622,843 B2 | 4/2023 | Nikolskiy et al. |
| 2001/0002310 A1 | 5/2001 | Chishti et al. |
| 2002/0006217 A1 | 1/2002 | Rubbert et al. |
| 2002/0028418 A1 | 3/2002 | Farag et al. |
| 2002/0141626 A1 | 10/2002 | Caspi |
| 2002/0150859 A1 | 10/2002 | Imgrund et al. |
| 2002/0180760 A1 | 12/2002 | Rubbert |
| 2003/0198377 A1 | 10/2003 | Ng |
| 2003/0198378 A1 | 10/2003 | Ng |
| 2003/0207227 A1 | 11/2003 | Abolfathi |
| 2003/0207235 A1 | 11/2003 | Van der Zel |
| 2003/0224314 A1 | 12/2003 | Bergersen |
| 2004/0072120 A1 | 4/2004 | Lauren |
| 2004/0146198 A1 | 7/2004 | Herley |
| 2004/0152036 A1 | 8/2004 | Abolfathi |
| 2004/0175671 A1 | 9/2004 | Jones et al. |
| 2004/0197728 A1 | 10/2004 | Abolfathi et al. |
| 2004/0214128 A1 | 10/2004 | Sachdeva et al. |
| 2005/0018901 A1 | 1/2005 | Kaufmann et al. |
| 2005/0019732 A1 | 1/2005 | Kaufmann et al. |
| 2005/0030368 A1 | 2/2005 | Morrison |
| 2005/0043837 A1 | 2/2005 | Rubbert et al. |
| 2005/0055118 A1 | 3/2005 | Nikolskiy et al. |
| 2005/0089213 A1 | 4/2005 | Geng |
| 2005/0089822 A1 | 4/2005 | Geng |
| 2005/0191593 A1 | 9/2005 | Knopp |
| 2005/0192835 A1 | 9/2005 | Kuo et al. |
| 2005/0208449 A1 | 9/2005 | Abolfathi et al. |
| 2005/0271996 A1 | 12/2005 | Sporbert et al. |
| 2006/0127859 A1 | 6/2006 | Wen |
| 2006/0147872 A1 | 7/2006 | Andreiko |
| 2006/0154198 A1 | 7/2006 | Durbin et al. |
| 2006/0173541 A1 | 8/2006 | Friel |
| 2006/0263739 A1 | 11/2006 | Sporbert et al. |
| 2006/0263741 A1 | 11/2006 | Imgrund et al. |
| 2006/0275736 A1 | 12/2006 | Wen et al. |
| 2007/0003900 A1 | 1/2007 | Miller |
| 2007/0031790 A1 | 2/2007 | Raby et al. |
| 2007/0031791 A1 | 2/2007 | Cinader et al. |
| 2007/0065768 A1 | 3/2007 | Naday |
| 2007/0128573 A1 | 6/2007 | Kuo |
| 2007/0128574 A1 | 6/2007 | Kuo et al. |
| 2007/0129991 A1 | 6/2007 | Kuo |
| 2007/0134613 A1 | 6/2007 | Kuo et al. |
| 2007/0141527 A1 | 6/2007 | Kuo et al. |
| 2007/0167784 A1 | 7/2007 | Shekhar et al. |
| 2007/0168152 A1 | 7/2007 | Matov et al. |
| 2007/0190481 A1 | 8/2007 | Schmitt |
| 2007/0207441 A1 | 9/2007 | Lauren |
| 2007/0238065 A1 | 10/2007 | Sherwood et al. |
| 2008/0020350 A1 | 1/2008 | Matov et al. |
| 2008/0048979 A1 | 2/2008 | Ruttenberg |

(56)  References Cited

U.S. PATENT DOCUMENTS

| | | |
|---|---|---|
| 2008/0057466 A1 | 3/2008 | Jordan et al. |
| 2008/0064008 A1 | 3/2008 | Schmitt |
| 2008/0176182 A1 | 7/2008 | Hultgren et al. |
| 2008/0182220 A1 | 7/2008 | Chishti et al. |
| 2008/0248443 A1 | 10/2008 | Chishti et al. |
| 2008/0261165 A1 | 10/2008 | Steingart et al. |
| 2008/0305458 A1 | 12/2008 | Lemchen |
| 2008/0311537 A1 | 12/2008 | Minagi et al. |
| 2009/0080746 A1 | 3/2009 | Xu et al. |
| 2009/0087817 A1 | 4/2009 | Jansen et al. |
| 2009/0162813 A1 | 6/2009 | Glor et al. |
| 2009/0220916 A1 | 9/2009 | Fisker et al. |
| 2009/0246726 A1 | 10/2009 | Chelnokov et al. |
| 2009/0248184 A1 | 10/2009 | Steingart et al. |
| 2009/0298017 A1 | 12/2009 | Boerjes et al. |
| 2009/0311647 A1 | 12/2009 | Fang et al. |
| 2009/0316966 A1 | 12/2009 | Marshall et al. |
| 2010/0009308 A1 | 1/2010 | Wen et al. |
| 2010/0100362 A1 | 4/2010 | Zouhar et al. |
| 2010/0105009 A1 | 4/2010 | Karkar et al. |
| 2010/0111386 A1 | 5/2010 | El-Baz |
| 2010/0138025 A1 | 6/2010 | Morton et al. |
| 2010/0145898 A1 | 6/2010 | Malfliet et al. |
| 2010/0151417 A1 | 6/2010 | Nilsson et al. |
| 2010/0217567 A1 | 8/2010 | Marshall |
| 2010/0260405 A1 | 10/2010 | Cinader, Jr. |
| 2010/0297572 A1 | 11/2010 | Kim |
| 2011/0004331 A1 | 1/2011 | Cinader, Jr. et al. |
| 2011/0045428 A1 | 2/2011 | Boltunov et al. |
| 2011/0059413 A1 | 3/2011 | Schutyser et al. |
| 2011/0060438 A1 | 3/2011 | Stoddard et al. |
| 2011/0090513 A1 | 4/2011 | Seidl et al. |
| 2011/0184762 A1 | 7/2011 | Chishti et al. |
| 2011/0206247 A1 | 8/2011 | Dachille et al. |
| 2011/0207072 A1 | 8/2011 | Schiemann |
| 2011/0244415 A1 | 10/2011 | Batesole |
| 2011/0268326 A1 | 11/2011 | Kuo et al. |
| 2011/0292047 A1 | 12/2011 | Chang et al. |
| 2012/0015316 A1 | 1/2012 | Sachdeva et al. |
| 2012/0065756 A1 | 3/2012 | Rubbert et al. |
| 2012/0088208 A1 | 4/2012 | Schulter et al. |
| 2012/0139142 A1 | 6/2012 | Van der Zel |
| 2012/0214121 A1 | 8/2012 | Greenberg |
| 2013/0172731 A1 | 7/2013 | Gole |
| 2013/0218531 A1 | 8/2013 | Deichmann et al. |
| 2013/0226534 A1 | 8/2013 | Fisker et al. |
| 2013/0325431 A1 | 12/2013 | See et al. |
| 2013/0329020 A1 | 12/2013 | Kriveshko et al. |
| 2013/0335417 A1 | 12/2013 | McQueston et al. |
| 2014/0003695 A1 | 1/2014 | Dean et al. |
| 2014/0055135 A1 | 2/2014 | Neilsen et al. |
| 2014/0067334 A1 | 3/2014 | Kuo |
| 2014/0067337 A1 | 3/2014 | Kopleman |
| 2014/0185742 A1 | 7/2014 | Chen et al. |
| 2014/0272772 A1 | 9/2014 | Andreiko et al. |
| 2014/0278278 A1 | 9/2014 | Nikolskiy et al. |
| 2014/0278279 A1 | 9/2014 | Azernikov et al. |
| 2014/0308624 A1 | 10/2014 | Lee et al. |
| 2014/0329194 A1 | 11/2014 | Sachdeva et al. |
| 2014/0379356 A1 | 12/2014 | Sachdeva et al. |
| 2015/0007830 A1 | 1/2015 | Remmers et al. |
| 2015/0049081 A1 | 2/2015 | Coffey et al. |
| 2015/0056576 A1 | 2/2015 | Nikolskiy et al. |
| 2015/0111168 A1 | 4/2015 | Vogel |
| 2015/0154678 A1 | 6/2015 | Fonte et al. |
| 2015/0182316 A1 | 7/2015 | Morales et al. |
| 2015/0320320 A1 | 11/2015 | Kopelman et al. |
| 2015/0347682 A1 | 12/2015 | Chen et al. |
| 2016/0135924 A1 | 5/2016 | Choi et al. |
| 2016/0148370 A1 | 5/2016 | Maury et al. |
| 2016/0239631 A1 | 8/2016 | Wu et al. |
| 2016/0256035 A1 | 9/2016 | Kopelman et al. |
| 2016/0256246 A1 | 9/2016 | Stapleton et al. |
| 2016/0367336 A1 | 12/2016 | Peijun et al. |
| 2017/0100214 A1 | 4/2017 | Wen |
| 2017/0135655 A1 | 5/2017 | Wang et al. |
| 2017/0231721 A1 | 8/2017 | Akeel et al. |
| 2017/0340418 A1 | 11/2017 | Raanan |
| 2018/0028063 A1 | 2/2018 | Elbaz et al. |
| 2018/0028064 A1 | 2/2018 | Elbaz et al. |
| 2018/0028065 A1 | 2/2018 | Elbaz et al. |
| 2018/0055600 A1 | 3/2018 | Matov et al. |
| 2018/0132982 A1 | 5/2018 | Nikolskiy et al. |
| 2018/0146934 A1 | 5/2018 | Ripoche et al. |
| 2018/0165818 A1 | 6/2018 | Tsai et al. |
| 2018/0184795 A1 | 7/2018 | Pai et al. |
| 2018/0189420 A1 | 7/2018 | Fisker |
| 2018/0206958 A1 | 7/2018 | Ohtake et al. |
| 2018/0206959 A1 | 7/2018 | Ohtake et al. |
| 2018/0303581 A1 | 10/2018 | Martz et al. |
| 2019/0231492 A1* | 8/2019 | Sabina ................ A61B 1/0638 |
| 2019/0259219 A1 | 8/2019 | Lancelle et al. |
| 2019/0269485 A1* | 9/2019 | Elbaz ................... A61B 5/1079 |
| 2019/0290408 A1 | 9/2019 | Fisker et al. |
| 2019/0374318 A1 | 12/2019 | Jesenko |
| 2020/0015943 A1* | 1/2020 | Reynard ................ G16H 40/63 |
| 2020/0060612 A1 | 2/2020 | Shen et al. |
| 2020/0085548 A1* | 3/2020 | Reynard ................. G06T 17/20 |
| 2020/0121429 A1 | 4/2020 | Pesach et al. |
| 2020/0170755 A1 | 6/2020 | Kumamoto et al. |
| 2020/0306012 A1 | 10/2020 | Roschin et al. |
| 2021/0169611 A1 | 6/2021 | Feng et al. |
| 2023/0127167 A1 | 4/2023 | Nikolskiy et al. |
| 2023/0130573 A1 | 4/2023 | Nikolskiy et al. |

FOREIGN PATENT DOCUMENTS

| | | |
|---|---|---|
| EP | 2345387 A2 | 7/2011 |
| EP | 2886077 A1 | 6/2015 |
| WO | WO 2001/080761 A2 | 11/2001 |
| WO | WO 2001/0807632 A2 | 11/2001 |
| WO | WO 2003/053274 A1 | 7/2003 |
| WO | WO 2013/180423 A1 | 5/2013 |
| WO | WO 2016/097033 A1 | 6/2016 |
| WO | WO 2017/178908 A1 | 10/2017 |
| WO | WO 2018/022054 A1 | 2/2018 |
| WO | WO 2018/038748 A1 | 3/2018 |
| WO | WO 2018/101923 A1 | 6/2018 |
| WO | WO 2018/167616 A1 | 9/2018 |
| WO | WO 2020/263950 A1 | 12/2020 |
| WO | WO 2020/263997 A1 | 12/2020 |
| WO | WO 2020/363987 A1 | 12/2020 |

OTHER PUBLICATIONS

Aho et al., "The Design and Analysis of Computer Algorithms," Addison-Wesley Publishing Company, Jun. 1974, pp. 124-155.
Arikan et al., "O-Snap: Optimization-based Snapping for Modeling Architecture," *ACM Transaction on Graphics,* vol. 32, No. 1, Article 6, Jan. 2013, 15 pages.
Bribiesca, "3D-Curve Representation by Means of a Binary Chain Code," *Mathematical and computer modeling,* 40.3 (2004): 285-295; p. 292, paragraph 2; p. 293, paragraph 1.
Cajaraville, "Four Ways to Create a Mesh for a Sphere," Medium. com, Dec. 7, 2015, 9 pages.
Cui et al., "Curve Matching for Open 2D Curves," *Pattern Recognition Letters,* 30 (2009): pp. 1-10.
Fan et al., "Virtual adjustment of the occlusal surface for complete denture tooth arrangement," *2015 International Symposium on Bioelectronics and Bioinformatics* (ISBB), IEEE, 2015.
Fitzgibbon et al., "Direct Least Squares Fitting of Ellipses," The University of Edinburgh, Department of Artificial Intelligence, Jan. 4, 1996, 15 pages.
Flugge et al., "Precision of Intraoral Digital Dental Impressions with iTero and Extraoral Digitization with the iTero and Model Scanner," *Am. Journal of Ortho and Dentofacial Orthopedics,* vol. 44, Iss. 3, pp. 471-478, Sep. 2014.
Gumhold et al., "Feature Extraction from Point Clouds," *Scientific Computing and Imaging Institute:* pp. 1-13, Proceedings, 10th International Meshing Roundtable, Sandia National Laboratores, pp. 293-305, Oct. 7-10, 2001.

(56)     References Cited

OTHER PUBLICATIONS

Holtt et al., "GPU-Based Direct vol. Rendering of Industrial CT Data," 2007, *VRVis Research Center,* 84 pages.

Ibraheem, "Reduction of artifacts in dental cone beam CT images to improve the three-dimensional image reconstruction," *Research Gate,* Article in Journal of Biomedical Science and Engineering, Jan. 2012.

Kiattisin et al., "A Match of X-Ray Teeth Films Using Image Processing Based on Special Features of Teeth," *SICE Annual Conference,* 2008, IEEE: Aug. 22, 2008: p. 97; col. 2, paragraph 2.

Kilic et al., GPU Supported Haptic Device Integrated Dental Simulation Environment, 6 pages.

Kim et al., "Efficient digitalization method for dental restorations using micro-CT data," *Scientific Reports,* vol. 7, No. 1, p. 44577, Mar. 15, 2017.

Kozen, "The Design and Analysis of Algorithms," *Texts and Monographs in Computer Science,* (c) 1992, Whole Book.

Kumar et al., "Improved segmentation of teeth in dental models," *Computer-Aided Design and Applications* 8.2 (2011): 211-224.

Kumar et al., Automatic Feature Identification in Dental Meshes, *Research Gate,* Article in computer-Aided Design and Applications, Aug. 2013, 24 pages.

Liao et al., "Automatic Tooth Segmentation of Dental Mesh Based on Harmonic Fields," Hindawi Publishing Corporation, *BioMed Research International,* vol. 2015, Article ID 187173, 11 pages.

Lorensen et al., "Marching Cubes: A High-Resolution 3D Surface Construction Algorithm," *Computer Graphics,* vol. 21, No. 4, Jul. 1987, 7 pages.

Pages et al., Generation of Computational Meshes from MRI and CT-Scan Data, *Research Gate,* ESAIM: Proceedings, Sep. 2005, vol. 14, 213-223, 12 pages.

Perez et al., "A Comparison of Hole-Filling Methods in 3D," *Int. J. Appl. Math. Comput. Sci.,* vol. 26, No. 4, pp. 885-903, 2016.

Rabbani et al., "Segmentation of Point Clouds Using Smoothness Constraint," *ISPRS* vol. XXXXVI, Part 5, Dresden, Sep. 25-27, 6 pages.

Rietzel et al., "Moving targets: detection and tracking of internal organ motion for treatment planning and patient set up," *Radiotherapy and Oncology,* vol. 73, supplement 2, Dec. 2004, pp. S68-S72.

Sedgewick et al., "Algorithms and Data Structures," Fall 2007, Department of Computer Science, Princeton University, https://www.cs.princeton.edu/~rs/AlgsDS07/, downloaded Oct. 28, 2021, 41 pages.

Wolfson, "On Curve Matching," *Robotics Research Technical Report,* Technical Report No. 256, Robotic Report No. 86 (Nov. 1986) New York University, Dept. of Computer Science, New York, New York 10012.

Yang, "Interactive Tooth Segmentation Method of Dental Model based on Geodesic," *Research Gate,* Jan. 2017, 6 pages.

Zheng et al., Finite Difference Error Analysis of Geometry Properties of Implicit Surfaces, 2011, *IEEE Symposium on Computers & Informatics,* 6 pages.

International Search Report and Written Opinion in International PCT Application No. PCT/US2020/039383 mailed Sep. 25, 2020.

International Search Report and Written Opinion in International PCT Application No. PCT/US2020/039324 mailed Oct. 19, 2020.

* cited by examiner

160

170

180

190

192

194

196

192
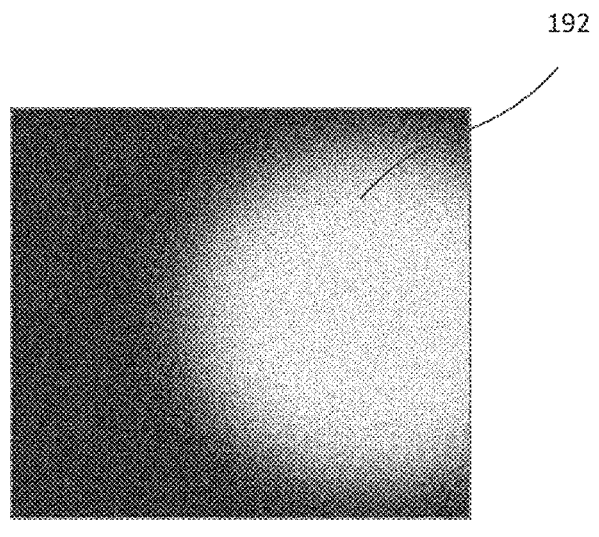
FIG. 8A
196
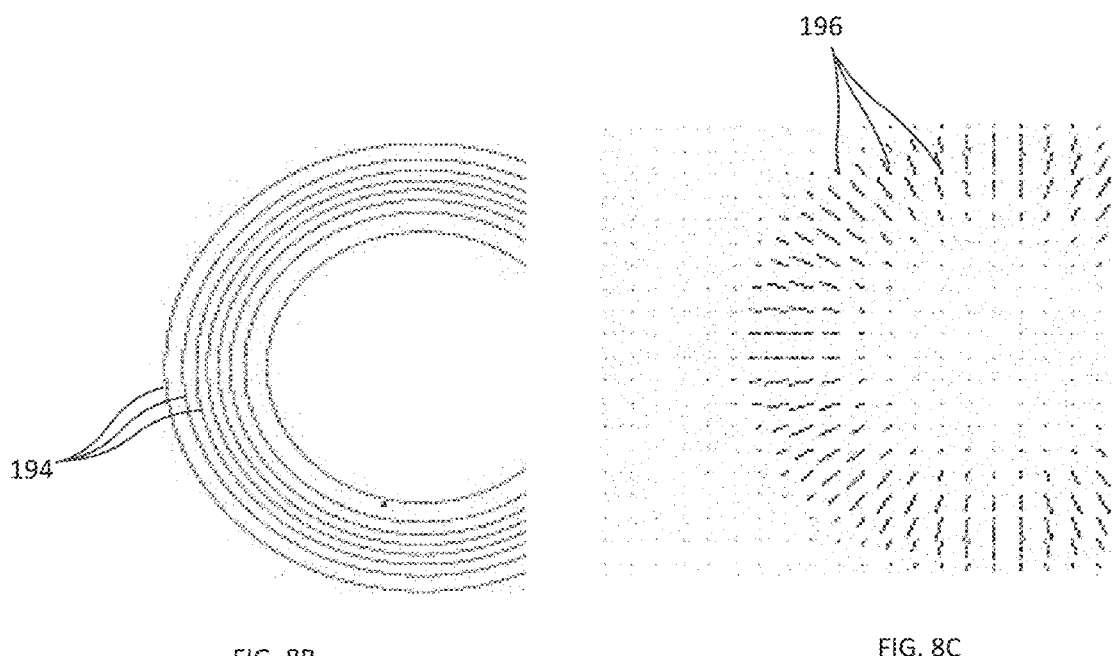
194
FIG. 8B                        FIG. 8C Select an iso-value of density for volumetric density file — 13002

Generate point cloud — 13004

Adjust point cloud — 13006

Create digital surface mesh for the adjusted point cloud — 13008

Optimize Surface — 13010

9000

9002

6006

11002

871

872

270 generating a density frequency distribution of a volumetric density file of a dental impression

272 determining an iso-value of density between air and a particular material in the density frequency distribution

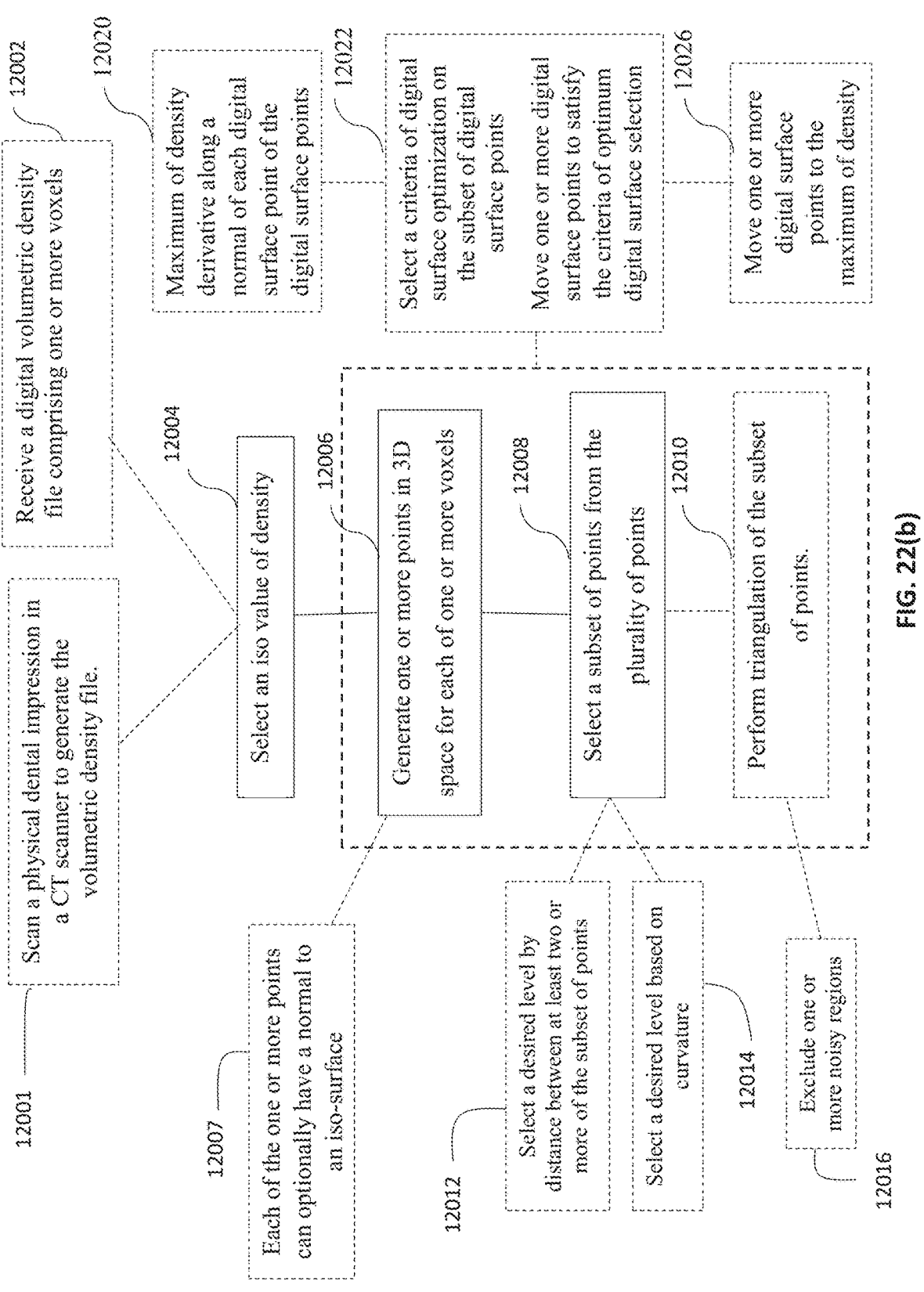

12001 — Scan a physical dental impression in a CT scanner to generate the volumetric density file.

12002 — Receive a digital volumetric density file comprising one or more voxels

12020 — Maximum of density derivative along a normal of each digital surface point of the digital surface points 12004 — Select an iso value of density 12006 — Generate one or more points in 3D space for each of one or more voxels 12007 — Each of the one or more points can optionally have a normal to an iso-surface 12008 — Select a subset of points from the plurality of points 12012 — Select a desired level by distance between at least two or more of the subset of points 12014 — Select a desired level based on curvature 12010 — Perform triangulation of the subset of points.

12016 — Exclude one or more noisy regions

12022 — Select a criteria of digital surface optimization on the subset of digital surface points Move one or more digital surface points to satisfy the criteria of optimum digital surface selection 12026 — Move one or more digital surface points to the maximum of density

FIG. 22(b)

PROCESSING CT SCAN OF DENTAL IMPRESSION

RELATED APPLICATIONS

This application is a continuation of U.S. patent application Ser. No. 18/069,473, filed Dec. 21, 2022, which is a continuation of and claims the benefit and priority to, U.S. patent application Ser. No. 16/451,315, filed Jun. 25, 2019, now U.S. Pat. No. 11,534,271, the entireties of each of which are incorporated by reference herein.

BACKGROUND

Specialized dental laboratories typically use computer-aided design (CAD) and computer-aided manufacturing (CAM) milling systems to manufacture dental prostheses based on patient-specific instructions provided by dentists.

In a typical work flow, the dental laboratories receive information about a patient's oral situation from a dentist. Using this information, the dental laboratory designs a dental prosthesis on the CAD system and manufactures the prosthesis on the CAM system with a mill or other fabrication system. To use the CAD/CAM system, a digital model of the patient's dentition is required as an input to the process. Several techniques may be used to produce a digital model.

Despite the rise of intraoral scanning technology, the prevalent method of generating digital model data still relies on scanning a stone model cast from an impression. Even in more technically advanced markets, it is estimated that only 25% of clinicians own an intraoral scanner.

Scanning and digitizing physical dental impressions directly into a digital model can be faster and more accurate than traditional techniques and systems. However, conventional techniques for generating a digital model can create an inaccurate digital surface topology and consume time and resources. A digital model can include a digital surface and a digital surface mesh each representing the digital surface topology of a physical impression. Conventional techniques typically generate the digital surface mesh from a volumetric image file by producing a large number of triangles. Due to the large number of triangles created, conventional techniques typically can require removing and modifying triangles by employing digital surface mesh simplification and smoothing in post-processing. The digital surface mesh simplification and smoothing in post-processing can result in a large number of degenerate triangles, resulting in a distorted and/or inaccurate digital surface mesh. Generation of the digital surface and digital surface mesh and its post-processing can also consume both time and valuable computing resources. For example, conventional digital surface and digital surface mesh generation techniques can take up to and including 10 minutes to generate a single digital model, thereby slowing production and tying up resources. Selecting the digital surface and generating the digital surface mesh from a volumetric image file of voxels can require setting an arbitrary iso-value. Since the iso-value can also influence position and shape of the digital surface selected from the volumetric image file, its arbitrary selection can lead to an inaccurate surface position, shape, and topology. For dental impressions, the iso-value of density can be selected from a wide range of values between air density and impression material density.

Due to the emerging need for processing digital models, any improvements to the conventional process are likely to remain relevant and benefit patients and clinicians alike for some time. Accordingly, improvements to systems and methods of generating digital models of patients' dentition are desirable.

SUMMARY

A computer-implemented method of determining a material surface from a volumetric density file is disclosed. The computer-implemented method includes generating a density frequency distribution of a volumetric density file of a dental impression and determining an iso-value of density between air and a particular material in the density frequency distribution.

A computer-implemented system of automatic detection of iso-value of density is disclosed. The system includes a processor, a computer-readable storage medium including instructions executable by the processor to perform steps, including: generating a density frequency distribution of a volumetric density file of a dental impression and determining an iso-value of density between air and a particular material in the density frequency distribution.

A computer-implemented method of creating a digital model from a CT scan of a physical dental impression is disclosed. An iso-value of density is selected for a digital volumetric density file having one or more voxels. One or more digital surface points in virtual 3D space for each of one or more voxels is generated. A subset of digital surface points from the one or more digital surface points is selected.

A digital impression processing system for creating a digital model from a CT scan of a physical dental impression, is disclosed. The system includes a processor, computer-readable storage medium having instructions executable by the processor to perform steps including selecting an iso-value of density for a digital volumetric density file including one or more voxels, generating one or more digital surface points in virtual 3D space for each of one or more voxels, and selecting a subset of digital surface points from the one or more digital surface points.

A non-transitory computer readable medium storing executable computer program instructions for creating a digital model from a CT scan of a physical dental impression is disclosed. The computer program instructions can include instructions for selecting an iso-value of density for a digital volumetric density file including one or more voxels, generating one or more digital surface points in virtual 3D space for each of one or more voxels and selecting a subset of digital surface points from the one or more digital surface points.

Also disclosed is a computer-implemented method of determining a material surface from a volumetric density file, including: generating a density frequency distribution of a volumetric density file of a dental impression and determining an iso-value of density between air and a particular material in the density frequency distribution is disclosed.

A computer-implemented system of automatic detection of iso-value of density, including a processor, a computer-readable storage medium comprising instructions executable by the processor to perform steps including: generating a density frequency distribution of a volumetric density file of a dental impression, and determining an iso-value of density between air and a particular material in the density frequency distribution is disclosed.

A computer-implemented system of automatic detection of iso-value of density, including: a processor, a computer-readable storage medium comprising instructions executable by the processor to perform steps including: generating a density frequency distribution of a volumetric density file of a dental impression, and determining an iso-value of density between air and a particular material in the density frequency distribution is disclosed.

A non-transitory computer readable medium storing executable computer program instructions for automatic detection of iso-value of density, the computer program instructions including instructions for: generating a density frequency distribution of a volumetric density file of a dental impression, and determining an iso-value of density between air and a particular material in the density frequency distribution is also disclosed.

A computer-implemented method of optimizing a digital surface, including: receiving a digital surface comprising a plurality of digital surface points, selecting a criteria of digital surface optimization on the digital surface points, and moving one or more digital surface points to satisfy the criteria of optimum digital surface selection is also disclosed.

A computer-implemented system of optimizing a digital surface, including: a processor, a computer-readable storage medium comprising instructions executable by the processor to perform steps including: receiving a digital surface comprising a plurality of digital surface points, selecting a criteria of digital surface optimization on the digital surface points, and moving one or more digital surface points to satisfy the criteria of optimum digital surface selection is also disclosed.

A non-transitory computer readable medium storing executable computer program instructions for optimizing a digital surface, the computer program instructions including instructions for: receiving a digital surface comprising a plurality of digital surface points, selecting a criteria of digital surface optimization on the digital surface points, and moving one or more digital surface points to satisfy the criteria of optimum digital surface selection.

BRIEF DESCRIPTION OF THE DRAWINGS

FIG. 8A is an illustration of a cross-section of the cylinder of FIG. 7.

FIG. 8B is an illustration of iso-surfaces derived from the 3D image of the cylinder of FIG. 7.

FIG. 8C is an illustration of gradient vectors derived from the iso-surfaces shown in FIG. 8B.

FIG. 9(*b*) is a perspective view of an illustration of a CT scanned image comprising a plurality of voxels.

FIG. 13(*b*) is a perspective view of an example of a portion of a 3 dimensional volumetric density file depicted for simplicity in 2 dimensions.

FIG. 13(*c*) is a perspective view of an example of a portion of a 3 dimensional point cloud depicted for simplicity in 2 dimensions.

FIG. 14(*b*) is a perspective view of a reduced point cloud.

FIG. 18(*b*) is an orthogonal view of a noisy portion of a digital model.

FIG. 18(*c*) is an orthogonal view of a digital surface mesh having a noisy region.

FIG. 18(*d*) is an orthogonal view of a digital surface mesh without triangulated noisy region.

FIG. 19(*b*) is a perspective view of a digital surface after hole patching.

FIG. 20(*b*) is an illustration of a normal of density for a point in a point cloud.

FIG. 20(*c*) is an illustration of a normal of density for a point in a 3D volumetric density file shown in two dimensions.

FIG. 21(*b*) is an illustration of an example of a cross section of a selected digital surface at a particular value of iso-value of density.

FIG. 22(*b*) illustrates a method of generating a digital surface mesh from a digital volumetric density file.

DETAILED DESCRIPTION

Figure 1:
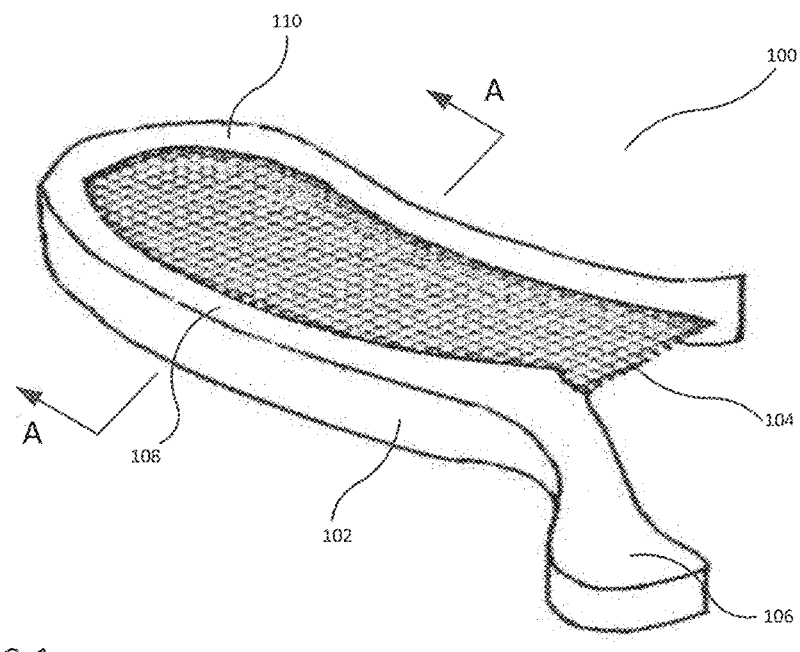
FIG. 1 is a perspective view of a three-way dental impression tray.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As noted above, in a typical work flow, information about the oral situation of a patient is received from a dentist, the dental laboratory designs the dental prosthesis, and the prosthesis is manufactured using a mill or other fabrication system. When making use of CAD design and CAM manufacturing in dentistry, a digital model of the patient's dentition is required as an input to the process. Despite the rise of intraoral scanning technology, the prevalent method of acquisition of digital model data is still scanning a stone model cast from a physical negative impression of the patient's dentition.

A physical negative impression of the patient's dentition is typically obtained by the use of a dental impression tray containing impression material. One example is described in U.S. Patent Application No. US20180132982A1 to Nikolskiy et al., which is hereby incorporated in its entirety by reference.

An example of an impression tray is shown in FIG. 1 in the form of a three-way impression tray or "triple tray" 100. The triple tray 100 includes a generally rigid frame 102 within which a mesh 104 is retained. The rigid frame defines a handle 106 configured to be gripped by the user, a buccal side wall 108, and a lingual side wall 110. In use, impression material is loaded onto the upper and lower surfaces of the mesh 104 by the clinician. The triple tray 100 is then inserted into the mouth of a patient and the patient is instructed to bite down onto the triple tray 100 and impression material, causing the impression material to conform to the patient's dentition as the impression material cures. Because the triple tray 100 is situated between the upper and lower jaws of the patient, the impression obtained via the triple tray 100 includes information about the dental situation of the patient's upper jaw, lower jaw, and bite registration in the area of the patient's dentition covered by the triple tray.

Figure 2:
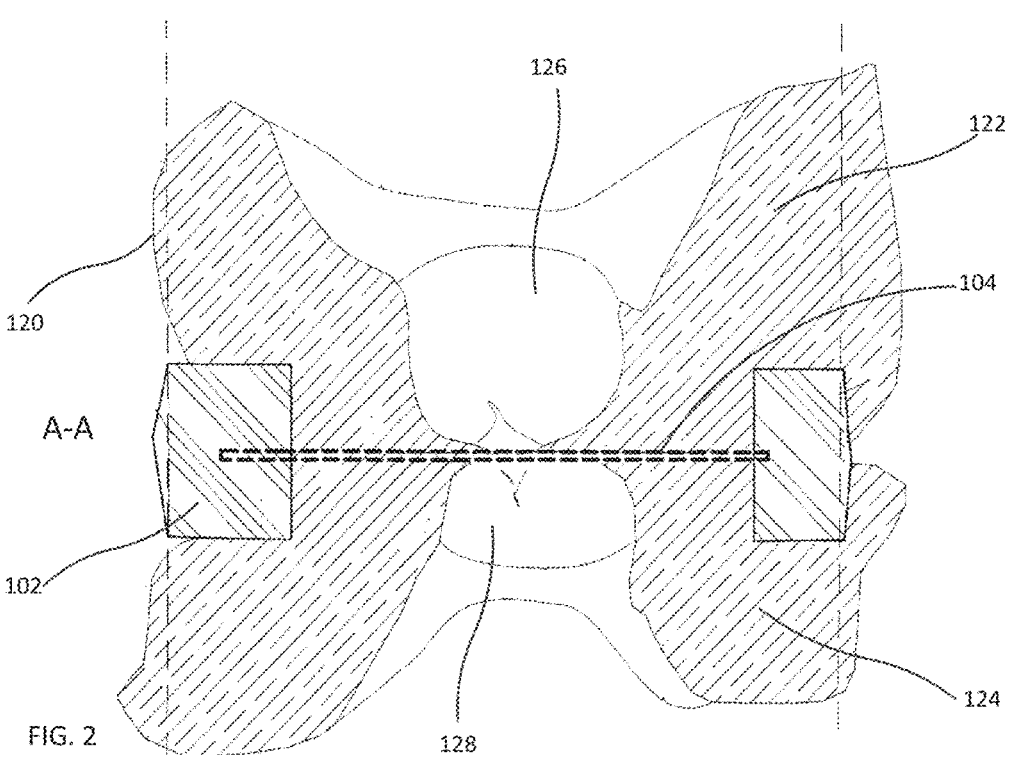
FIG. 2 is a cross-sectional view of a three-way dental impression tray containing impression material.

For example, in FIG. 2, there is shown a sectional view of the triple tray 100 containing impression material 120 after the taking of a physical impression of a patient. An upper impression 122 is formed on the upper side of the mesh 104, and a lower impression 124 is formed on the lower side of the mesh 104. As noted above, after deformation, the impression material 122 defines a physical negative impression of the patient's dentition. Accordingly, the upper void space 126 defined by the upper impression 122 defines the space occupied by the patient's teeth and gingiva in the patient's upper jaw, and the lower void space 128 defined by the lower impression 124 defines the space occupied by the patient's teeth and gingiva in the patient's lower jaw. Moreover, the position and orientation of the upper void space 126 relative to the lower void space 128 defines the bite registration of the patient's dentition in the subject area, including the occlusal spacing and registration.

As noted above, in a conventional workflow, a physical dental impression formed in the manner described above would be used to cast a model of the patient's dentition formed of stone, polymeric, or other suitable material. The cast model would then be scanned using an optical scanner in order to obtain a digital model. The digital model would then be used to design one or more restorations, or for other purposes. This conventional workflow creates potential sources of error or inaccuracy that would be avoided by alternative methods or alternative workflows that avoided the step of forming the cast model and, instead, proceeded directly from the physical impression to a digital model.

Figure 3:
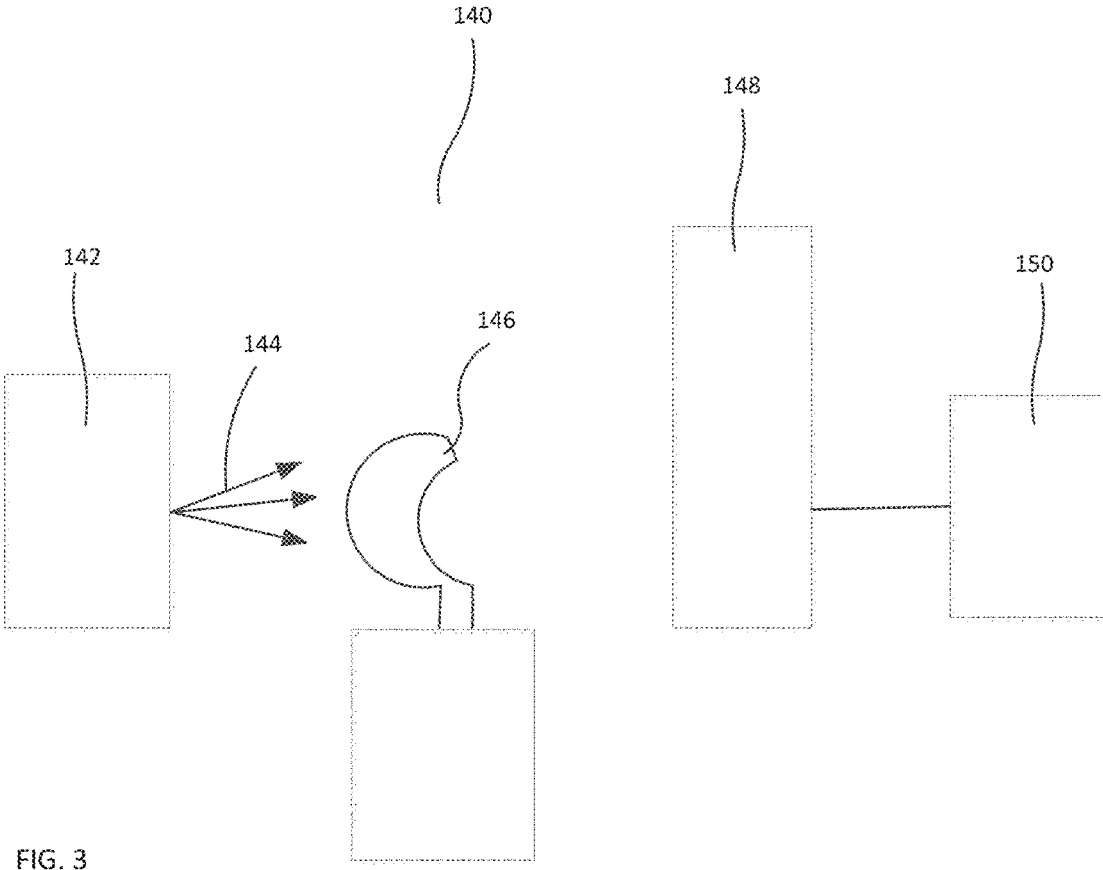
FIG. 3 is a schematic diagram of a computed tomography (CT) scanning system.

In one embodiment of the present method, a computed tomography (CT) scanner uses x-rays to make a detailed image of a physical impression. A plurality of such images are then combined to form a 3D model of the patient's dentition. A schematic diagram of an example of a CT scanning system 140 is shown in FIG. 3. The CT scanning system 140 includes a source of x-ray radiation 142 that emits an x-ray beam 144. An object being scanned—in the present case, a triple tray containing a physical impression 146—is placed between the source 142 and an x-ray detector 148. The x-ray detector 148, in turn, is connected to a processor 150 that is configured to receive the information from the detector 148 and to convert the information into a digital image file. Those skilled in the art will recognize that the processor 150 may comprise one or more computers that may be directly connected to the detector, wirelessly connected, connected via a network, or otherwise in direct or indirect communication with the detector 148.

An example of a suitable scanning system 140 includes a Nikon Model XTH 255 CT (Metrology) Scanner which is commercially available from Nikon Corporation. The example scanning system includes a 225 kV microfocus x-ray source with a 3 μm focal spot size to provide high performance image acquisition and volume processing. The processor 150 may include a storage medium that is configured with instructions to manage the data collected by the scanning system.

Figure 4:
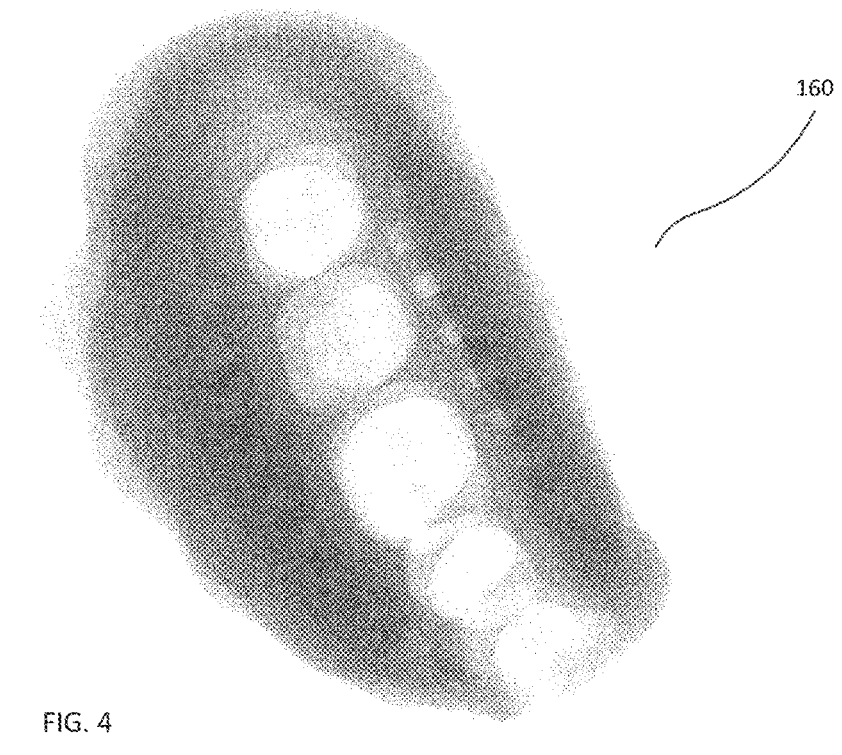
FIG. 4 is a 2-dimensional (2D) radiographic image of a dental impression tray containing a dental impression.

As noted above, during operation of the scanning system 140, the impression 146 is located between the x-ray source 142 and the x-ray detector 148. A series of images of the impression 146 are collected by the processor 150 as the impression 146 is rotated in place between the source 142 and the detector 146. An example of a single image 160 is shown in FIG. 4. The image 160 may be a radiograph, a projection, or other form of digital image. In one embodiment, a series of 720 images are collected as the impression 146 is rotated in place between the source 142 and the detector 148. In other embodiments, more images or fewer images may be collected as will be understood by those skilled in the art.

Figure 5:
FIG. 5 is a cross-section of a 3-dimensional (3D) volumetric image.

The plurality of images 160 of the impression 146 are generated by and stored within a storage medium contained within the processor 150 of the scanning system 140, where they may be used by software contained within the processor to perform additional operations. For example, in an embodiment, the plurality of images 160 undergo tomographic reconstruction in order to generate a 3D virtual image 170 (see FIG. 5) from the plurality of 2D images 160 generated by the scanning system 140. In the embodiment shown in FIG. 5, the 3D virtual image 170 is in the form of a volumetric image or volumetric density file (shown in cross-section in FIG. 5) that is generated from the plurality of radiographs 160 by way of a reconstruction algorithm associated with the scanning system 140.

Figure 6:
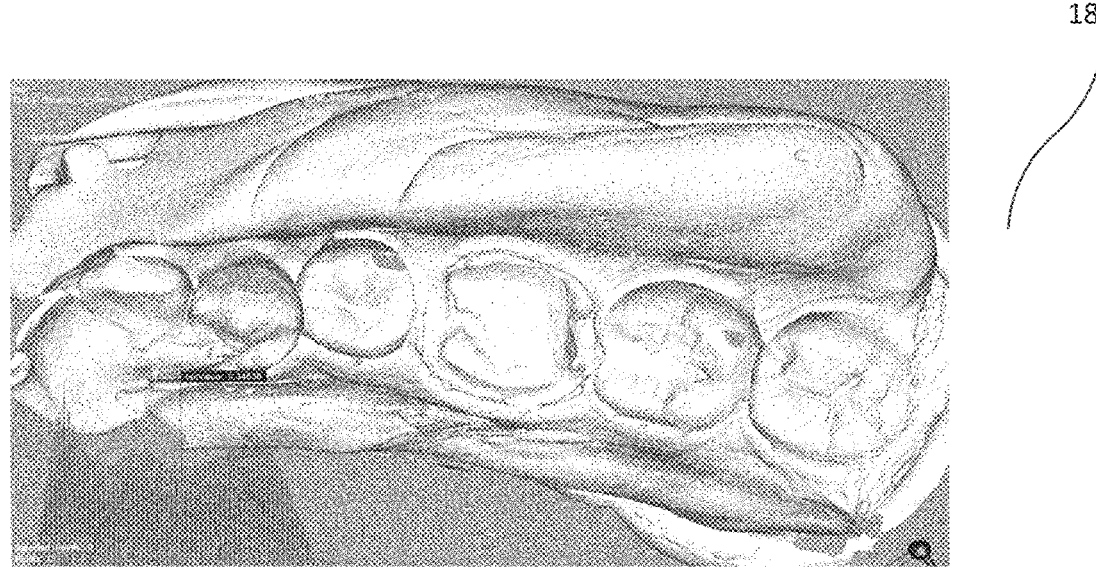
FIG. 6 is a 3-dimensional (3D) surface image representation of a portion of a patient's dentition.

In one embodiment, the volumetric image 170 is converted into a surface image 180 (see, e.g., FIG. 6) using a surface imaging algorithm. In the embodiment shown, the volumetric image 170 is converted into a surface image 180 having a format (e.g., an STL file format) that is suitable for use with a dental restoration design software, such as the FastDesign™ dental design software provided by Glidewell Laboratories of Newport Beach, Calif.

Figure 7:
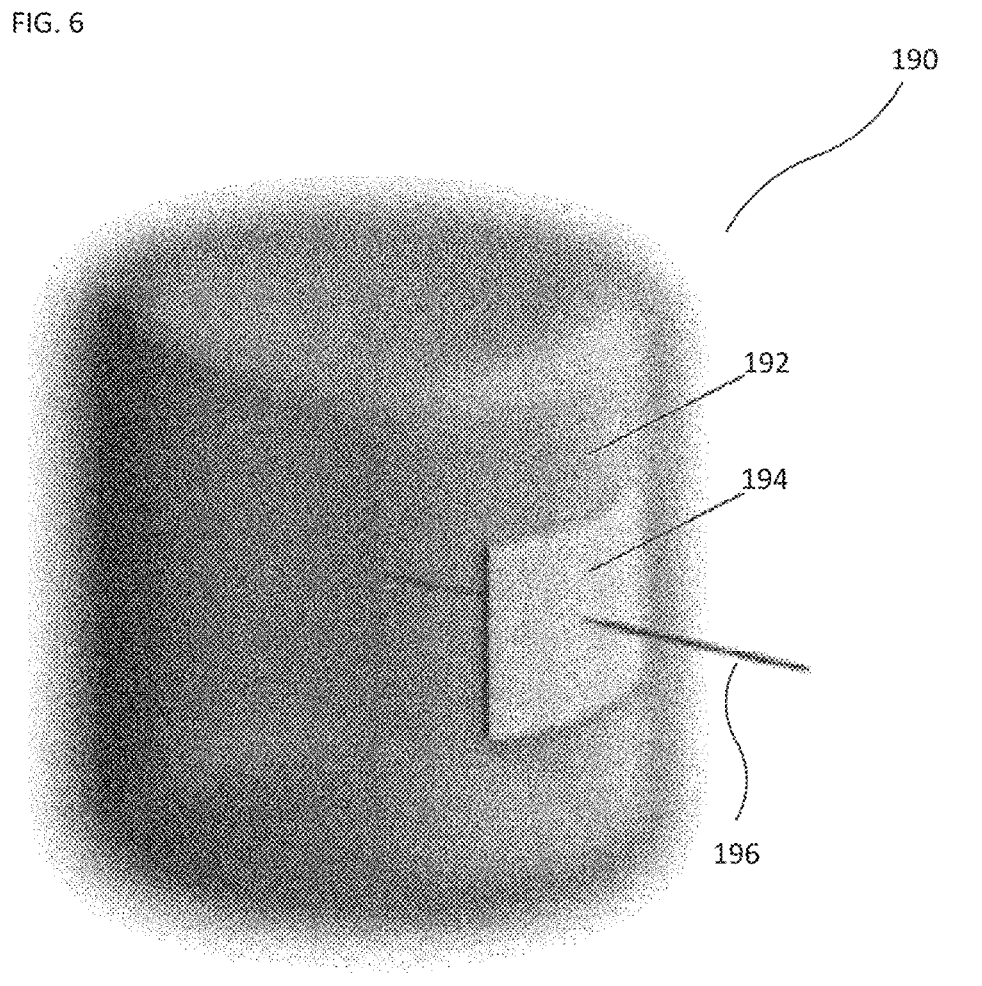
FIG. 7 is an illustration of a 3-dimensional (3D) object in the form of a cylinder.
Figure 8D:
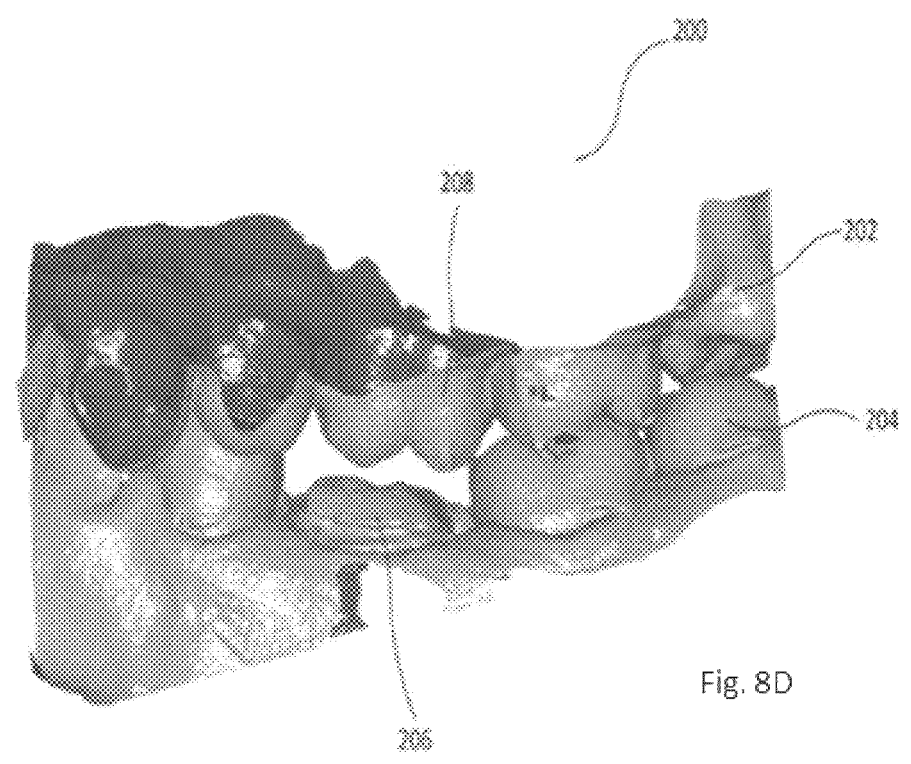
FIG. 8D is a perspective view of a surface image representation of a portion of a patient's dentition including portions of the dentition of an upper jaw and portions of the dentition of a lower jaw.

In one embodiment, the surface imaging algorithm used to convert the volumetric image 170 into a surface image 180 is configured to construct the surface image of the dentition 180 directly from the volumetric image 170 without including an intermediate step of constructing a surface image of the impression. For example, FIGS. 7 and 8A-C do not show images of a dental impression or of a patient's dentition, but are instead presented to illustrate by way of example the direct surface imaging method employed in the illustrated embodiment. In FIG. 7, a volumetric image 190 of an object having a boundary 192 that is not precisely defined. A small patch of an iso-surface 194 is illustrated within the boundary 192, with the iso-surface 194 representing a collection of points within the volumetric image 190 that have the same volumetric density value. It is a mathematical property that a gradient vector 196 at a given position will always point perpendicular to an iso-surface 194 at position. Accordingly, the gradient vector 196 is used to determine the direction which passes perpendicularly through the object boundary 192. These properties are further illustrated in FIGS. 8A-C, which show the non-precisely defined boundary 192 of the object (FIG. 8A), a plurality of iso-surfaces 194 of the object (FIG. 8B), and a plurality of gradient vectors 196 that are perpendicular to the iso-surfaces at given positions with in the object (FIG. 8C).

In the embodiment shown, as described above, a dental impression is collected using a triple tray 100 dental impression tray, thereby collecting an upper impression 122, a lower impression 124, and a bite registration in a single step. As a result, after scanning, reconstruction, and generation of a volumetric image of the triple tray and impression 146 (see FIG. 3), the resulting surface image 200 (see FIG. 8D)

includes a surface image of the upper dentition 202, a surface image of the lower dentition 204, and their relative positions and orientation providing information about the bite registration between the upper and lower dentition. These surface images 202, 204 and bite registration information are obtained using a single scan of a single object (the triple tray and impression 146).

Figure 9A:
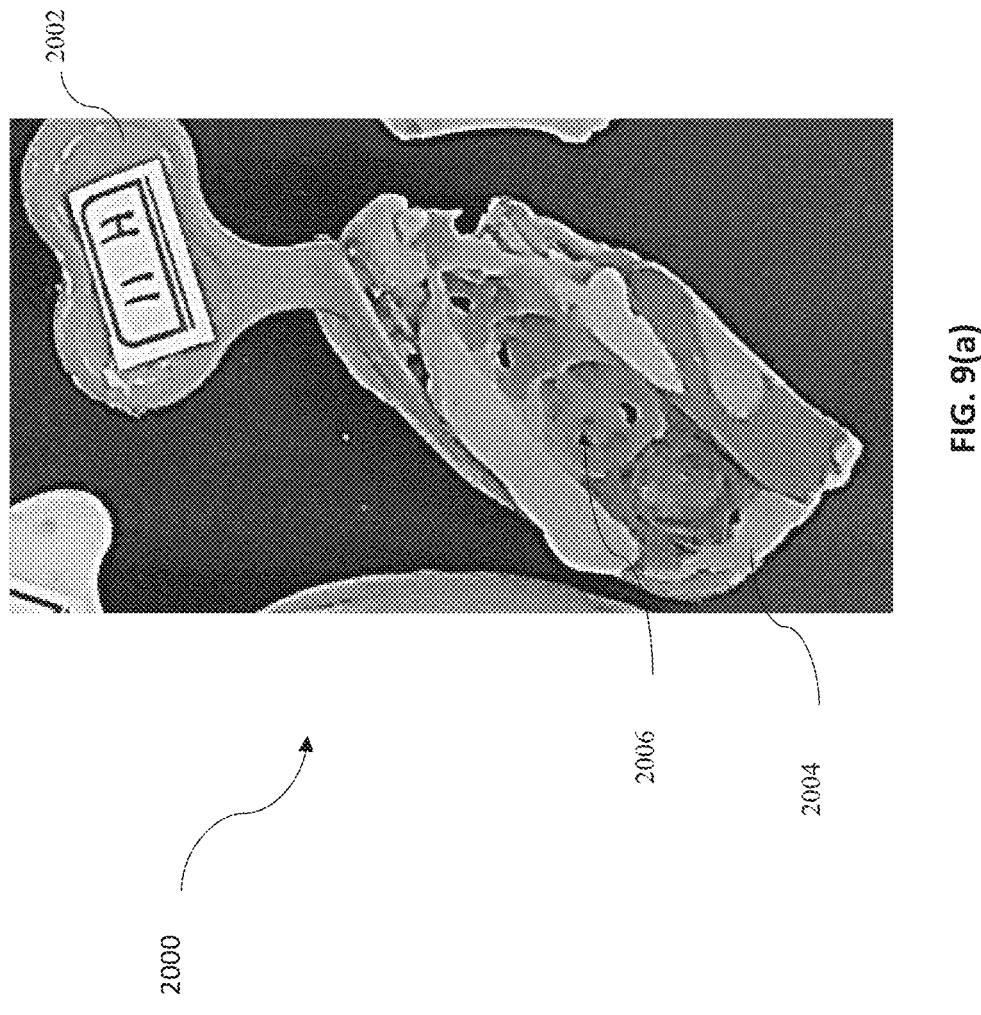
FIG. 9(*a*) is an orthogonal view of a physical dental impression.
Figure 9B:
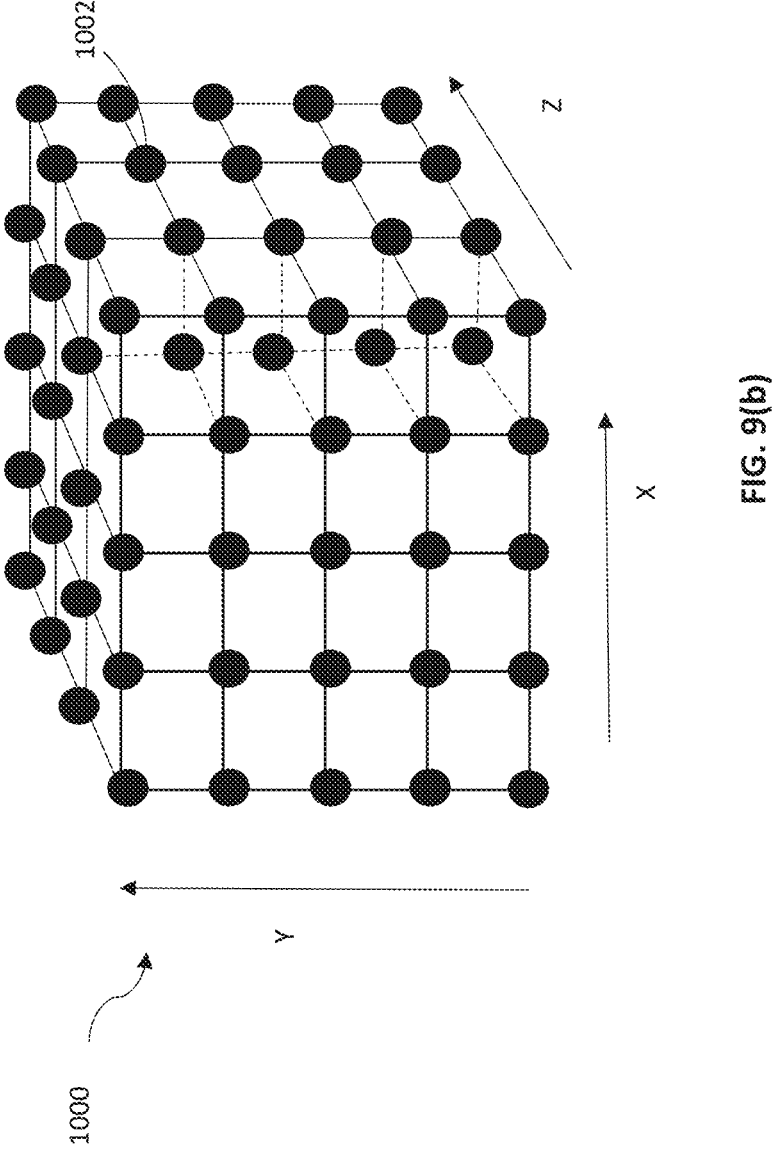

In some embodiments, a scan of a dental impression such as physical triple tray impression 2000 illustrated in FIG. 9(a) can include one or more regions such as handle material region(s) 2002, physical impression material region(s) 2004, and/or air region(s) 2006, for example. More or fewer regions can be present, and each region can have a unique density value. CT scanning the physical triple tray impression 2000 can produce the digital volumetric density file as a 3D volumetric grid 1000 of voxels 1002 with each voxel representing the density value of the region at a particular position in virtual 3D space as illustrated in FIG. 9(b). The voxels are arranged inside throughout every intersection within the volumetric density file; only one column of the interior voxels are illustrated for clarity. Each voxel can therefore contain position information and density information. Although a triple tray impression is illustrated, any type of physical dental impression can be CT scanned.

Exemplary embodiments of methods and systems are described herein. The computer-implemented executable methods of generating a digital model described herein can use the digital volumetric density file to generate the digital model. In some embodiments, the digital volumetric density file can be received. In some embodiments, the digital volumetric density file can be generated as described herein, or by any CT scanning system known in the art.

Figure 10:
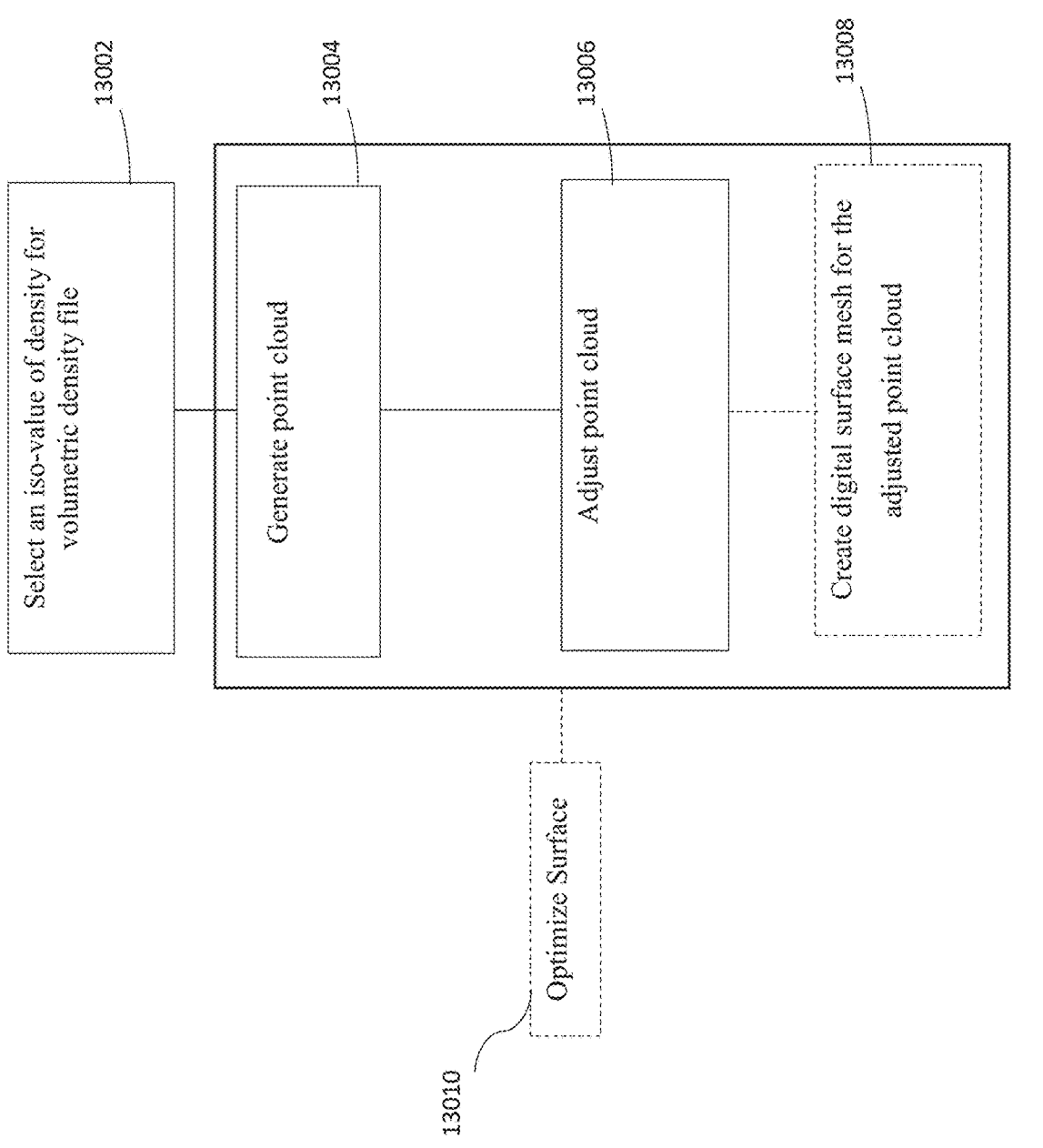
FIG. 10 illustrates a method of generating a digital surface mesh from a digital volumetric density file.

FIG. 10 illustrates a computer-implemented method for generating a digital model from a CT scan of a physical dental impression in some embodiments. An iso-value of density for a digital volumetric density file having one or more voxels is selected at 13002. In some embodiments, the volumetric density file can be received. In some embodiments, the volumetric density file can be generated by CT scanning the physical dental impression. A point cloud can be generated at 13004 having one or more digital surface points for each of the one or more voxels. The point cloud can be a set of digital surface points arranged in virtual 3D space and defining a digital surface from a volumetric density file at a selected level of density (iso-value of density). The selected digital surface can also be referred to as the "digital iso-surface". The generated point cloud can be adjusted at 13006. This can include, for example, reducing or sampling the generated point cloud in one or more areas. A digital surface mesh can be optionally created for the reduced point cloud at 13008. The surface can be optimized at 13010. This can include, in some embodiments, moving one or more digital surface points to a maximum density derivative position in some embodiments as detailed herein. This can occur at any step, including after point cloud generation at 13004, point cloud adjustment at 13006, or after digital surface mesh creation at 13008, for example.

Figure 11:
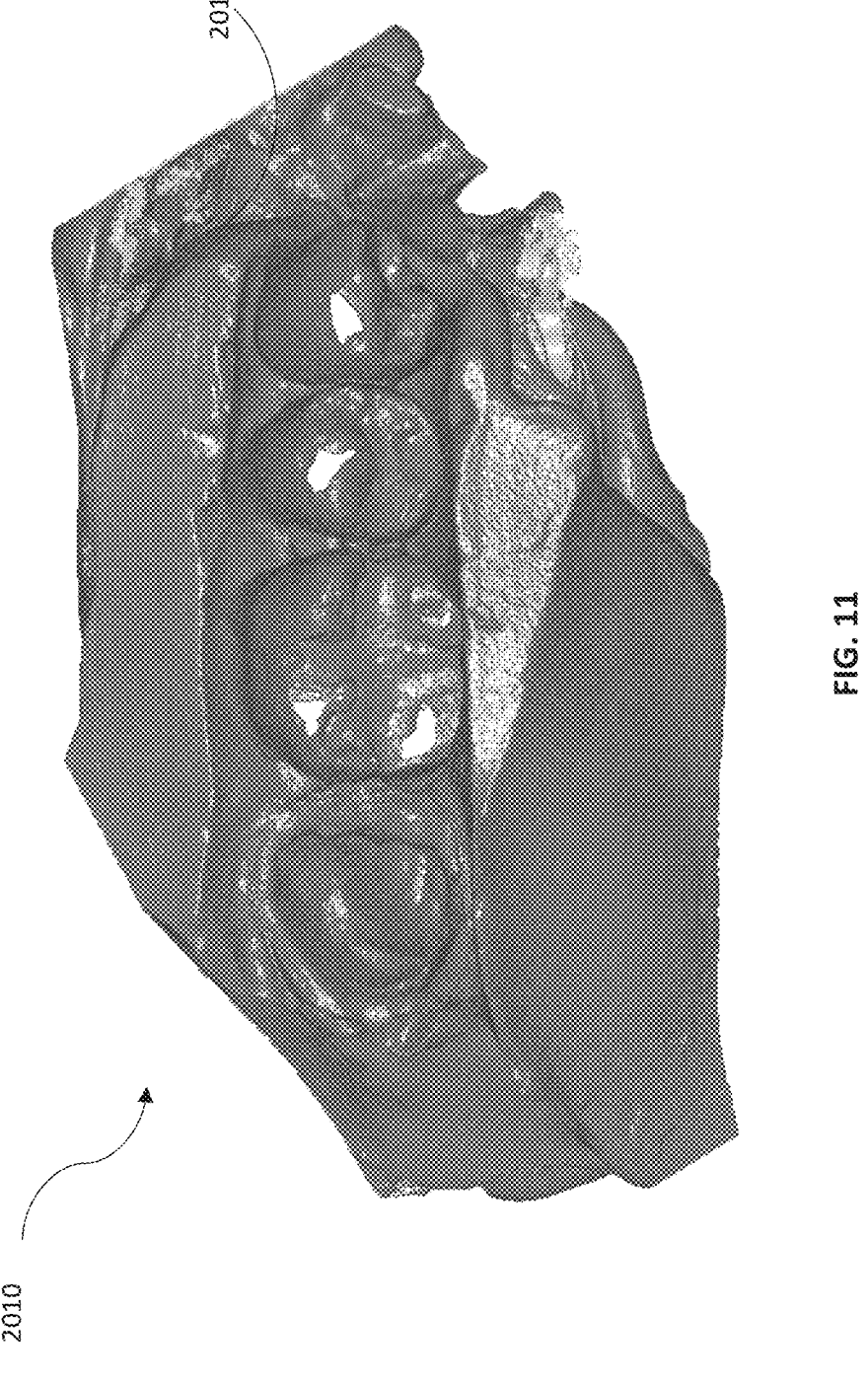
FIG. 11 is an orthogonal view of a processed digital model of a physical dental impression.

FIG. 11 illustrates an example of a digital model 2010 with digital surface mesh 2012 generated by one or more features described in one or more embodiments of the present disclosure. The point cloud can be viewed on a computer display and manipulated by a user or a computer system to show different user-selectable views of a digital model in some embodiments. Additionally, the iso-value of density can be altered or adjusted to generate or modify a point cloud to represent the digital surface at the altered/ adjust level of density.

Iso-Value of Density

In some embodiments, the computer-implemented system determines an iso-value of density of a digital surface of a particular material from a volumetric density file. In some embodiments, the iso-value(s) can be determined automatically. In some embodiments, the volumetric file can be received by the computer-implemented system.

Since the isosurface 194 represents a collection of points within the volumetric image 190 that have the same volumetric density value, determining the isosurface 194 requires determining the volumetric density value ("density") value of the material of the digital surface. Creating a digital surface from the volumetric density file thus requires determining an iso-value of density of the digital surface material.

The volumetric density file contains voxels having density information of one or more materials and surrounding air in a CT scan volume of a physical dental impression. The number of voxels at a particular density value can represent the amount of the material/air having that particular density. In some scans, air occupies most of the CT scan volume. This can occur, for example, in CT scans of triple tray impressions or other dental impressions that occupy a smaller volume of the CT scan volume than air. In such scans, since air has the highest volume, the number of voxels with a density value falling within the density range of air is highest. In some embodiments, the impression material occupies the second highest volume in the CT scan volume next to air. The number of voxels having a density falling within the density range of the impression material can therefore be the second highest. Similarly, other materials such as the handle can constitute the least amount of material and therefore occupy the least volume in the CT scan volume. The number of voxels having a density falling within the density range of the handle material can therefore have the lowest voxel count.

In another example, the dental impression material can occupy most of the CT scan volume. This can occur in CT scans of full arch impressions, for example, or other dental impressions that occupy more of the CT scan volume than air. In such scans, the impression material of the dental impression can occupy the most volume in the CT scan volume. The number of voxels having a density value falling within the density range of the impression material can therefore be the highest voxel count. The air in such a scan can occupy the second highest volume in the CT scan volume. The number of voxels having a density falling within the density range of air can therefore be the second highest voxel count. Similarly, other materials such as the handle can constitute the least amount of material in the CT scan so that the number of voxels having a density falling within the density range of the handle material can have the lowest voxel count.

As illustrated in the histogram 211 of FIG. 12(*a*), in some embodiments, the computer-implemented method can generate a density frequency distribution of the volumetric density file. The histogram 211 is shown for illustrative purposes and includes an x-axis 213 of density values and the y-axis 214 of the number of voxels (voxel counts), for example. All histograms illustrating the density frequency distribution herein include an x-axis of density values and a y-axis of the number of voxels (voxel counts). The computer-implemented method can receive a volumetric density file. The computer-implemented method can generate a normalized scan density range 201 for the volumetric density file. For example, in some embodiments, the computer-implemented method can generate the normalized scan density range 201 to be between 0.0 and 1.0. The computer-implemented method can subdivide the normalized scan density range into one or more scan density subranges 203 (scan density subrange 203 is shown among multiple scan density subranges in a magnified view). For example, the computer-implemented method can subdivide the normalized scan density range 201 of 0.0 and 1.0 into multiple scan density subranges 203. In some embodiments, the number of scan density subranges 203 can be 500, for example. In some embodiments, more or fewer scan density subranges 203 are possible. For each voxel, the computer-implemented method normalizes the density value of the voxel to fall within the normalized scan density range 201. The computer-implemented method compares the normalized density of the voxel with the one or more scan density subranges 203 and increments the voxel count for the scan density subrange 203 within which the normalized voxel density value falls. The computer-implemented method loads the next voxel from the volumetric density file and repeats the process for every voxel in the volumetric density file to determine the total voxel count for each of the scan density subranges 203. In some embodiments, the computer-implemented method takes a logarithm of the voxel counts for each scan density subrange 203. The computer-implemented method in this manner generates the density frequency distribution which is depicted as histogram 211 for illustrative purposes.

In some embodiments, the computer-implemented method uses the density frequency distribution to determine an iso-value of density of a digital surface of a particular material. In some embodiments, since the physical surface of the particular material is typically adjacent to air, the digital surface of the particular material can be between an air density range and a particular material density range in the density frequency distribution. The digital surface of the particular material can be found by determining an iso-value of density between air and the particular material in the density frequency distribution. In some embodiments, the computer-implemented method can determine the iso-value of density between the air density range and the particular material density range. In some embodiments, the particular material can be an impression material, for example, in which case the digital surface is that of the impression material. In some embodiments, the digital surface of the particular material can be found by determining an iso-value of density just below the density of the particular material in the density frequency distribution.

In some embodiments, the computer-implemented method can determine the air density range and the particular material density range based on voxel counts in the density frequency distribution. In some embodiments, the computer-implemented method can use voxel counts to determine one or more voxel count peaks as the highest voxel counts in the density frequency distribution. For example, the computer-implemented method can compare the voxel counts at each scan density subrange and determine which scan density subrange the voxel count either switches from increasing to decreasing, or begins decreasing. In some embodiments, a voxel count peak can span one or more scan density subranges. Other techniques can be used to determine voxel count peaks in the density frequency distribution. In some embodiments, the computer-implemented method can determine valleys by determining the scan density subranges the voxel count either switches from decreasing to increasing, or starts increasing. Other techniques can be used to determine valleys in the density frequency distribution. In some embodiments, a voxel count peak can span one or more scan density subranges. In some embodiments, the number of peaks in the density frequency distribution is proportional to the number of materials plus air in the CT scan volume, for example. In some embodiments, the valleys are arranged between two voxel count peaks.

Figure 12A:
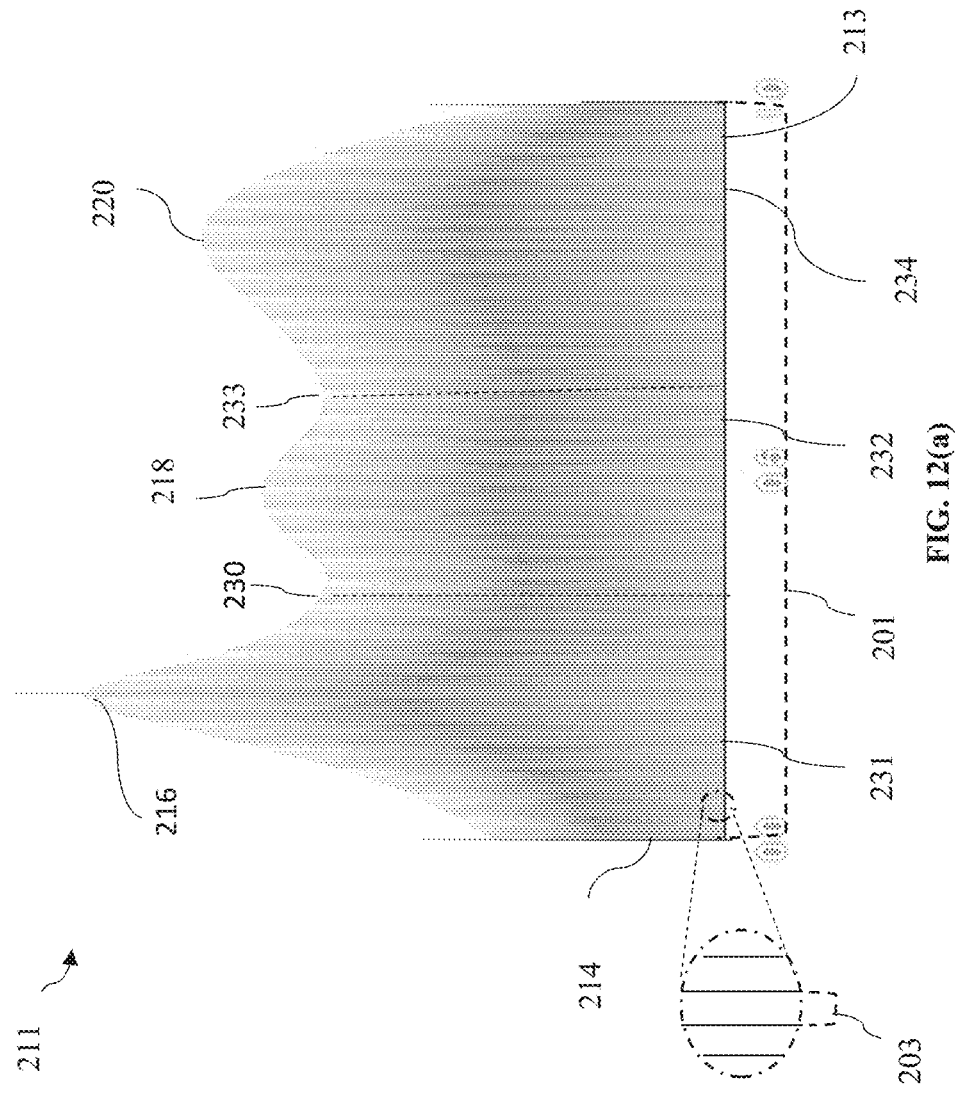
FIGS. 12(*a*)-12(*d*) are histograms illustrating a density frequency distribution.

For example, as illustrated in FIG. 12(a), the computer-implemented method can generate a density frequency distribution which is illustrated in the histogram 211. The computer-implemented method can determine a highest voxel count peak 216, second highest voxel count peak 220, and third voxel count peak 218, for example. Additional voxel count peaks can also be present and determined by the computer-implemented method. As discussed previously, highest voxel count peak 216, second highest voxel count peak 220, third voxel count peak 218 and any other peaks herein can span one or more scan density subrange(s). In some embodiments, the computer-implemented method determines a first valley 230 as the shortest height or least voxel count between the highest voxel count peak 216 and the second highest voxel count peak 220, and a second valley 233 as the shortest height or least voxel count between the second highest voxel count peak 220 and the third highest voxel count peak 218. Each valley can span one or more scan density subrange(s). The valleys can define a highest peak density range 231, a second highest peak density range 234, and a lowest peak density range 232, for example.

In some embodiments, the computer-implemented method can determine one or more material/air density ranges based on the type of impression scanned. In some cases, most of the CT scan volume can be air, followed by the volume of a particular material whose digital surface is desired, such as impression material, for example, followed by the volume other materials, such as the handle material in some embodiments, for example. In such cases, the air density range can correspond to the highest peak density range and the particular material density range can correspond to the second highest peak density range, for example. In other cases, most of the CT scan volume can be the particular material whose digital surface is desired, followed by air, followed by other materials, such as the handle material, for example. In such cases, the particular material density range can correspond to the highest peak density range and the air density range can correspond to the second highest peak density range, for example.

Some embodiments can also include additional materials such as implant coping material. This can include, for example, Titanium, which can correspond to the highest density in the density frequency distribution.

In some embodiments, the computer-implemented method can determine an iso-value of density between the air density range and the particular material density range. The computer-implemented method receives a volumetric density file and generates a density frequency distribution. The computer-implemented method receives information regarding a type of impression scanned including the presence of any implant coping material. The computer-implemented method determines whether air or the particular material occupies the most volume of the CT scan volume based on the type of impression scanned. In some embodiments, the computer-implemented method determines air occupies the most volume if the impression type is a triple tray impression, for example. In some embodiments, the computer-implemented method determines the particular material occupies the most volume if the impression type is a full arch impression, for example. The computer-implemented method determines voxel count peaks in the density frequency distribution. If the computer-implemented method determines that air occupies most of the CT scan volume and the particular material occupies the second highest volume based on the type of impression scanned, the computer-implemented method determines the air density range as the one or more density subranges of the highest voxel count peak and the particular material density range as the one or more density subranges of second highest voxel count peak. If the computer-implemented method determines that a particular material occupies most of the CT scan volume and air occupies the second most based on the type of impression scanned, the computer-implemented method determines the particular material density range as the one or more density subranges of the highest voxel count peak and the air density range as the one or more density subranges of the second highest peak. The computer-implemented method chooses an iso-value of density between the air density range and the particular material density range. In some embodiments, the computer-implemented method outputs an iso-value of density between the one or more density subranges of the highest voxel count peak and one or more density subranges of the second highest peak, for example. Optionally, in some embodiments, if the computer-implemented method has received information that implant coping material is present, the computer-implemented method determines the last peak by order (or the highest density peak) as the implant coping material and also outputs the iso-value of density at or in some embodiments just below the density of the implant coping material. In some embodiments, the implant coping material can be Titanium.

In the example of FIG. 12(a), air occupies the most CT scan volume. The computer-implemented method can determine that the highest peak density range 231 is the air density range and the second highest peak density range 234 is the particular material density range. The computer-implemented method can choose the iso-value of density between the highest peak density range 231 and the second highest peak density range 234, for example. In some embodiments, the computer-implemented method can choose an iso-value between the first valley 230 and the second valley 233. In some embodiments, the computer-implemented method can choose an iso-value of density at a mid-point between the first valley 230 and the second valley 233.

Figure 12B:
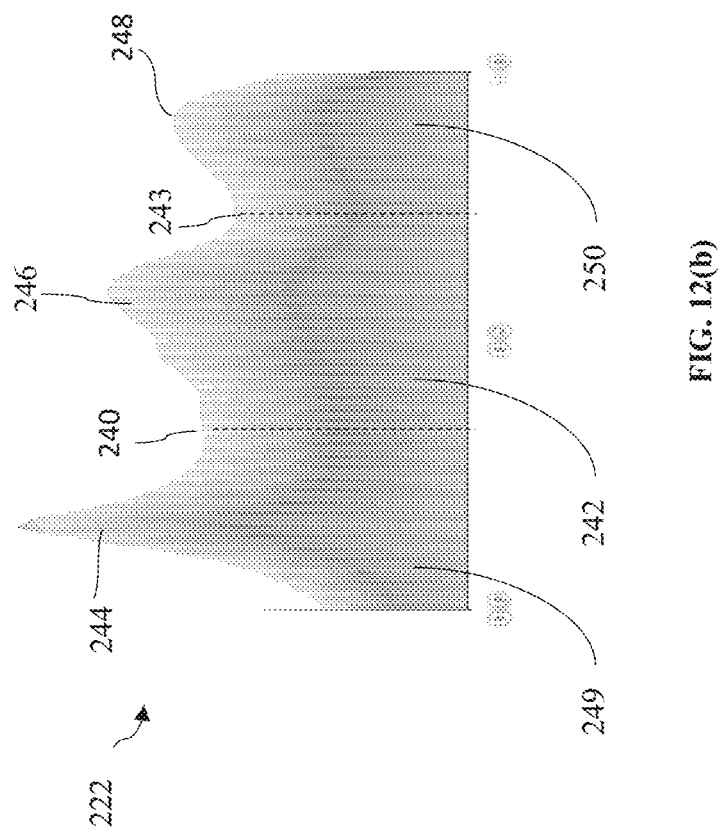
Figure 12C:
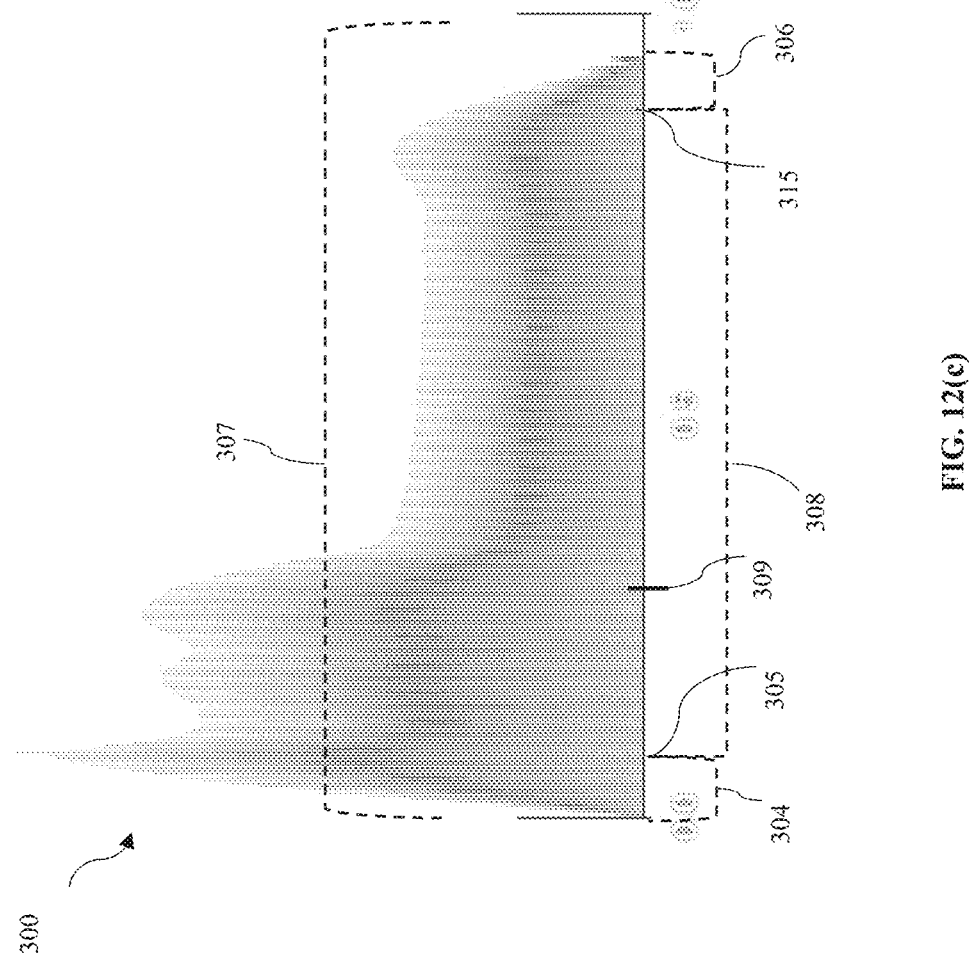
Figure 12D:
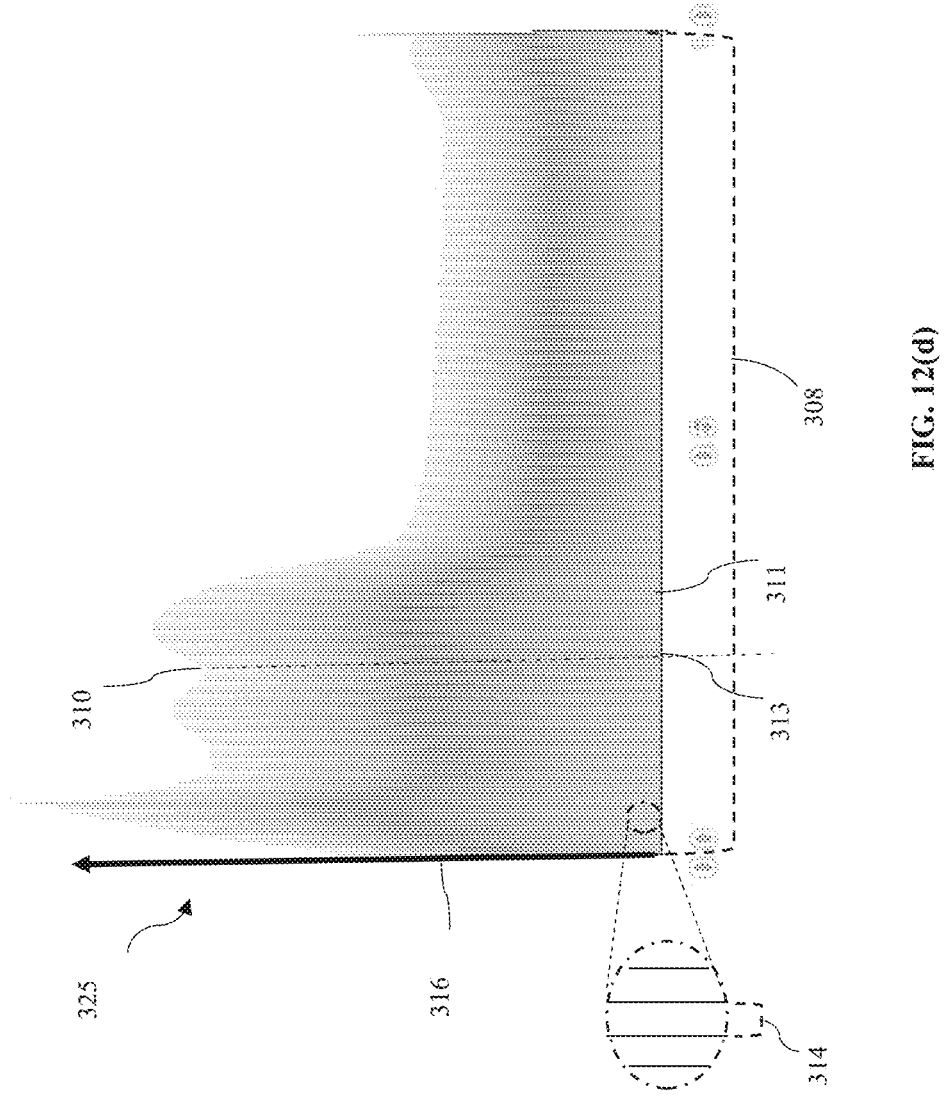

FIG. 12(b) illustrates another example in which the other material such as the handle, for example, has a greater density than the particular material whose digital surface is to be determined. In FIG. 12(b), air occupies the most CT scan volume. The computer-implemented method generates a density frequency distribution as represented by histogram 222 for illustrative purposes. The density frequency distribution can include a highest voxel count peak 244, a second highest voxel count peak 246, and a third highest voxel count peak 248. The computer implemented-method determines that air occupies the most CT scan volume. The computer-implemented method determines the air density range as the highest voxel count peak 244 and the particular material density range as the second highest voxel count peak 246. The computer-implemented method chooses an iso-value of density between the air density range and the particular material density range by choosing an iso-value of density between the highest voxel count peak 244 and the second highest voxel count peak 246, for example.

In some embodiments, total voxel counts in the density ranges can be used instead of voxel count peaks to determine an iso-value of density between the air density range and the particular material density range. For example, in some embodiments, the computer-implemented method receives a volumetric density file and generates a density frequency distribution. The computer-implemented method receives information regarding a type of impression scanned including the presence of any implant coping material. The computer-implemented method determines whether air or the particular material occupies the most volume of the CT scan volume based on the type of impression scanned. In some embodiments, the computer-implemented determines air occupies the most volume if the impression type is a triple tray impression. In some embodiments, the computer-implemented determines the particular material occupies the most volume if the impression type is a full arch impression. The computer-implemented method determines voxel count peaks in the density frequency distribution. The computer-implemented method determines one or more voxel count valleys between the voxel count peaks. The computer-implemented method determines one or more density ranges between the valleys, between 0.0 or the minimum density value of the normalized density range and a first valley, and between the last valley and the maximum density value of the normalized density range. The computer-implemented method calculates a density range voxel count for each of the one or more density ranges. In some embodiments, the computer-implemented method can count the total number of voxels in each of the one or more density ranges. In some embodiments, the computer-implemented method can perform an integration on a curve that connects the voxel count peaks within each of the one or more density ranges. If the computer-implemented method determines air occupies most of the CT scan volume and the particular material occupies the second highest volume based on the type of impression scanned, the computer-implemented method determines the air density range as the highest voxel count density range and the particular material density range as the second highest voxel count density range. If the computer-implemented method determines that a particular material occupies most of the CT scan volume and air occupies the second most based on the type of impression scanned, the computer-implemented method determines the air density range as the second highest voxel count density range and the particular material density range as the highest highest voxel count density range. The computer-implemented method chooses an iso-value of density between the air density range and the particular material density range. In some embodiments, the computer-implemented method outputs an iso-value of density between the highest voxel count density range and the second density range voxel count, for example. Optionally, in some embodiments, if the computer-implemented method has received information that implant coping material is present, the computer-implemented method determines the last density range by order or highest density range as the implant coping material and also outputs the iso-value of density of the implant coping material. In some embodiments, the implant coping material can be Titanium.

For example, the computer-implemented method generates a density frequency distribution illustrated as histogram 211 in FIG. 12(a) as described previously. As shown in FIG. 12(a), the computer-implemented method determines voxel count peaks 216, 218, and 220 and valleys 230 and 233, thereby establishing density ranges between density value 0.0 and density value at first valley 230, between density value at first valley 230 and density value at second valley 233, and between density value at second valley 233 and the maximum normalized density value. In this example, the maximum normalized density value is 1.0, for example. The computer-implemented method can determine the total number of voxels between density value 0.0 and the first valley 230, between the first valley 230 and the second valley 233, and the total number of voxels between the second valley 233. In the example of FIG. 12(a), if the computer-implemented method receives information that the dental impression type is a triple tray, then the computer-implemented determines that the highest voxel count density range corresponds to air. For example, if the density range between 0.0 and the first valley 230 contains the highest voxel count density range, then the computer-implemented method determines that density range as an air density range. If the density range between the second valley 233 and the maximum normalized density range value of 1.0 contains the second highest voxel count density range for example, then the computer-implemented method determines that density range as the particular material density range. The computer-implemented method selects an iso-value between the air density range and the particular material density range.

Similarly, as illustrated in the example of FIG. 12(b), the computer-implemented method can generate a density frequency distribution as described previously, the computer-implemented method determines voxel count peaks 244, 246, and 248 and valleys 240 and 243, thereby establishing density ranges between density value 0.0 and density value at first valley 240, between density value at first valley 240 and density value at second valley 243, and between density value at second valley 243 and the maximum normalized density value. In this example, the maximum normalized density value is 1.0, for example. The computer-implemented method can determine the total number of voxels between density value 0.0 and the first valley 240 as total voxel count 249, between the first valley 240 and the second valley 243 as total voxel count 242, and the total number of voxels after the second valley 243 as total voxel count 250. In this example, if the computer-implemented method receives information that the dental impression type is a triple tray, then the computer-implemented determines that the highest voxel count density range will correspond to air. For example, if the total voxel count 249 is the highest voxel count density range, then the computer-implemented method determines that the density range between 0.0 and the first valley 240 as an air density range. If the total voxel count 242 is the second highest voxel count density range for example, then the computer-implemented method determines that the density range between the first valley 240 and the second valley 243 is the particular material density range. The computer-implemented method selects an iso-value between the air density range and the particular material density range.

In some embodiments as illustrated in the examples, the computer-implemented method determines density range voxel counts by calculating an area beneath the voxel count curve extending between the particular density range endpoints. For the example of FIG. 12(a), the computer-implemented method can determine an area beneath the curve defined by the voxel counts between 0.0 and the density value at first valley 230 to determine the total voxel count for that density range. The computer-implemented method can determine an area beneath the curve defined by the voxel counts between the density value at first valley 230 and the density value at the second valley 233 to determine the total voxel count for that density range. The computer-implemented method can determine an area beneath the curve defined by the voxel counts between the density value at the second valley 233 and the highest density of the normalized density range to determine the total voxel count for that density range. The same method steps can be applied to the example of FIG. 12(*b*) and of any density frequency distribution, for example. In some embodiments, these areas beneath the curves can be calculated by performing integration on the respective curve with limits corresponding to the density value endpoints of a particular density range.

Contaminant Material Detection

In some embodiments, contaminant materials can be present in the physical dental impression and can distort the density frequency distribution. Contaminant materials can include, for example, dental cement, or materials other than impression, handle, tray, or implant coping materials, for example. The contaminant materials can have much higher density than the density of the dental impression material, handle, or tray.

In some embodiments, the computer-implemented method detects the presence of contaminant materials based on the density frequency distribution of a volumetric density file. The computer-implemented method can detect contaminant materials after CT scanning and reject a contaminated CT scan entirely from automatic iso-surface generation. In some embodiments, the computer-implemented method determines the presence of contaminant materials automatically. In some embodiments, the computer-implemented method can receive the volumetric density file.

In some embodiments, the computer-implemented method receives a volumetric density file and generates an initial density frequency distribution as illustrated by histogram 300 illustrated in FIG. 12(*c*) as described previously. The initial density frequency distribution includes an initial normalized scan density range 307. The computer-implemented method can then trim a portion of the lowest and highest samples from the initial density frequency distribution as illustrated by histogram 300. The amount trimmed can vary. In some embodiments, for example, the computer-implemented method can trim the 0.001% of the lowest samples 304 and 0.001% of the highest samples 306 from the initial density frequency distribution illustrated by histogram 300. The computer-implemented method can re-normalize the initial normalized scan density range 307 to generate a trimmed scan density range 308 as follows:

If the trimmed scan density range 308 *f* has a first scan density 305 *a* and a last scan density 315 *z*, then the trimmed scan density range 308 where any scan density 309 *x* is a density value in between a and z is f'=(x−a)/(z−a). The trimmed scan density range 308 can be between 0.0 and 1.0, in some embodiments, for example.

As illustrated in FIG. 12(*d*), the computer-implemented method can subdivide the trimmed scan density range 308 into trimmed scan density subranges 314. The computer-implemented method can re-normalize each voxel as discussed previously. For example, for each voxel, the computer-implemented method re-normalizes the density value of the voxel to fall within the trimmed scan density range 308. The computer-implemented method compares the re-normalized density value of the voxel with the one or more trimmed scan density subranges 314 and increments the voxel count for the trimmed scan density subrange 314 within which the re-normalized voxel density value falls. Voxel counts are illustrated in the histogram along the y-axis 316. The computer-implemented method loads the next voxel from the volumetric density file and repeats the process for every voxel in the volumetric density file to determine the total voxel count for each trimmed scan density subrange 314. In some embodiments, the computer-implemented method takes a logarithm of the voxel counts for each trimmed scan density subrange. The computer-implemented method in this manner generates the trimmed density frequency distribution which is illustrated as histogram 325. In some embodiments, the trimmed scan density range 308 as illustrated by histogram 325 can be between 0.0 and 1.0, for example.

To detect contaminants in the scan, the computer-implemented method can then determine a density subrange of a second valley 310 in the trimmed density frequency distribution illustrated in histogram 325. If the density subrange value 313 of the second valley 310 is below a user-selectable contaminant density threshold 311, then the computer-implemented method rejects the CT scan from isosurface generation and the CT scan is not further processed. As an example, in some embodiments, the user-selectable contaminant density threshold 311 can be set to 0.3.

In the example illustrated in the histogram FIG. 12(*d*), because the density value 313 of the second valley 310 is less than the contaminant density threshold 311, the computer-implemented method classifies the CT scan as contaminated and removes the CT scan from further processing.

If, on the other hand, the second valley 310 has a density value greater than the user-selectable contaminant density threshold such as threshold 311, for example, the computer-implemented method classifies the CT scan as not contaminated and allows the trimmed density frequency distribution illustrated by histogram 325 to be further processed to determine the iso-value and extract the isosurface as described in the present disclosure.

In some embodiments the computer-implemented method can detect contaminated dental impression scans by comparing the density subrange count between the highest and second highest voxel count peaks. For example, the computer-implemented method can receive a volumetric density file of a dental impression scan, generate an initial density frequency distribution, determine a trimmed density frequency distribution from the initial density frequency distribution, and renormalize voxels as described previously. The computer-implemented method can determine the air density range and the particular material density range based on voxel count peaks and the type of dental impression scanned as described previously. The computer-implemented method can determine the density subrange count between the air density range and the particular material density range. In some embodiments, the computer-implemented method can determine the density subrange count between the highest voxel count peak and the second-highest voxel count peak. In some embodiments if the density subrange count is less than a threshold parameter, the computer-implemented method determines the scan is contaminated and notifies an operator and/or removes the CT scan from further processing. If the density subrange count is greater than the threshold parameter, then the computer-implemented method determines the dental impression is not contaminated and allows the trimmed density frequency distribution illustrated by histogram 325 to be further processed to determine the iso-value and extract the isosurface as described in the present disclosure. In some embodiments, the threshold parameter can be 0.2, for example.

Once the iso-value of density of the particular material is determined, it can be provided/made available to other systems/computer-implemented methods used, for example, to extract an iso-surface. Both determining the iso-value of density and extracting an iso-surface can occur automatically without user information/input. The terms "peaks" and "valleys" can, in some embodiments, represent maximums and minimums, or ranges of maximums and minimums, respectively, for example. For example, a "peak" can refer to one or more maximum data points and a valley can represent one or more data points between two maximum data points.

One or more of the features described in the present disclosure can be performed automatically by the computer-implemented method, without user interaction.

Some advantages of the features described in this disclosure include, but are not limited to, for example, determining the iso-value of density value rather than setting it randomly or based on previous or other scans. Another advantage is, for example, avoiding subjective manual guessing/setting of the iso-value of density by user. Instead, for example, the system empirically itself automatically can calculate the iso-value of density from the scan itself. This can, for example, advantageously improve accuracy and reduce processing time in determining iso-value of density, and thus allow extraction of the proper iso-surface of the impression material in some embodiments.

One advantage of automatically detecting contaminated CT scans is to improve the accuracy of the iso-density value and the isosurface extracted from the voxel file. This can provide an improved and more accurate digital representation of the physical dental impression's surface topology, for example.

Point Cloud Generation

In some embodiments, the computer-implemented method can generate a point cloud based on a selected iso-value of density for a volumetric density file. The point cloud can be generated by the computer-implemented method in some embodiments by comparing a selected iso-value of density to densities of one or more voxels in a volumetric density file and generating digital surface points at the selected iso-value of density in a point cloud. The iso-value of density can be a selectable value that can be chosen by a user and/or can be automatically determined in some embodiments and provided to the computer-implemented method. In some embodiments, the volumetric density file can be received by the computer-implemented method.

For example, if the selected iso-value of density corresponds to the density of one or more voxels in the volumetric density file, then zero or more digital surface points can be generated and arranged in virtual 3D space at position(s) in the point cloud corresponding to position(s) of one or more voxels in the volumetric density file by the computer-implemented method. In some embodiments, as discussed below, if the selected iso-value of density is between two voxel density values, then zero or more digital surface points can be generated and arranged in virtual 3D space in position(s) corresponding to position(s) between two voxel positions along a voxel edge by the computer-implemented method. In some embodiments, the computer-implemented method generates the point cloud automatically using a selected iso-value of density.

Figure 13A:
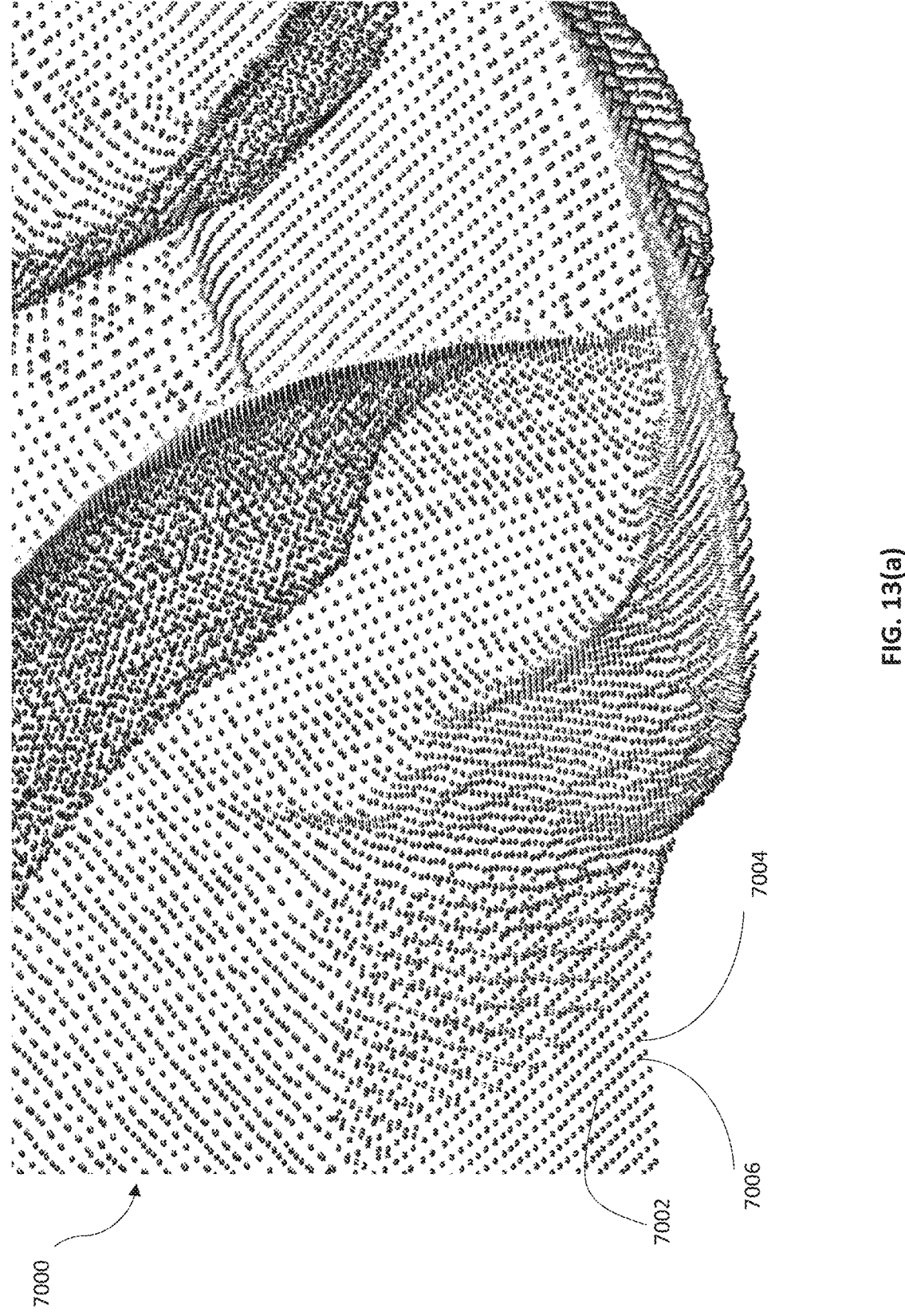
FIG. 13(*a*) is a perspective view of a point cloud.

FIG. 13(a) shows an example of a generated point cloud viewable on a display in some embodiments by the computer-implemented method. Point cloud 7000 includes generated digital surface points such as digital surface point 7002 at every position of the selected iso-value of density in virtual 3D space.

Figure 13B:
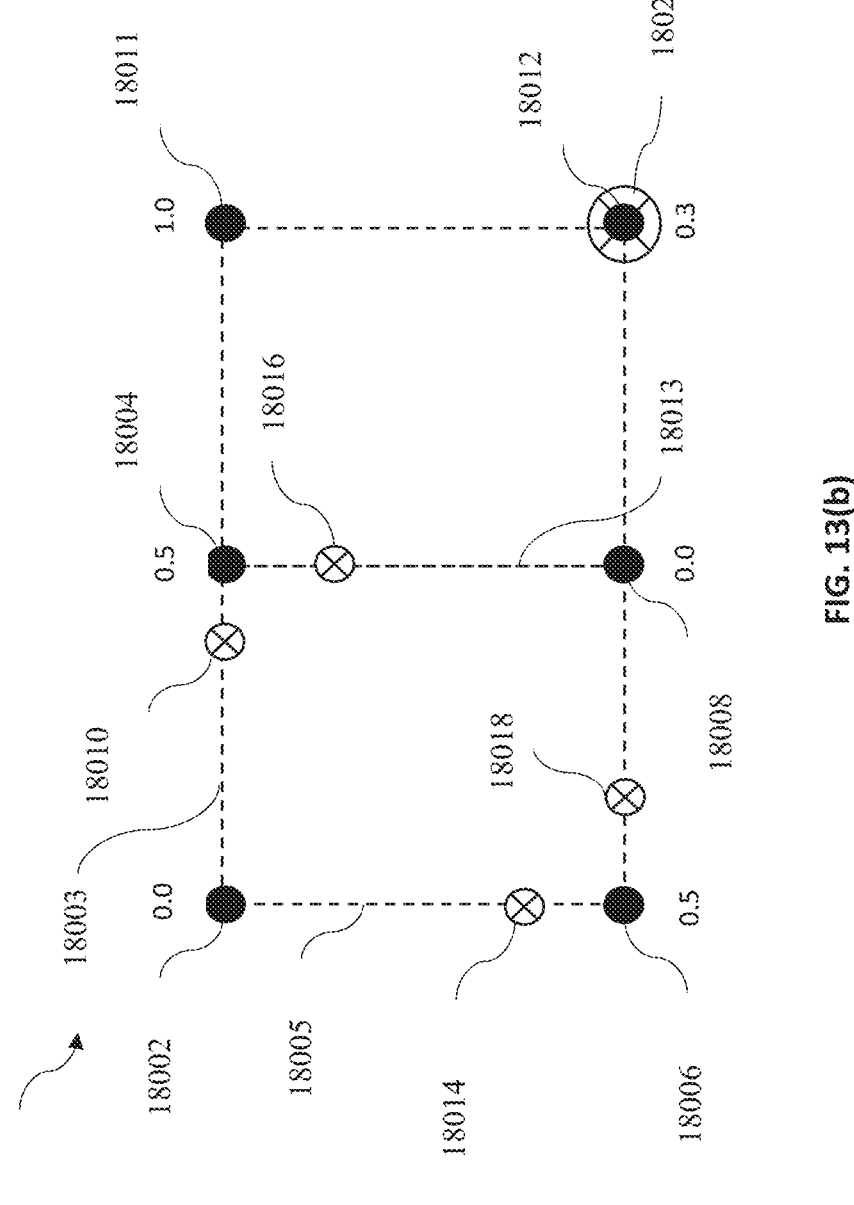

FIG. 13(b) illustrates an example of the computer-implemented method automatically generating digital surface points at particular positions in virtual 3D pace to generate a point cloud in some embodiments based on voxel positions in the volumetric density file. The figure illustrates a portion of a 3D volumetric density file depicted for simplicity in 2 dimensions. In the example, voxels 18002, 18004, 18006, 18008, 18011, and 18012 from the volumetric density file represent different density values of the CT scanned material in the volumetric density file. For example, voxels 18002 and 18008 indicate materials at their positions have a density of 0. This can, for example, represent air. In the example, voxels 18004 and 18006 indicate the material at their respective positions has a density of 0.5, voxel 18011, indicates material density at its position is 1.0, and voxel 18012 indicates a material density of 0.3 at its position.

In some embodiments of a computer-implemented method, the volumetric density file containing voxels is loaded, and each voxel is evaluated against a selectable iso-value of density. If the selected iso-value of density matches the density value at a voxel, then the computer-implemented method can generate one or more digital surface points and arrange the one or more digital surface points in the point cloud at a position that corresponds to or is in the neighborhood of the position of the voxel in the volumetric density file. In some embodiments of the computer-implemented method, if the selected iso-value of density falls between the density value of voxels, then the computer-implemented method can generate one or more digital surface points in the point cloud at position(s) corresponding to position(s) between the voxels along an edge connecting the voxels as further discussed below.

In the example figure, a selected iso-value of density of 0.3, for example, would fall between voxel 18002, which has a density of 0, and voxel 18004, which has a density of 0.5. One or more digital surface points can be generated at a position in the point cloud corresponding to a position 18010 in the volumetric density file between voxel 18002 and voxel 18004 along a voxel edge 18003. One or more digital surface points can also be generated and placed at a position in the point cloud corresponding to a position 18014 in the volumetric density file between voxel 18002 and voxel 18006 along their voxel edge 18005 since the selected iso-value of density (0.3) in the example also falls between the densities at voxels 18002 and 18006. In the example, no digital surface points are generated and placed at a position in the point cloud corresponding to the position in the volumetric density file between voxels 18004 and 18011 because the selected iso-value of density 0.3 does not fall between the values of voxel 18004 (0.5) and 18011 (1.0). One or more digital surface points can also be generated and placed at a position in the point cloud corresponding to a position 18016 in the volumetric density file between voxel 18004 and voxel 18008 along their voxel edge 18013 since the selected iso-value of density (0.3) in the example also falls between the densities at voxels 18004 and 18008. Since voxel 18012 has a density value matching the selected iso-value of density of 0.3, a digital surface point can be generated in the point cloud at the same corresponding position 18020 of the voxel 18012.

In some embodiments of the computer-implemented method, digital surface points that are generated for an iso-density value falling between voxels can be proportionately spaced in the point cloud between corresponding positions of voxels for which they are generated. For example, a selected iso-value of density of 0.3 is closer to density 0.5 of voxel 18006 than to density 0 of voxel 18002. The computer-implemented system can, for example, generate a digital surface point at position 18014 in the point cloud since position 18014 is proportionately closer to the corresponding position of voxel 18006 than to the position of voxel 18002 in the volumetric density file. A digital surface point is generated at position 18018 in the point cloud for an iso-density value of 0.3 since position 18018 is proportionally closer to the corresponding position of voxel 18006 with density 0.5 than the position of voxel 18008 with density 0. A digital surface point is generated at position 18010 in the point cloud for a selected iso-density value of 0.3 since position 18010 is proportionally closer to the corresponding position of voxel 18004 with density 0.5 than the position of voxel 18002 with density 0. A digital surface point is generated at position 18016 in the point cloud for a selected iso-density value of 0.3 since position 18016 is proportionally closer to the corresponding position of voxel 18004 with density 0.5 than the position of voxel 18008 with density 0, for example.

In some embodiments, the computer-implemented method can evaluate every voxel in the volumetric density file against the user-selected iso-value of density and generate one or more digital surface points in the point cloud as disclosed herein until no more voxels remain for evaluation in the volumetric density file.

Figure 13C:
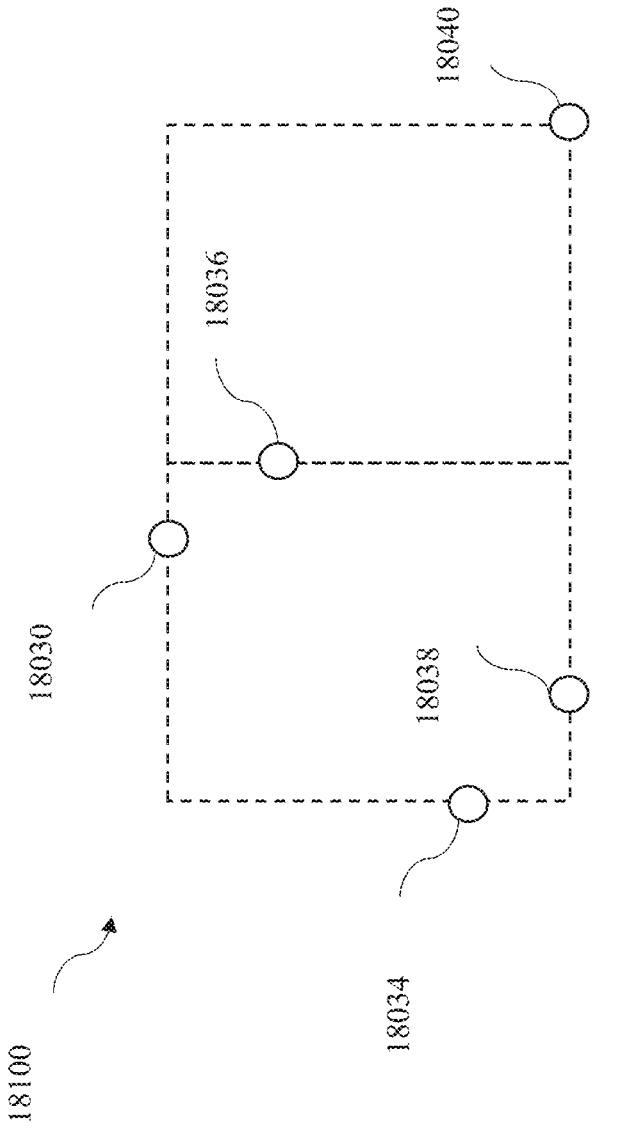

FIG. 13(c) illustrates an example of a 2D depiction 18100 of a 3D generated point cloud 7000 with digital surface points 18030, 18034, 18036, 18038, and 18040 generated at positions in the point cloud corresponding to positions 18010, 18014, 18016, 18018, and 18020, respectively in the volumetric density file 18000 from FIG. 13(b) for an iso-value density of 0.3. As illustrated in the figure, only the digital surface points generated for a selected iso-value from the volumetric data file are included in the point cloud by the computer-implemented method. The computer-implemented method can save the generated digital point cloud 7000 to storage media. The computer-implemented method can in some embodiments, display and provide the generated point cloud 7000 to a user to view and/or manipulate.

Point Cloud Sampling/Reduction

In some embodiments the computer-implemented method reduces the number of digital surface points in the point cloud 7000 from FIG. 13(a) through sampling, such as, for example, by selecting a subset of the digital surface points from the point cloud 7000 to provide a reduced point cloud. Selecting the subset of digital surface points from the point cloud 7000 can reduce the dataset size and complexity and simplify data structures and processing. In some embodiments, the computer-implemented method can automatically reduce the point cloud. In some embodiments, the point cloud can be received by the computer-implemented method.

In some embodiments of the computer-implemented method, point cloud 7000 can be reduced by selecting a desired level of distance between two or more digital surface points. In some embodiments, of the computer-implemented method, point cloud 7000 can be reduced by setting a minimum distance between digital surface points in the point cloud 7000. For example, during reduction of point cloud 7000, digital surface points can be specified not to be closer than a user-selectable distance. In some embodiments of the computer-implemented method, a minimum distance between points can be between 100 microns to 200 microns or less, for example. The minimum distance between points can be a user selectable value. The minimum distance between points can be initially set and then automatically applied during every surface selection thereafter, or can be selected on a per scan basis.

Figure 14A:
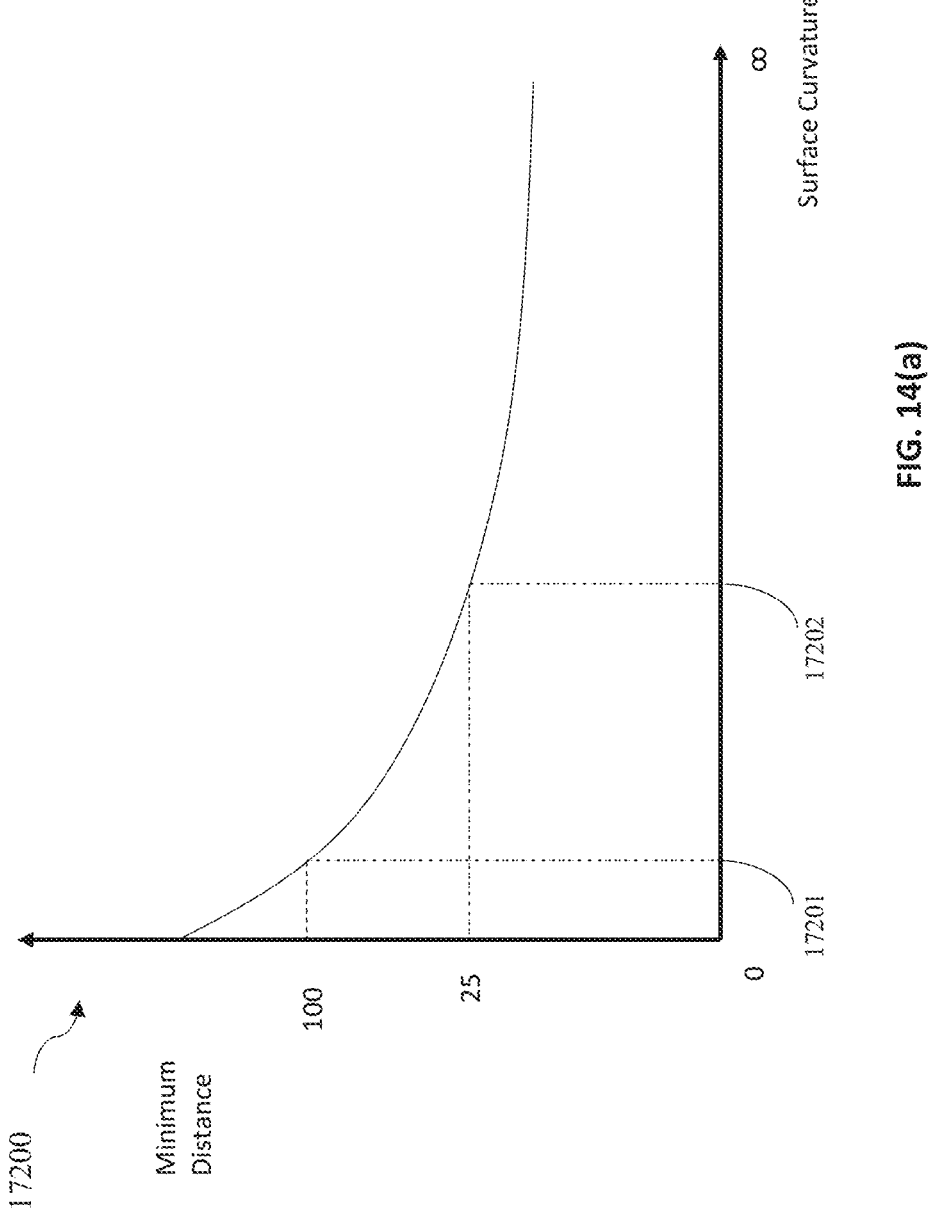
FIG. 14(*a*) is a graph illustrating a user selectable relationship between surface curvature and minimum distance.

In some embodiments of the computer-implemented method, the minimum distance can optionally be specified by a user to be a continuous function of surface curvature as illustrated in FIG. 14(a). In some embodiments, the computer-implemented method can load the point cloud and determine curvature by finding all the points in the neighborhood of a radius around each digital surface point, fitting a quadratic surface to the points in the neighborhood, and determining the module of mean curvature of that surface, for example. The computer-implemented method can be repeated for all points in the point cloud in some embodiments, for example.

In some embodiments, a computer-implemented method can alternatively determine curvature by loading a generated point cloud and for each digital surface point, finding all the points in the neighborhood of the radius around the digital surface point. The computer-implemented method can then determine a 3×3 covariance matrix for the coordinates of the points in the neighborhood. Next, the computer-implemented method can find all 3 eigenvalues of the covariance matrix, and finally approximate the curvature from the eigenvalues in some embodiments, e.g. minimal eigenvalue divided by the sum of eigenvalues or a monotone function of that fraction. This computer-implemented embodiment can account for zero mean curvatures for non-planar regions and can therefore be preferable in some embodiments, for example. The computer-implemented method can be repeated for all points in the point cloud in some embodiments, for example.

In some embodiments, the radius of either method of determining curvature can be up to and including 60 digital surface points on average in the neighborhood of the digital surface point in the point cloud being evaluated, and can be a user selectable value. In some embodiments, the number of digital surface points can be greater or less than 60. A selection of a smaller number of points and smaller radius can lead to faster computations, while selecting a larger number of points and larger radius can provide a more precise curvature estimation. The computer-implemented method can be repeated for all points in the point cloud, for example.

Once surface curvature is determined, the computer-implemented method can determine the minimum distance based on the particular amount of surface curvature. For example, FIG. 14(a) is a graph 17200 depicting a user-selectable relationship between surface curvature and minimum distance between digital surface points as an example. The computer-implemented method can determine the amount of surface curvature and then obtain the minimum distance between digital surface points based on the user selected relationship. In the example shown in FIG. 14(a), a digital surface region having a surface curvature value at 17201 can return a minimum distance of 100 microns between points for the digital surface region, for example. A greater surface curvature value at 17202 can return a minimum distance of 25 microns between points for the digital surface region, for example. In some embodiments, any digital surface points falling within the minimum distance of a digital surface point can be eliminated from the point cloud by the computer-implemented method. The computer-implemented method can be repeated for all points in the point cloud, for example.

In some embodiments of the computer-implemented method, minimum distance between points can be defined discretely rather than as a continuous function of surface curvature. For example, the minimum distance between digital surface points can be specified based on a curvature threshold of the digital surface. For example, curved digital surfaces having a surface curvature above a particular user-selectable value can have a user-selectable minimum distance between digital surface points that is lower than that of digital surface regions having a surface curvature below the threshold user-selectable curvature value.

In some embodiments of the computer-implemented method, the minimum distance between points can be reduced up to ¼ of the original distance, for example, based on curvature. For example, where the distance between digital surface points may be set to 100 microns, it can be reduced by the user to 25 microns between digital surface points, thereby increasing the number of digital surface points on the surface curvature. In some embodiments of the computer-implemented method, the minimum distance between digital surface points on a digital surface curvature can be a user selectable value, the distance can be initially set and then automatically applied during surface selection, and/or the minimum distance between digital surface points along one or more curvature surfaces may be set independently with respect to other surfaces.

In some embodiments, if the digital surface point does not fall within the sampling/reduction criterion, then the digital surface point is eliminated from the point cloud. For example, if a minimum distance between digital points in the cloud is set and one or more neighboring digital surface point(s) fall within the minimum distance between digital surface points, then the computer-implemented method can eliminate the one or more digital surface points from the point cloud. If, however, one or more neighboring digital surface points fall outside of the minimum distance, then the one or more neighboring digital surface points are retained in the point cloud.

As an example, the computer-implemented method can load a point cloud and for each digital surface point determine one or more neighboring digital surface points within a radius from a generated point cloud. In some embodiments, the radius in some embodiments can be up to and including 60 digital surface points in the neighborhood of the digital surface point in the point cloud being evaluated, and can be a user selectable value. In some embodiments, the number of digital surface points can be greater or less than 60. An amount of curvature for the first and one or more neighboring digital surface points can be determined by the computer-implemented method as discussed previously. In some embodiments, the amount of surface curvature can be zero, or close to zero, indicating a flatter digital surface. In some embodiments, the amount of curvature can be greater than zero. In some embodiments, the computer-implemented method can determine a minimum distance between each digital surface point and the one or more neighboring digital surface points based on the amount of curvature between them. If the minimum distance between digital surface points is specified, then the computer-implemented method can determine whether the neighboring digital surface point(s) fall(s) within the specified minimum distance between digital surface points. If any of the one or more neighboring digital surface point falls within the minimum distance specified, then those neighboring digital surface points can be eliminated from the point cloud by the computer-implemented method. If the neighboring digital surface point falls outside of the minimum distance specified for surface curvature or no minimum distance is specified, then the one or more neighboring digital surface point(s) is/are retained in the point cloud.

In some embodiments of the computer-implemented method, if the first and neighboring digital surface point are on a curved digital surface based on a threshold curvature value, then the computer-implemented method can determine whether a minimum distance between digital surface points is specified. If the minimum distance between digital surface points is specified, then the computer-implemented method can determine whether the neighboring digital surface point falls within the specified minimum distance between digital surface points. If the neighboring digital surface point falls within the minimum distance specified, then the computer-implemented method can eliminate it from the point cloud. If the neighboring digital surface point falls outside of the minimum distance or the minimum distance is not specified for curved surfaces, then the computer-implemented method can retain it in the point cloud. If the computer-implemented method determines that the first and neighboring digital surface points are not on a surface curvature, then the computer-implemented method can determine whether the minimum distance between digital surface points for non-curved surfaces (i.e. flatter surfaces or surfaces whose curvature is below the threshold value for curvature) is specified. If the minimum distance between digital surface points is specified, then the computer-implemented method compares whether the neighboring digital surface point falls within the minimum distance between digital surface points for flatter surfaces. If the neighboring digital surface point falls within the minimum distance, then the computer-implemented method eliminates it from the point cloud. If the neighboring digital surface point falls outside of the minimum distance or a minimum distance between digital surface points for flatter surfaces is not specified, then the computer-implemented method retains the neighboring digital surface point in the point cloud.

Figure 14B:
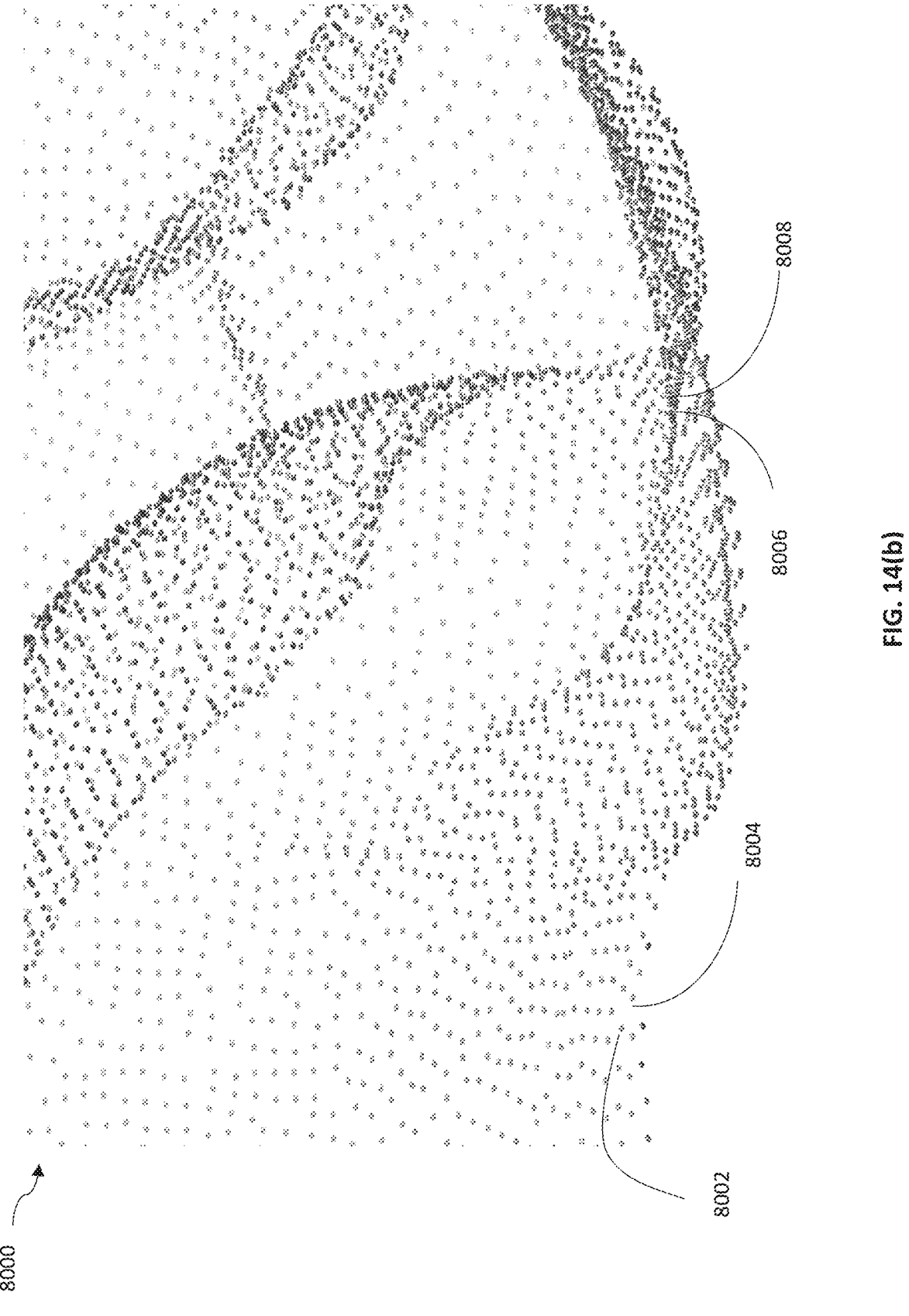

FIG. 14(b) illustrates a post-sampling reduced point cloud 8000 of point cloud 7000 having fewer digital surface points than the point cloud 7000 from FIG. 13(a). As shown in the example of FIG. 14(b), digital surface points 8002 and 8004 are spaced further apart than digital surface points 7004 and 7006 from FIG. 13(a), and intermediate digital surface points are not present in the post-sampling reduced point cloud 8000 of FIG. 14(b). Also illustrated in the example of reduced point cloud 8000 are digital surface points 8006 and 8008 located on a curved surface. As discussed previously, this arrangement of digital surface points and the number of digital surface points on the curved surface in the reduced point cloud 8000 may result from either setting a minimum distance between digital surface points and/or setting a different minimum distance between digital surface points on curved surfaces versus non-curved or reduced-curvature/flatter surfaces in some embodiments of the computer-implemented method.

One advantage of sampling the point cloud prior to generating the digital surface mesh is to improve speed and reduce the data set and data structure complexity of any subsequent triangulation step by reducing the number of digital surface points to be triangulated. This can, for example, improve processing speed and reduce the amount of storage necessary to process CT scans. This can improve the accuracy and efficiency of generating the digital surface mesh, as described below.

Triangulation

In some embodiments, the computer-implemented method performs triangulation on a point cloud to generate a digital surface mesh. In some embodiments of the computer-implemented method, triangulation can be performed on the reduced point cloud 8000 to create digital surface mesh 2012 shown in FIG. 11, for example. This triangulation can in some embodiments of the computer-implemented method utilize Delaunay triangulation known in the art to create digital surface mesh 2012. The digital surface mesh 2012, however generated, is an interconnected network of triangles defining part or all of a surface of the physical dental impression 2000. In some embodiments, the computer-implemented method performs triangulation of the reduced point cloud automatically. In some embodiments, the computer-implemented method can receive the point cloud.

Figure 15:
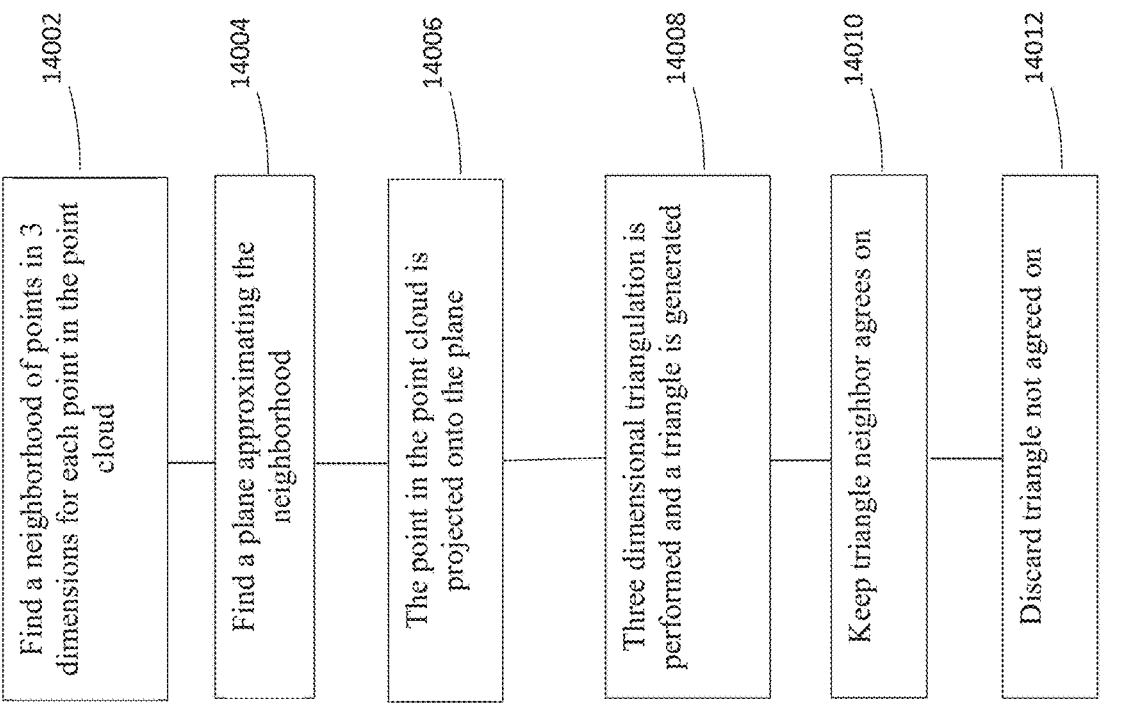
FIG. 15 illustrates a method of triangulation in some embodiments.

In some embodiments of the computer-implemented method, as illustrated in FIG. 15, triangulation can include finding a neighborhood of digital surface points in three dimensions for each digital surface point in the reduced point cloud 8000 at 14002. In some embodiments of the computer-implemented method, the neighborhood of digital surface points can be a user selectable radius up to and including 20 points. In some embodiments of the computer-implemented method, the number of digital surface points can be greater or less than 20. A plane approximating the neighborhood is found at 14004 by the computer-implemented method. The digital surface point in the point cloud 8000 is then projected onto the plane at 14006 to determine the ordering of neighboring points by the computer-implemented method. Three dimensional triangulation is performed and a triangle is generated at 14008 by the computer-implemented method. If the neighborhood agrees the triangle should be kept, then it is retained at 14010 by the computer-implemented method. Otherwise, the triangle is discarded at 14012 by the computer-implemented method. Triangulation of the reduced point cloud 8000 can produce a digital surface mesh with non-degenerate triangles. In some embodiments, each triangle can be close to an equilateral triangle, thereby generating an improved digital surface mesh. The computer-implemented method can be repeated for each point in the point cloud.

Figure 16:
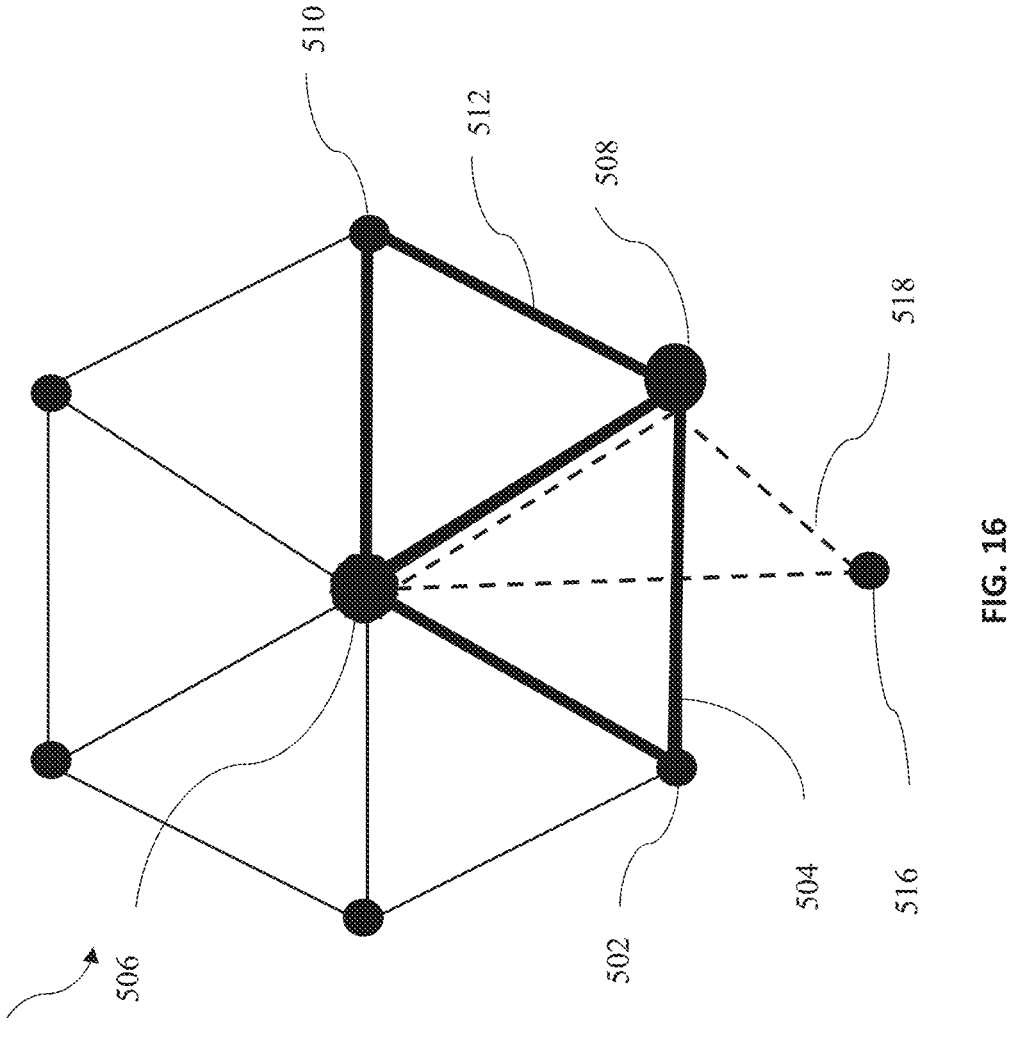
FIG. 16 is a perspective view of an example of triangulation of a point cloud.

FIG. 16 illustrates one example of triangulation in some embodiments of the computer-implemented method. Reduced point cloud 500 includes digital surface points 502, 506, 508, 510, and 516, for example, among other digital surface points. During triangulation in some embodiments of the computer-implemented method, a digital surface point is chosen and connected with its neighbors to create triangles that form a digital surface mesh. For example, digital surface point 506 is chosen and connected with its neighboring digital surface points 502 and 508 to form triangle 504. Digital surface point 506 is also connected with neighborhood digital surface points 508 and 510 to create triangle 512. Other triangles are similarly created by connecting other neighborhood digital surface points to digital surface point 506 as shown in FIG. 16. Once triangles are generated for one digital surface point, a new digital surface point is chosen, and triangles connecting the new digital surface point to its surrounding digital surface points are generated in some embodiments of the computer-implemented method. In the example shown in FIG. 16, new neighboring digital surface point 508 is chosen, for example, and connected to digital surface points 506 and 510 to create triangle 512. New digital surface point 508 is also, for example, connected to digital surface points 506 and 502 to create triangle 504. These triangles 504 and 512 created with chosen digital surface point 508 overlap with the triangles created when digital surface point 506 was the chosen digital surface point. Since the chosen digital surface points 506 and 508 agree on these triangles, the triangles are retained. Chosen digital surface point 508 also connects with its neighborhood digital surface points 506 and 516 to create triangle 518. Since triangle 518 was not generated when 506 was the chosen digital surface point, chosen digital surface points 506 and 508 do not agree on this triangle. The triangle can, in some embodiments of the computer-implemented method, be dropped and no digital surface mesh is created with triangle 518. The computer-implemented method can be repeated for each point in the point cloud.

Figure 17:
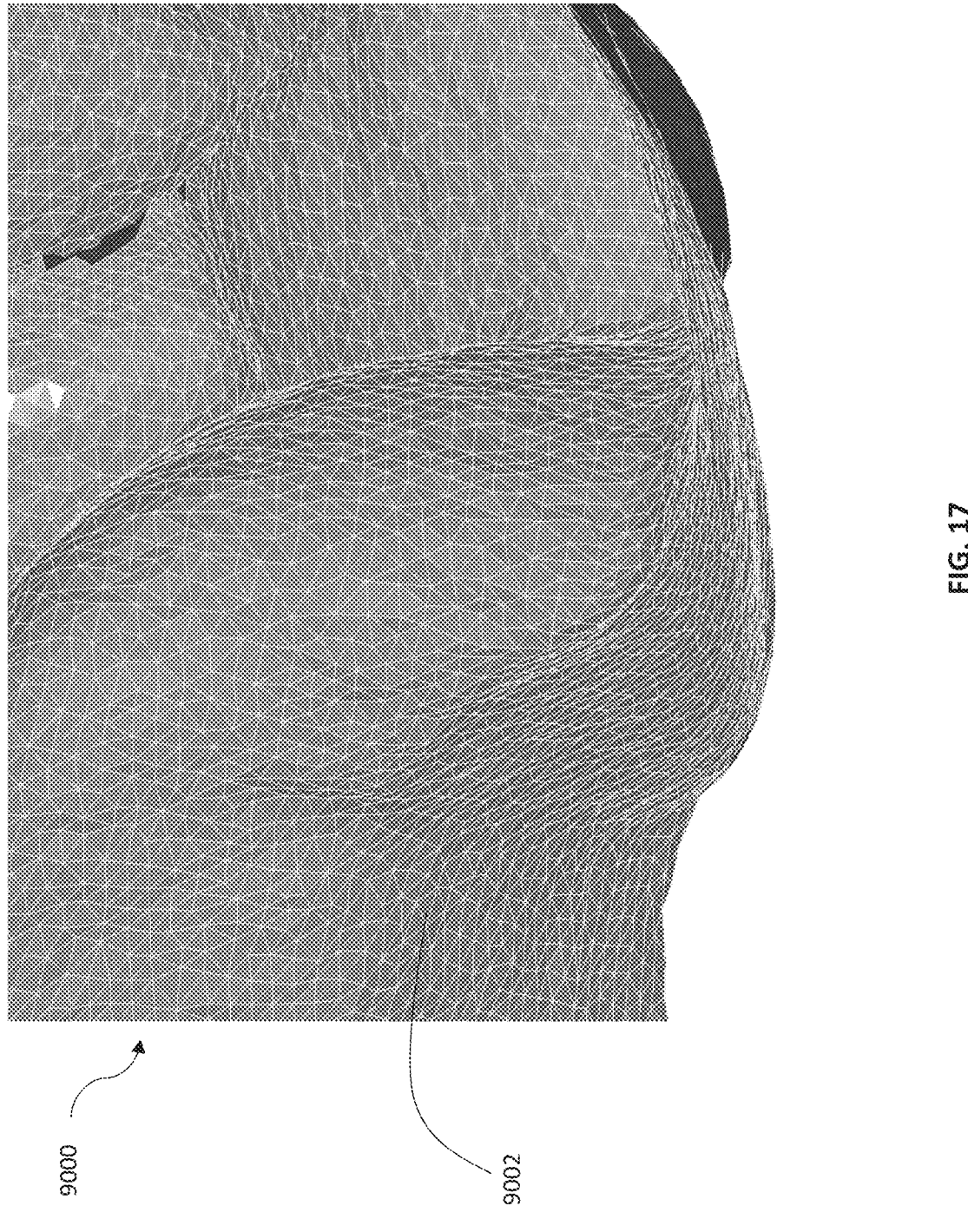
FIG. 17 is a perspective view of a digital model illustrating a triangulated digital surface mesh.
Figure 18A:
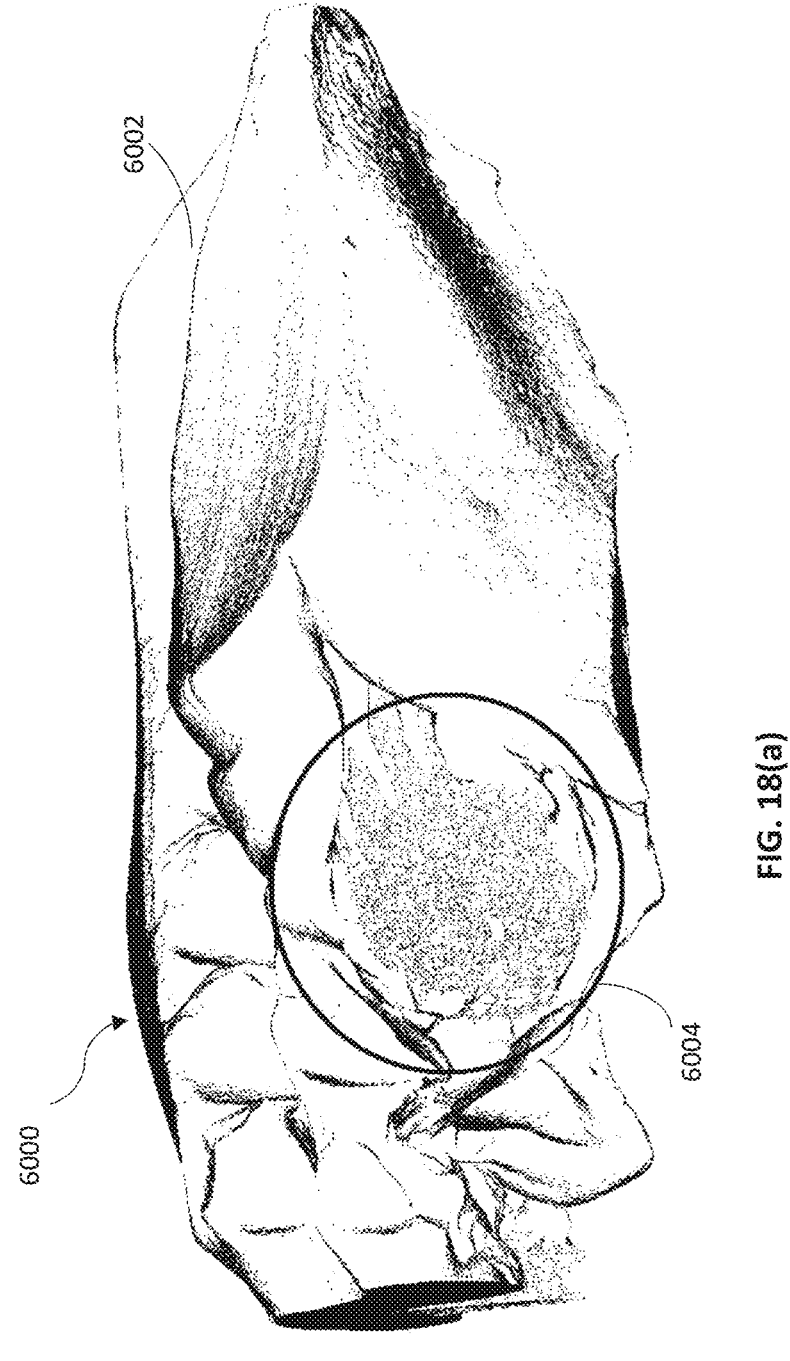
FIG. 18(*a*) is an orthogonal view of a digital model containing a noisy region.
Figure 18B:
Figure 18C:
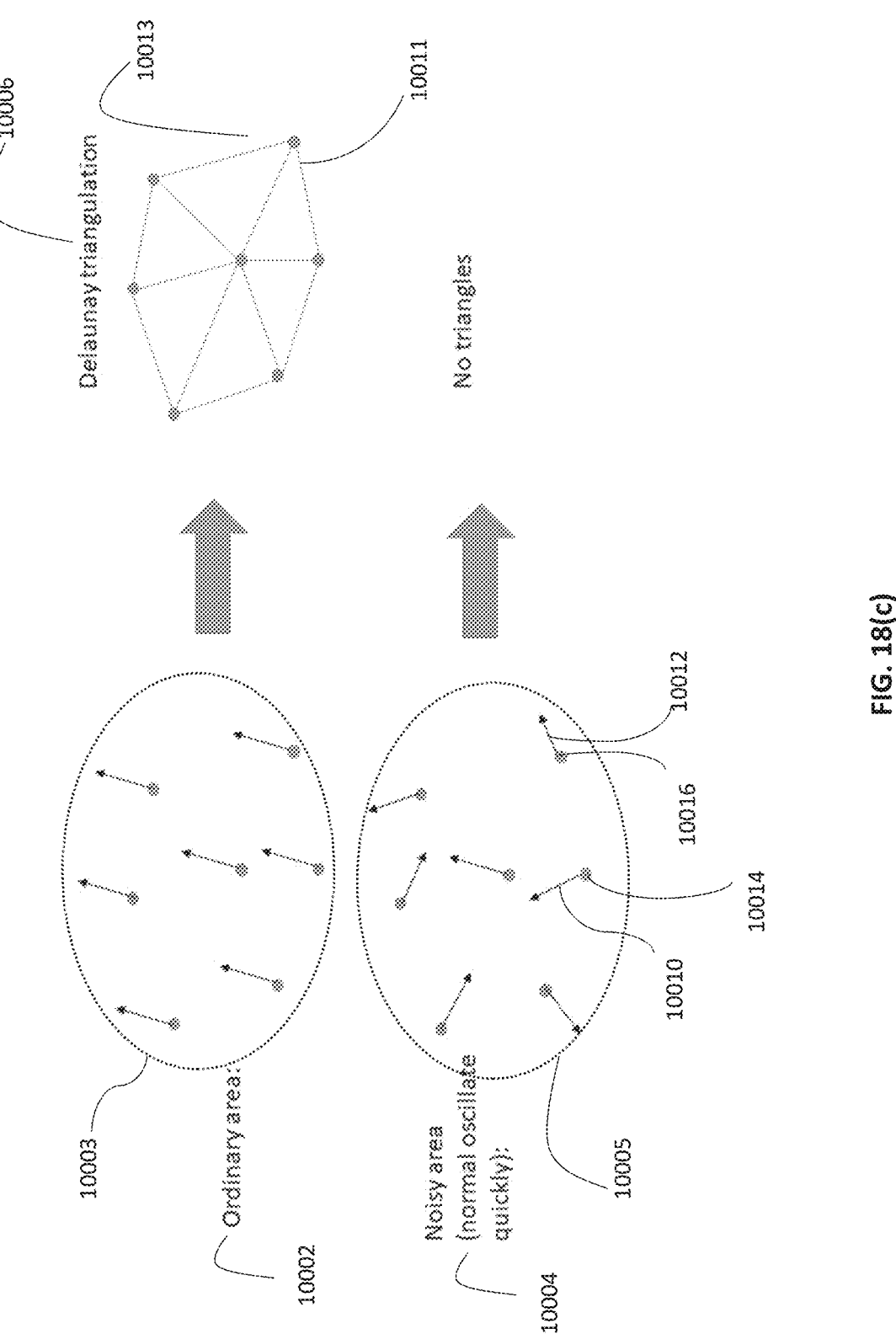
Figure 18D:
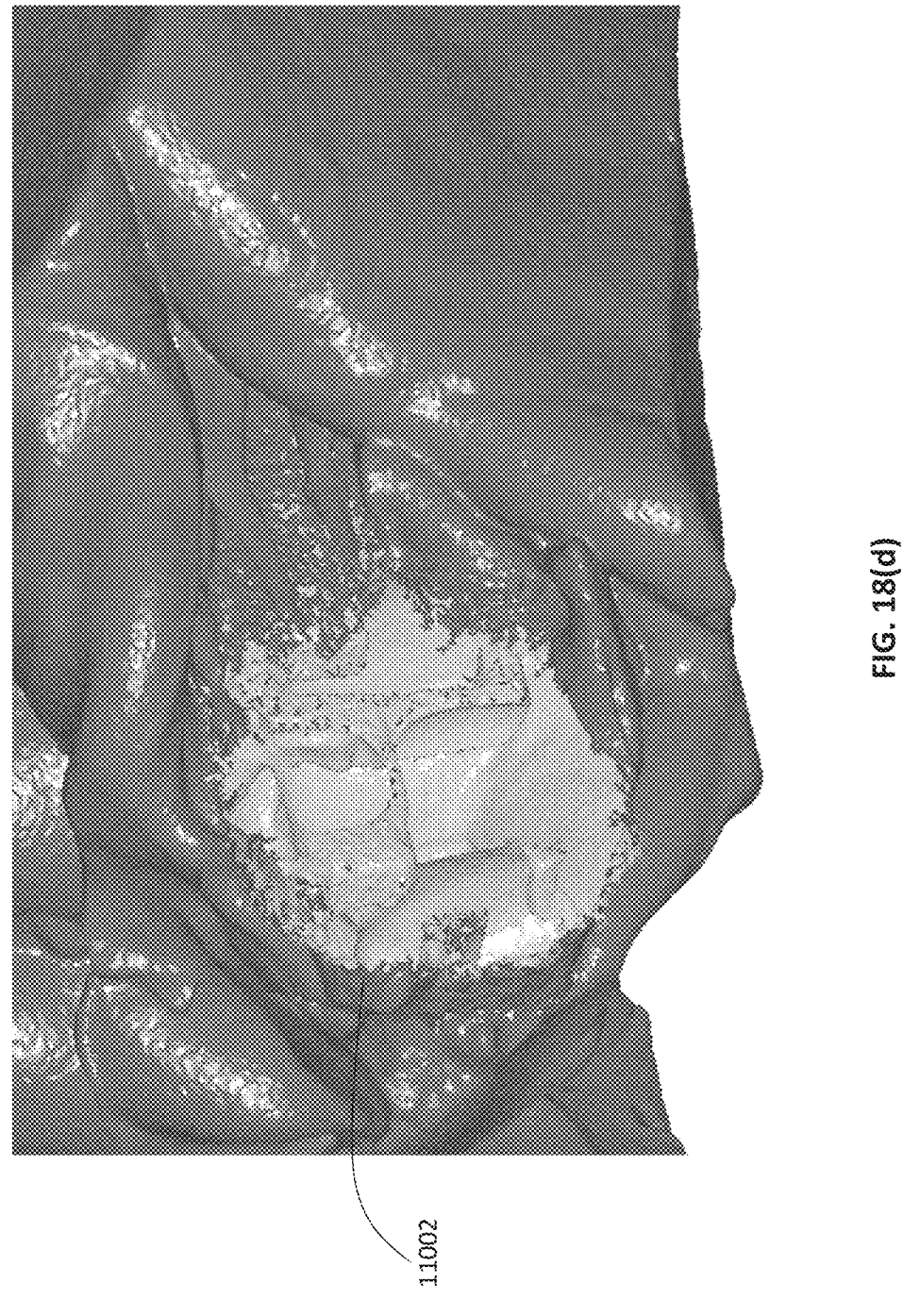

FIG. 17 illustrates an example of a reduced point cloud 9000 that has been triangulated to create a digital surface mesh. Triangulation of the reduced point cloud 9000 as described in this disclosure can generate a digital surface mesh of non-degenerate triangles 9002 in some embodiments of the computer-implemented method. Each of the triangles—such as triangle 9002—are close to equilateral.

Noisy Regions

In some embodiments, the computer-implemented method excludes noisy regions of the point cloud from triangulation. The point cloud can be received by the computer-implemented system in some embodiments. Some CT scans have regions with surfaces having significant topological variation/fluctuation/oscillation within a small area. This can occur, for example, when a selected iso-value of density is close to the density of another material, such as an impression tray handle material. For example, if an iso-value selected is close to that of a handle, the surface near the handle may include significant topological variation due to its adjacency to the handle. These surfaces can produce one or more noisy areas/regions such as noisy region 6004 illustrated in FIG. 18(*a*). A close up of noisy region 6004 illustrated in FIG. 18(*b*) shows many triangles 6006 within a small area. The large number of triangles 6006 reflects the large number of fluctuations or rapid oscillations in the topography of the digital surface mesh, and contribute to an increased dataset. In some embodiments of the computer-implemented method, one or more noisy areas can be determined by measuring the change in direction of the normals between adjacent or neighborhood digital surface points as illustrated in FIG. 18(*c*).

In some embodiments of the computer-implemented method, noisy areas can be determined as digital surface points whose normals vary by a user selectable value. This value may be initially set and then automatically applied during surface selection by the computer-implemented method. In some embodiments of the computer-implemented method, for example, if normals between adjacent or neighborhood digital surface points vary by 75 degrees, then the variation can signify rapid normal oscillation and therefore a noisy region and the digital surface points whose normals vary by more than the user-selected value of normal fluctuation can be excluded by the computer-implemented method from triangulation. For example, normal 10010 and normal 10012 vary by more than 75 degrees. Therefore digital surface points 10014 and 10016 belonging to those normals, respectively, can be excluded from triangulation by the computer-implemented method. Although 75 degrees is provided as an example of a threshold indicating a "noisy" region, any value can be selected and set by a user, computer program, or other input. In some embodiments, the computer-implemented method automatically eliminates noisy regions from the point cloud.

In some embodiments of the computer-implemented method, the noisy region 6004 can be excluded from triangulation of the point cloud. For example, FIG. 18(*c*) illustrates an ordinary region 10002 containing a set of ordinary digital surface points 10003 all having normals in substantially the same direction as denoted by the substantially parallel arrows pointing the same direction in the figure. Since the normal of each digital surface point is orthogonal to a digital surface, the set of ordinary digital surface points 10003 reflect a substantially topologically non-variant (or low oscillation) digital surface. During triangulation—for example Delaunay triangulation 10006—the set of ordinary digital surface points 10003 from the ordinary region 10002 is triangulated by the computer-implemented method to form, for example, triangles 10011 defining digital surface mesh 10013. Also illustrated in FIG. 18(*c*) is a noisy region 10004 containing a set of noisy digital surface points 10005 with normals in substantially different direction as denoted by the substantially nonparallel arrows pointing in different directions in the figure. Since the normal of each digital surface point is orthogonal to a digital surface, the set of noisy digital surface points 10005 define a substantially topologically variant (or high oscillation) digital surface. These noisy digital surface points 10005 are not selected for subsequent triangulation by the computer-implemented method. Thus the noisy digital surface points 10005 with their quickly/rapidly oscillating normals (or highly variant normals within a small region) are not triangulated by the computer-implemented method. As shown in FIG. 18(*d*), this creates a digital surface mesh hole region 11002 for the noisy region 6004. The computer-implemented method can be repeated for each point in the point cloud.

One advantage of excluding triangulation of one or more noisy regions is a reduced dataset and therefore improved processing speed and reduced complexity. One advantage of generating a point cloud from the CT scan, sampling the cloud, and performing triangulation is improved speed. For example, a digital surface mesh using the point cloud method disclosed herein can take 15 seconds to render, compared to 10 minutes using conventional surface selection techniques.

In some embodiments, selecting the iso density level, selecting the subset of digital surface points from the plurality of digital surface points, or setting the threshold for noisy region exclusion occur automatically for one or more CT scanned images. In some embodiments, one or more operators can manually select(s) the iso density level, select (s) the subset of digital surface points from the plurality of digital surface points for one or more CT scanned images, and/or set the threshold for noisy region exclusion.

Surface Optimization

In some embodiments, the computer-implemented method performs surface optimization on zero or more digital surface points of a digital surface to generate an optimized digital surface. The digital surface can be generated as described in the present disclosure, or by any digital surface technique known in the art, including but not limited to marching cubes, etc. In some embodiments, the computer-implemented method receives the digital surface or a digital surface mesh. The digital surface mesh can include digital surface triangles connecting the digital surface points to form a digital surface mesh. In some embodiments, the digital surface points of the digital surface mesh are vertices of digital surface triangles.

For the digital surface generated as described in the present disclosure, some embodiments of the computer-implemented method include selecting a criteria of digital surface optimization on the subset of digital surface points and moving one or more digital surface points to satisfy the criteria of optimum digital surface selection. In some embodiments, this can include the computer-implemented method moving one or more digital surface points to a maximum density derivative along the normal of the digital surface point in the generated point cloud, the sampled/ reduced point cloud, the triangulated/surface meshed point cloud, and/or the hole patched point cloud. In some embodiments, surface optimization by the computer-implemented method will not move one or more digital surface points if the one or more digital surface points are already positioned at the maximum of density derivative. In some embodiments, the computer-implemented method automatically performs surface optimization.

Figure 19A:
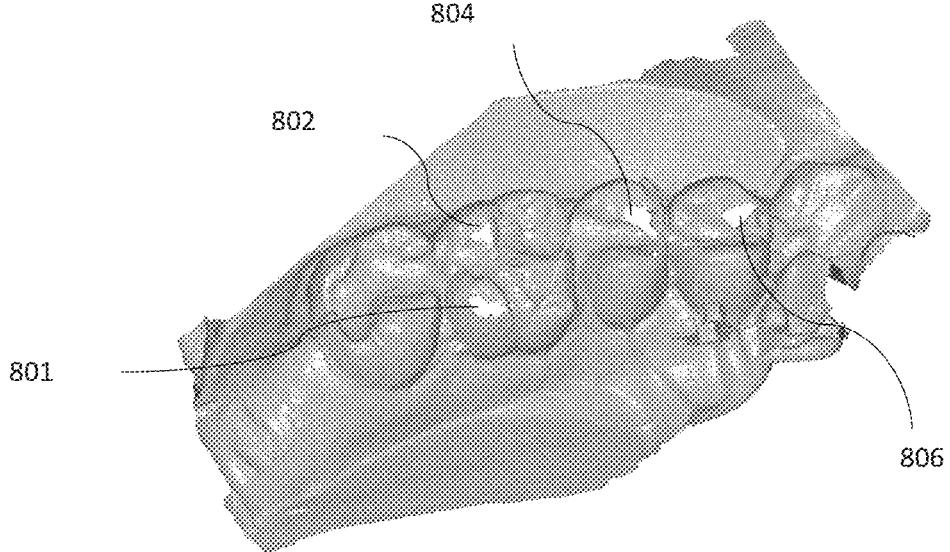
FIG. 19(*a*) is a perspective view of a digital surface with holes.
Figure 19B:
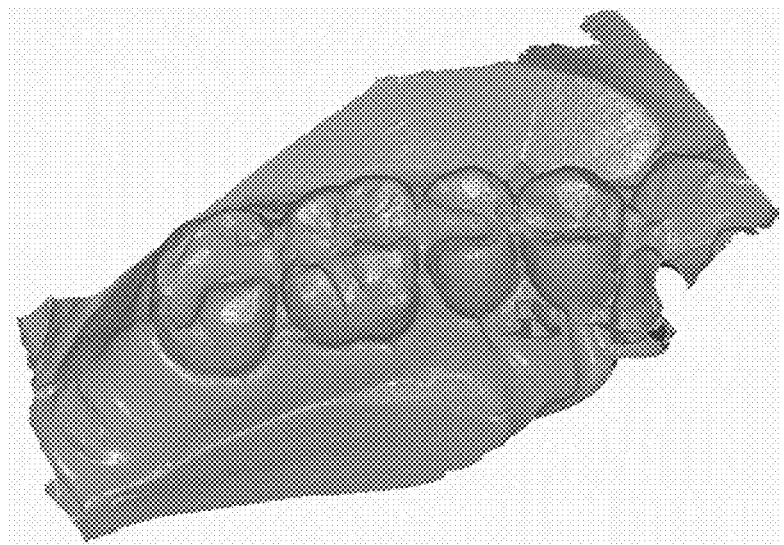

In some embodiments of the computer-implemented method, one or more portions of the digital surface or digital surface mesh that have "holes" or missing digital surface mesh areas can optionally be filled or patched using a variety of techniques known in the art. Digital surface mesh holes or tunnels can arise where dental impression material is thin or nonexistent, or as an artifact of surface selection. The digital surface mesh holes can be optionally initially "filled" with a digital surface patch. As illustrated in the example of FIG. 19(*a*) digital surface mesh holes 801, 802, 804, and 806 on the digital surface mesh can be optionally patched as necessary in one embodiment. The digital surface patching can involve a variety of digital surface patching techniques known in the art. Some of these techniques are described in A COMPARISON OF HOLE-FILLING METHODS IN 3D, Int. J. Appl. Math. Comput. Sci., 2016, Vol. 26, No. 4, 85-903. In one embodiment, a hole filler and surface patching technique by GeoMagic Design X can be used.

In some embodiments of the computer-implemented method, holes can be optionally patched by first identifying regions where no digital surface exists. Next, holes can be optionally patched using any hole filler technique known in the art. FIG. 19(*b*) illustrates a digital surface with patched holes.

Figure 20A:
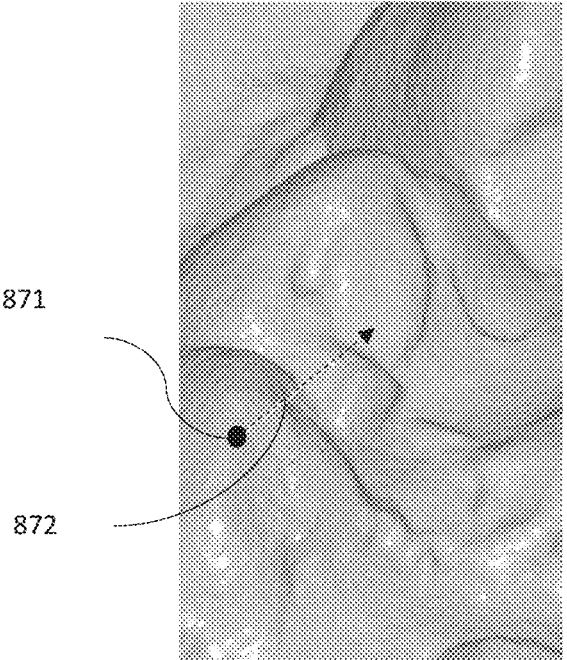
FIG. 20(*a*) is a perspective view of a digital surface point with a normal.
Figure 20B:
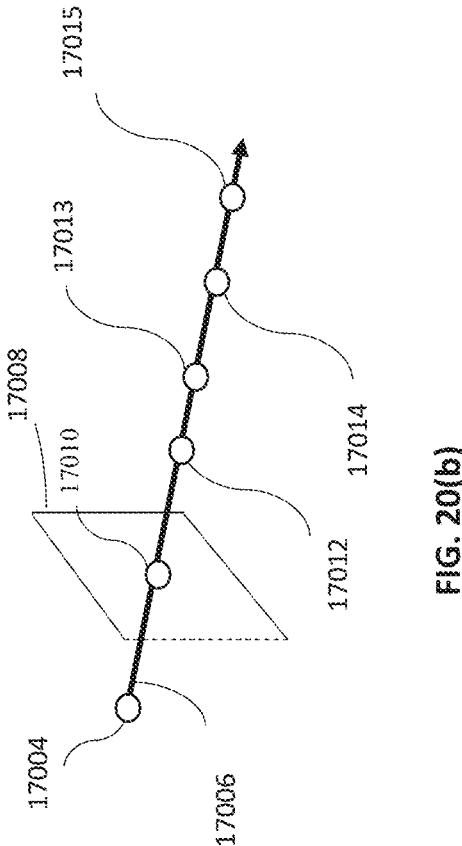
Figure 20C:
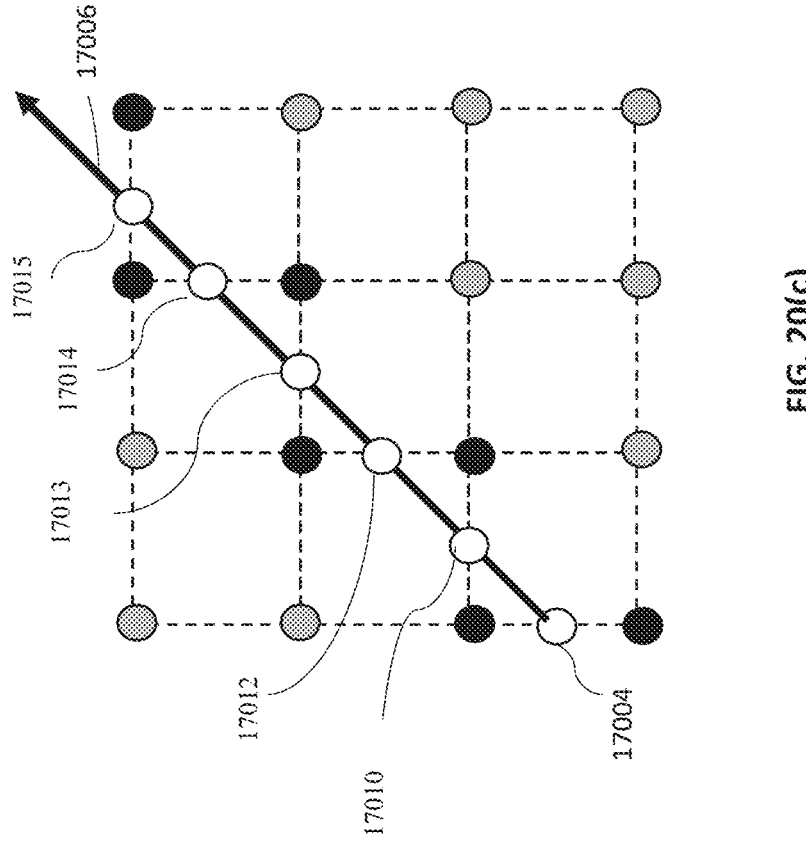

In some embodiments of the computer-implemented method, the criteria of optimum digital surface selection includes a maximum of density derivative along a normal of each digital surface point of the digital surface points. The computer-implemented method can load one or more digital surface points from the point cloud or digital surface mesh and move the one or more digital surface points to a maximum of density derivative along the normal of the digital surface point. FIG. 20(*a*) illustrates a digital surface point 871 having a normal 872, for example. The maximum density derivative can indicate a change in material density which can occur at a boundary between materials, and therefore indicate a surface of the material. As illustrated in the example shown in FIG. 20(*b*), a density point 17004 of a volumetric density file has a normal 17006 to a digital surface 17008. The normal can indicate the density gradient with respect to the density point 17004. In this example, the iso-value of density selected may have an initially generated or sampled a digital surface point in a point cloud at the corresponding position of density point 17004. The normal 17006 of density point 17004 can extend through density points 17010, 17012, 17013, 17014, and 17015, which can be density positions along a normal of density point 17004, for example. FIG. 20(*c*) illustrates a volumetric density file with a density point 17004 and its normal 17006 in an example 3D volumetric density file depicted in two dimensions for simplicity. The normal 17006 of the density point 17004 in the example intersects one or more edges between one or more pairs of voxels (e.g. see dark-shaded voxels) at density points 17010, 17012, 17013, 17014, and 17015 in the volumetric density file, for example. In some embodiments, the normal 17006 can intersect a voxel instead of an edge between two voxels, in which case the voxel itself is the density point. The density points 17010, 17012, 17013, 17014, and 17015 can have different density values from each other and from the density point 17004, for example. Because the density points provide density values at different positions, the computer-implemented method can use the relationship between density and position for a set of density points along the normal to determine the position along the normal of the maximum density derivative. If the maximum density derivative in the example is at density point 17010, then the initially generated digital surface point in the point cloud at the position of density point 17004 is moved in the point cloud to the position of density point 17010 by the computer-implemented method, for example. The new digital surface 17008 would then be the surface with the moved digital surface point.

Figure 21A:
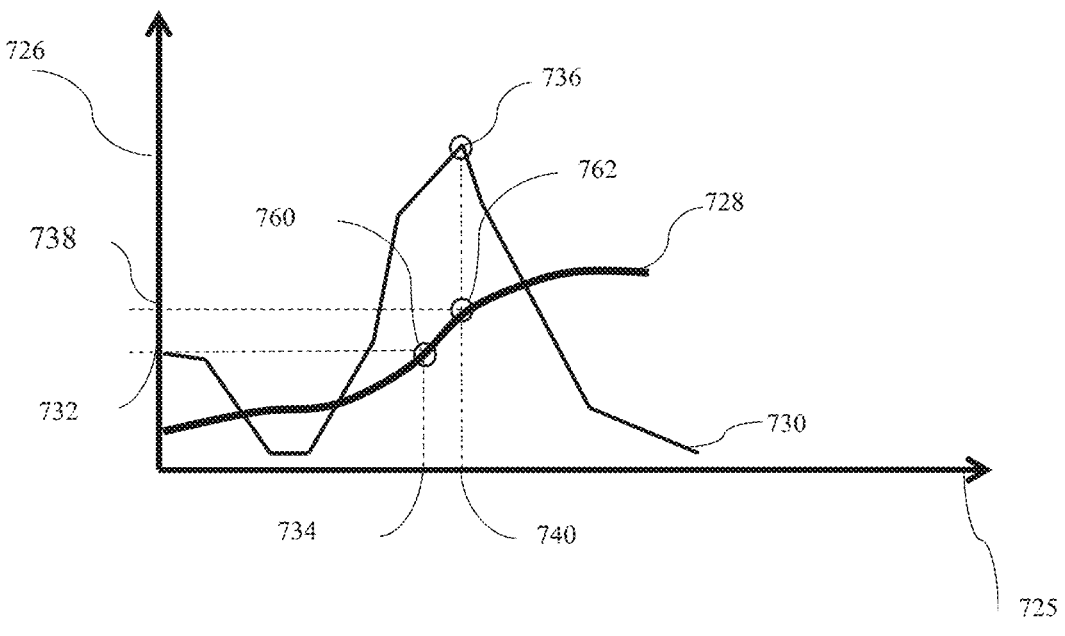
FIG. 21(*a*) is a graph of a density curve illustrating a relationship between the material density of voxels and their position along normal of a digital surface point.
Figure 21B:
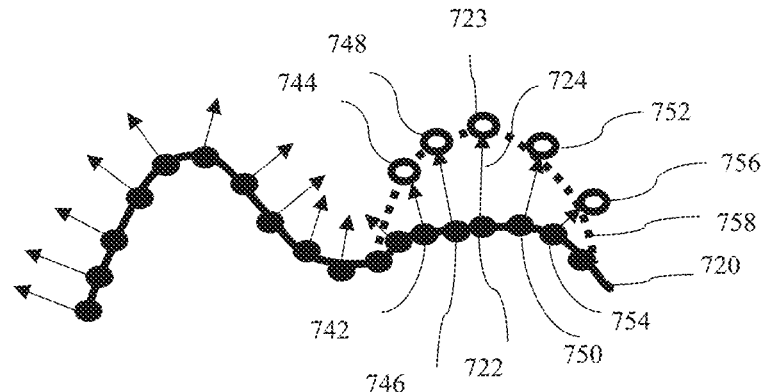

FIGS. 21(*a*) and 21(*b*) illustrate an example of moving a digital surface point to the maximum density derivative position. FIG. 21(*a*) illustrates an example of a density curve 728 showing a relationship between the material density of density points and their position along a normal of the density point 17004, which corresponds to a position of the digital surface point 722 and its normal 724 in the point cloud as shown in FIG. 21(*b*). The shape of density curve 728 in FIG. 21(*a*) can vary from scan to scan, and therefore the figure is only an illustrative example of one scan. In the figure, axis 725 represents positions along the normal of the digital surface point 722, and axis 726 represents density values of density points along the normal. Density derivative curve 730 illustrates the rate of change in the material density for positions along the normal of a density point.

In some embodiments the computer-implemented method calculates the density derivative curve 730 by taking a first derivative of the density curve 728. Some embodiments of the computer-implemented method can determine the first derivative of density curve 728 from at least two or more density points on the density curve 728 in a direction along the normal of the digital surface point 722. In some embodiments, the computer-implemented method can determine the first derivative of density curve 728 from up to 5 density points on the density curve 728, for example, in a direction along the normal of the digital surface point 722. When an iso-value of density 732 is initially set, the digital surface point 722 at the iso-value of density is located at iso-surface position 734, for example, based on point 760 of the density curve 728. The derivative density curve 730 for digital surface point 722 can indicate that its maximum density derivative 736 has a density value of 738 and is located at maximum density derivative position 740 based on point 762, for example. As shown in FIG. 21(*b*), the digital surface point 722 in the point cloud can be moved to its maximum density derivative position 740 as digital surface point 723 in the point cloud in some embodiments by the computer-implemented method.

In some embodiments, the computer-implemented method can, for example, first determine the density of density curve 728 $f(x,y,z)$ as a function of one argument only $f(x)=f(x,y=\text{fixed}, z=\text{fixed})$. Secondly, the computer-implemented method can find the derivative $f(x)$ of $f(x)$ approximating it by finite differences in all grid points, e.g. $f(x)=(f(x+dx)-f(x))/dx$, where $dx$ can in some embodiments represent a distance to the next density point. Thirdly, the computer-implemented method can find all local maxima of $f(x)$ for every y-fixed and z=fixed. The computer-implemented method can do this for up to and including 5 density points in some embodiments, for example. Fourthly, the computer-implemented method can repeat the second and third steps for $f(x,y,z)$ considered as a function of one arguments $f(y)=f(y,x=\text{fixed},z=\text{fixed})$ and $f(z)=f(z,x=\text{fixed}, y=\text{fixed})$.

Other digital surface points in the point cloud can also be moved to their maximum density derivative position in some embodiments by the computer-implemented method. For example, digital surface point 742 can be moved along its normal to its maximum density derivative position as digital surface point 744, digital surface point 746 can be moved along its normal to its maximum derivate density position as digital surface point 748, digital surface point 750 can be moved along its normal to its maximum derivate density position as digital surface point 752, and digital surface point 754 can be moved along its normal to its maximum derivate density position as digital surface point 756 by the computer-implemented method. Each of the digital surface points can have its own unique density curve reflecting density values for positions along its respective normal. Each of the digital surface points can therefore have its own unique density derivative curve as well as its own unique maximum density derivative value. This can be seen, for example, by the different final positions of digital surface points 744, 748, 740, 752, and 756 of the respective digital surface points based on their individual maximum density derivative value to form an optimized surface 758 that can be different from iso-surface 720.

In some embodiments of the computer-implemented method, every digital surface point is evaluated by the computer-implemented method and can be moved by the computer-implemented method based on its maximum density derivative value to generate the optimized surface 758. In some embodiments of the computer-implemented method, a subset of digital surface points is evaluated by the computer-implemented method and one or more digital surface points are moved by the computer-implemented method based on each of the subset's points' maximum density derivative value to generate the optimized surface 758. In some embodiments, one or more digital surface points may not be moved by the computer-implemented method and remain at their original position after evaluation with respect to their maximum density derivative value to generate the optimized surface 758. This can occur, for example, in some cases where the iso-value selected coincides with the maximum density derivative value of the digital surface point. In some embodiments, the computer-implemented method can move only those digital surface points not at their maximum density derivative.

As illustrated in the example of FIG. 21(*b*), one or more digital surface points on the selected digital surface can be placed by the computer-implemented method in virtual (or "digital") three dimensional space to a position of a maximum of density derivative along the one or more digital surface points' respective normal in some embodiments of the computer-implemented method. FIG. 21(*b*) illustrates an example of a cross-section of a selected digital iso-surface 720 at a particular iso-value of density. The digital iso-surface 720 includes one or more digital surface points such as digital surface point 722. Taken together, the digital surface points can define the digital iso-surface 720. The digital iso-surface 720 can also optionally include digital surface patches applied to fill holes or tunnels in the digital surface. Multiple digital surface points are shown along the curvature in FIG. 21(*b*), along with a normal for each digital surface point. For example, digital surface point 722 has a normal 724, which indicates the direction of gradient material density. In some embodiments the computer-implemented method can use the normal for each digital surface point to determine where to place digital surface points such as digital surface point 722 to satisfy a criteria of optimal digital surface selection such as, for example, a maximum density derivative, and generate an optimized surface.

In some embodiments, the computer-implemented method can as described and detailed in the present disclosure load a point cloud and for each point in the cloud, determine the point's normal, determine one or more density points along the normal in the volumetric density file as one or more intersection points between the point's normal and either voxels or voxel edges (i.e. between the voxels), determine a density curve from the density points, determine the maximum density derivative as disclosed herein, and move the digital surface point in the point cloud to the position of maximum density derivative along the normal of the digital surface point. The computer-implemented method can be repeated for each point in the point cloud, thereby generating an optimized digital surface.

In one embodiment of the computer-implemented method, the optimized surface 758 can optionally be displayed on a screen as a virtual three dimensional object image. The screen can be a computer or device display. This can allow, for example, a user to view the optimized surface 758 and perform additional operations. The user can also manipulate the 3D image of the optimized surface 758 by rotating, zooming the image, and performing other manipulations common to three dimensional virtual objects. In one embodiment of the computer-implemented method, the optimized surface 758 can be triangulated to generate a digital surface mesh.

Example Methods

Figure 22A:
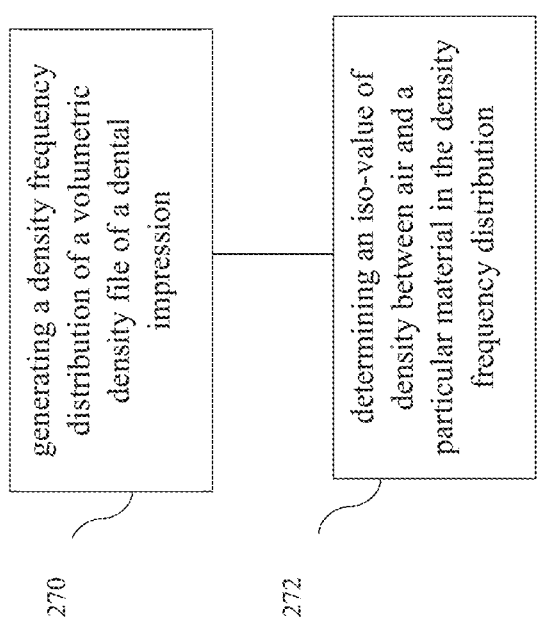
FIG. 22(*a*) is a flowchart illustrating a method of determining iso-value of density.

As illustrated in FIG. 22(*a*) disclosed is a computer-implemented method of determining a material surface from a volumetric density file. The computer-implemented method includes generating a density frequency distribution of a volumetric density file of a dental impression at 270 and determining an iso-value of density between air and a particular material in the density frequency distribution at 272. The particular material can be an impression material, for example, in some embodiments. The density frequency distribution can include voxel count peaks separated by valleys. Determining the iso-value of density can include selecting an iso-value of density value between a highest voxel count density range and a second highest voxel count density range. The highest voxel count density range can be an air density range and a second highest voxel count density range can be a particular material density range in some embodiments. The highest voxel count density range can be a particular material density range and a second highest voxel count density range can be an air density range in some embodiments. Determining the iso-value of density can include selecting an iso-value of density value between one or more density subranges of a highest voxel count peak and one or more density subranges of a second highest voxel count peak. The one or more density subranges including the highest voxel count peak can be an air density range and the one or more density subranges including a second highest voxel count peak can be a particular material density. The one or more density subranges including the highest voxel count peak can be a particular material density range and the one or more density subranges including second highest voxel count peak can be an air density. The dental impression can include Titanium and the computer-implemented method can provide an iso-value of density of the Titanium. Generating the density frequency distribution can further include detecting contaminants in the dental impression.

FIG. 22(*b*) illustrates a computer-implemented method of generating a digital model from a CT scan. An iso value of density is selected at 12004. One or more digital surface points in virtual 3D space for each of one or more voxels is generated at 12006. Each of the one or more digital surface points can optionally have a normal to an iso-surface at 12007. A subset of digital surface points from the plurality of digital surface points is selected at 12008 and triangulation of the subset of digital surface points can be optionally performed at 12010. Selecting a subset of digital surface points from the plurality of digital surface points at 12008 may optionally include selecting a desired level of distance between two or more of the subset of digital surface points at 12012, and/or selecting to a desired level based on curvature at 12014. Performing triangulation of the subset of points may optionally exclude one or more noisy regions at 12016. The computer-implemented method includes optionally either scanning a physical dental impression in a CT scanner to generate the volumetric density file at 12001, or receiving a digital volumetric density file comprising one or more voxels at 12002 in some embodiments. In some embodiments of the computer-implemented method, steps in the method may be performed in the order listed. In some embodiments, the method steps may be performed in any order. In some embodiments of the computer-implemented method, the desired level of distance can be a minimum distance between adjacent digital surface points.

Some embodiments of the computer-implemented method can include selecting a criteria of digital surface optimization on the subset of digital surface points and moving one or more digital surface points to satisfy the criteria of optimum digital surface selection at 12022. Some embodiments of the computer-implemented method optionally provide that the criteria of optimum digital surface selection includes a maximum of density derivative along a normal of each digital surface point of the digital surface points at 12020. In some embodiments, moving the one or more digital surface points can optionally include moving one or more digital surface points to the maximum density derivative at 12026.

Figure 23:
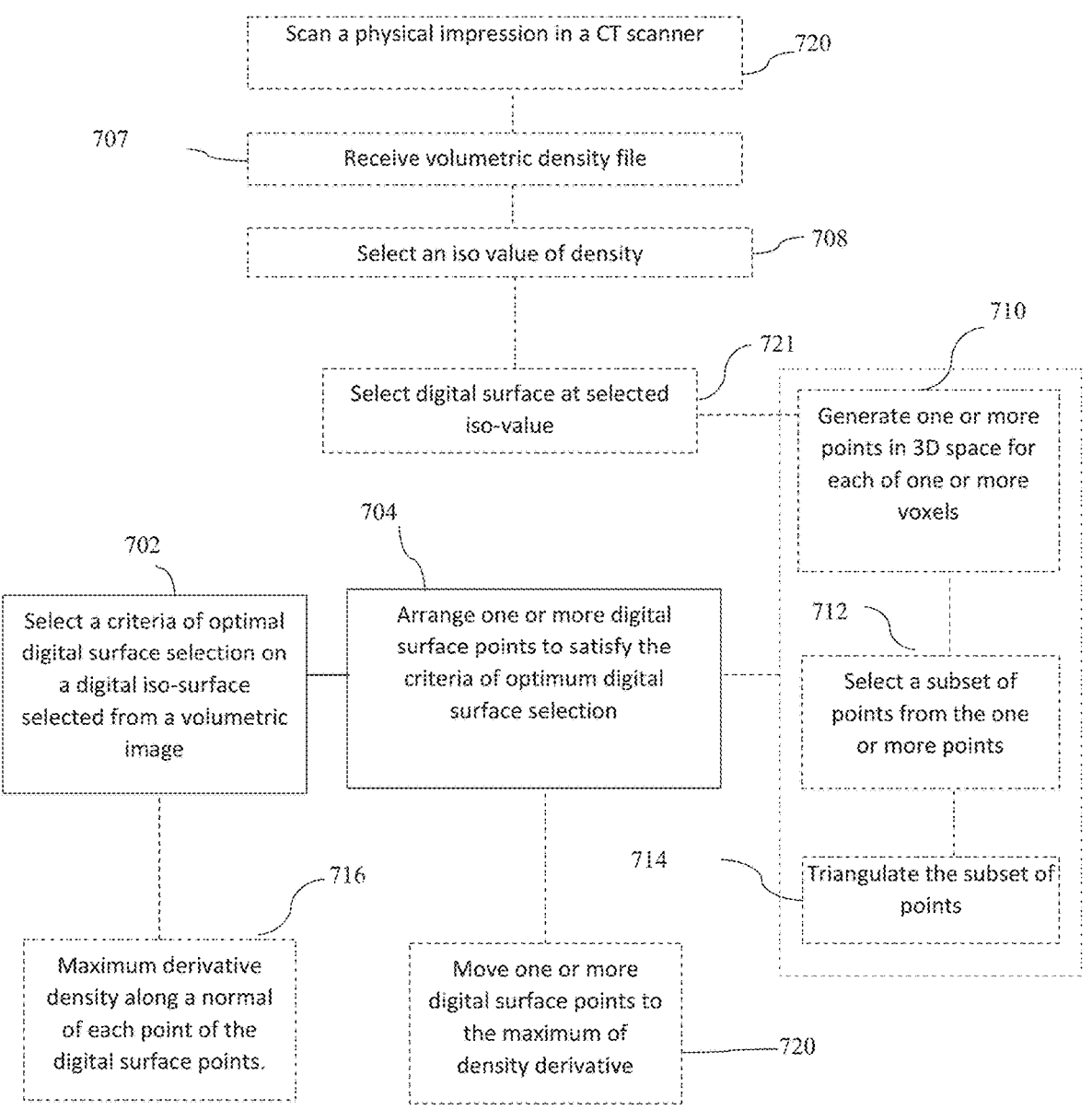
FIG. 23 illustrates a method of automatic high precision digital surface selection of a dental impression from CT scans.

In one embodiment a computer-implemented method of generating a digital model from a CT scan is disclosed as illustrated in FIG. 23. The computer-implemented method can include selecting a criteria of optimal digital surface selection on a digital iso-surface selected from a volumetric image at 702 and moving one or more digital surface points to satisfy the criteria of optimum digital surface selection at 704.

Some embodiments of the computer-implemented method optionally include generating one or more digital surface points in virtual 3D space for each of the digital surface points at 710. In one embodiment of the computer-implemented method, the digital iso-surface can optionally be selected from the volumetric image by receiving a digital volumetric density file including one or more voxels at 707, selecting an iso value of density at 708, selecting a digital surface at the selected iso-value at 721, generating one or more digital surface points in virtual 3D space for each of one or more voxels at 710, selecting a subset of digital surface points from the one or more digital surface points at 712, and performing triangulation on the subset of digital surface points at 714. In one embodiment of the computer-implemented method, the criteria of optimum digital surface selection optionally includes a maximum of density derivative along a normal of each digital surface point of the digital surface points at 716. In one embodiment of the computer-implemented method, moving the one or more digital surface points includes moving one or more digital surface points to the maximum density derivative. One embodiment of the computer-implemented method can include scanning a physical impression in a CT scanner at 720.

Some embodiments include a computer-implemented method of optimizing a digital surface, including receiving a digital surface having a plurality of digital surface points, selecting a criteria of digital surface optimization on the digital surface points and moving one or more digital surface points to satisfy the criteria of optimum digital surface selection. Some embodiments optionally include that the criteria of optimum digital surface selection includes a maximum of density derivative along a normal of each digital surface point of the digital surface points. Moving the one or more digital surface points can include moving one or more digital surface points to the maximum of density derivative.

One advantage of high precision surface selection from a CT scan as described in this disclosure can be certainty regarding surface position and improved accuracy regarding the surface position, shape, and topology, for example. Another advantage can be, for example, creating a surface with improved accuracy independently of the arbitrarily chosen iso-value.

Example System

Figure 24:
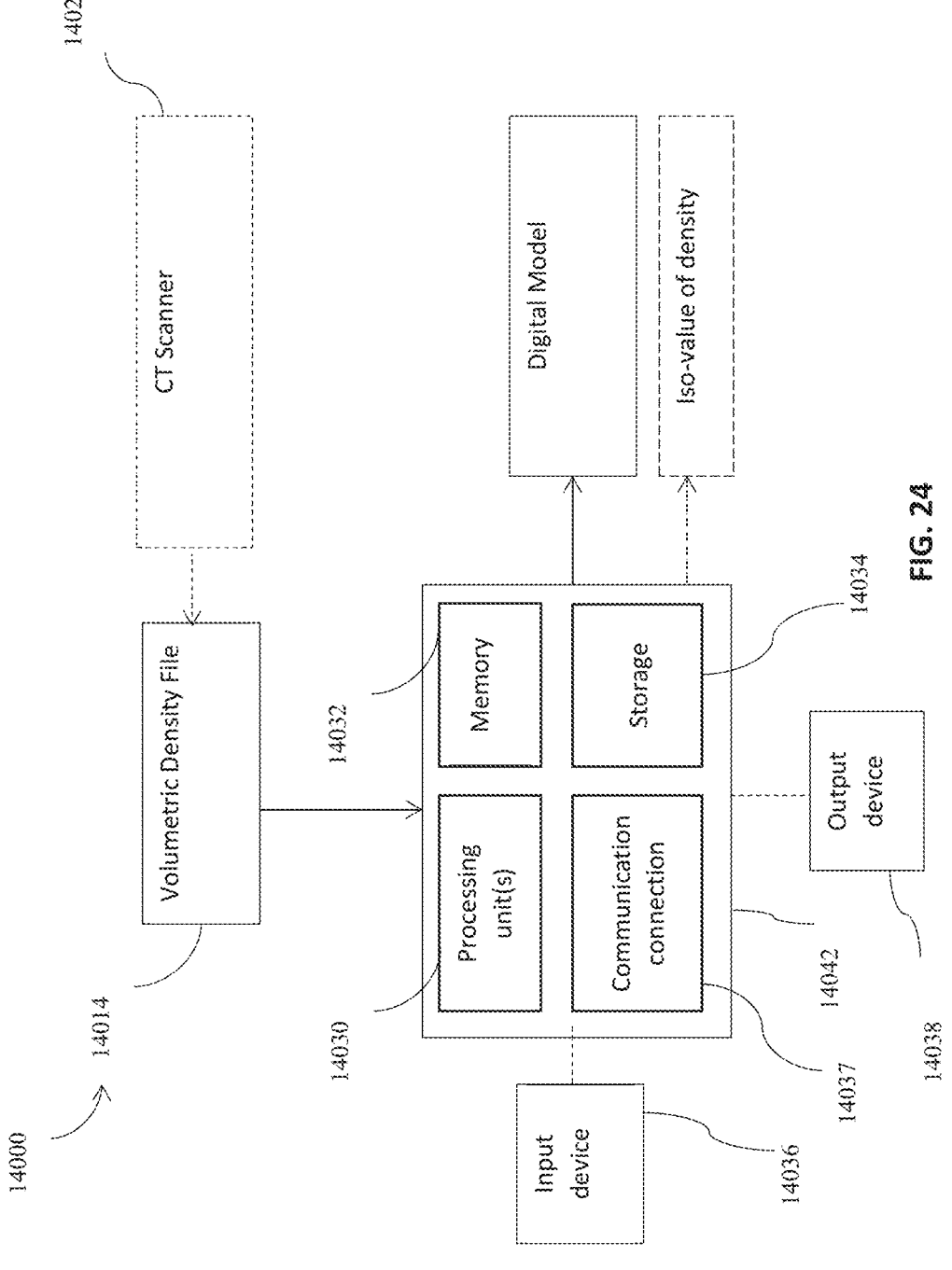
FIG. 24 is a diagram showing a system of one or more features in the present disclosure.

FIG. 24 illustrates a digital impression processing system 14000 in some embodiments. The system 14000 can include a processor 14030, computer-readable storage medium 14034 having instructions executable by the processor to perform steps including selecting an iso-value of density for a digital volumetric density file 14014 having one or more voxels, generating one or more digital surface points in virtual 3D space for each of one or more voxels, and selecting a subset of digital surface points from the one or more digital surface points. The volumetric density file 14014 can optionally be provided by an optional CT scanner 14028, for example.

In some embodiments, the instructions executable by the processor to perform steps further includes performing triangulation on the subset of digital surface points. In some embodiments, the selecting the subset of digital surface points from the plurality of digital surface points includes selecting a desired level of distance between two or more of the subset of digital surface points. In some embodiments, the minimum distance can be between 100 microns to 200 microns. In some embodiments, the selecting the subset of digital surface points from the plurality of digital surface points comprises selecting to a desired level based on curvature. In some embodiments, the selecting a subset of digital surface points from the one or more digital surface points comprises excluding one or more noisy regions. In some embodiments the instructions executable by the processor to perform steps further include scanning a physical dental impression in a CT scanner to generate volumetric density file. In some embodiments, the instructions executable by the processor to perform steps further comprising receiving the volumetric density file.

Some embodiments of the digital impression processing system 14000 can include optional features. For example, the system 14000 can include the instructions executable by the processor to perform steps that further include selecting a criteria of digital surface optimization on the subset of digital surface points and moving one or more digital surface points to satisfy the criteria of optimum digital surface selection. The criteria of optimum digital surface selection can include a maximum of density derivative along a normal of each digital surface point of the digital surface points. Moving the one or more digital surface points can include moving one or more digital surface points to the maximum density derivative.

Some embodiments include a non-transitory computer readable medium 14034 storing executable computer program instructions for creating a digital model from a CT scan of a physical dental impression is disclosed. The computer program instructions can include instructions for selecting an iso-value of density for a digital volumetric density file comprising one or more voxels, generating one or more digital surface points in virtual 3D space for each of one or more voxels and selecting a subset of digital surface points from the one or more digital surface points.

Some embodiments of the non-transitory computer readable medium 14034 can include optional features. For example, the non-transitory computer readable medium 14034 can include the instructions that further include selecting a criteria of digital surface optimization on the subset of digital surface points and moving one or more digital surface points to satisfy the criteria of optimum digital surface selection. The criteria of optimum digital surface selection can include a maximum of density derivative along a normal of each digital surface point of the digital surface points. Moving the one or more digital surface points can include moving one or more digital surface points to the maximum density derivative.

Also disclosed is a computer-implemented system of automatic detection of iso-value of density. FIG. 24 illustrates a digital impression processing system 14000 in some embodiments. The system 14000 can include a processor 14030, computer-readable storage medium 14034 having instructions executable by the processor to perform steps, including: generating a density frequency distribution of a volumetric density file of a dental impression and determining an iso-value of density between air and a particular material in the density frequency distribution. The particular material can be an impression material. The density frequency distribution can include voxel count peaks separated by valleys. Determining the iso-value of density can include selecting an iso-value of density value between a highest voxel count density range and a second highest voxel count density range. Determining the iso-value of density can include selecting an iso-value of density value between one or more density subranges of a highest voxel count peak and one or more density subranges of a second highest voxel count peak. The dental impression can include Titanium and the computer-implemented method can output an iso-value of density of the Titanium. Generating the density frequency distribution further can further include detecting contaminants in the dental impression.

Some embodiments include a non-transitory computer readable medium 14034 storing executable computer program instructions for automatic detection of iso-value of density. The computer program instructions can include instructions for generating a density frequency distribution of a volumetric density file of a dental impression and determining an iso-value of density between air and a particular material in the density frequency distribution. The particular material can be an impression material. The density frequency distribution can include voxel count peaks separated by valleys. Determining the iso-value of density can include selecting an iso-value of density value between a highest voxel count density range and a second highest voxel count density range. Determining the iso-value of density can include selecting an iso-value of density value between one or more density subranges of a highest voxel count peak and one or more density subranges of a second highest voxel count peak. The dental impression can include Titanium and the computer program instructions can output an iso-value of density of the Titanium. Generating the density frequency distribution further can further include detecting contaminants in the dental impression.

Some embodiments include a non-transitory computer readable medium storing executable computer program instructions for automatic detection of iso-value of density, the computer program instructions including instructions for: generating a density frequency distribution of a volumetric density file of a dental impression, and determining an iso-value of density between air and a particular material in the density frequency distribution. Some embodiments can include optional features. For example, the particular material can be an impression material. The density frequency distribution can include voxel count peaks separated by valleys. Determining the iso-value of density can include selecting an iso-value of density value between a highest voxel count density range and a second highest voxel count density range. Determining the iso-value of density can include selecting an iso-value of density value between one or more density subranges of a highest voxel count peak and one or more density subranges of a second highest voxel count peak. The dental impression can include Titanium and the computer-implemented method can output an iso-value of density of the Titanium. Generating the density frequency distribution further can further include detecting contaminants in the dental impression.

Also disclosed is a computer-implemented system of optimizing a digital surface, including a processor, a computer-readable storage medium comprising instructions executable by the processor to perform steps comprising: receiving a digital surface comprising a plurality of digital surface points, selecting a criteria of digital surface optimization on the digital surface points, and moving one or more digital surface points to satisfy the criteria of optimum digital surface selection. Moving the one or more digital surface points can include moving one or more digital surface points to the maximum of density derivative.

Also disclosed is a non-transitory computer readable medium storing executable computer program instructions for optimizing a digital surface, the computer program instructions comprising instructions for: receiving a digital surface comprising a plurality of digital surface points, selecting a criteria of digital surface optimization on the digital surface points, and moving one or more digital surface points to satisfy the criteria of optimum digital surface selection. Moving the one or more digital surface points can include moving one or more digital surface points to the maximum of density derivative.

One advantage of one or more features in embodiments, method(s), and system(s) of the present disclosure can include, for example, improved creation of an improved digital model of a physical impression with an improved digital surface that more accurately represents the physical attributes of the physical impression than digital models generated by conventional techniques.

As an example, in some embodiments, selecting an iso-value of density for a digital volumetric density file comprising one or more voxels, generating one or more digital surface points in virtual 3D space for each of one or more voxels, and selecting a subset of digital surface points from the one or more digital surface points can avoid and/or reduce subsequent digital surface mesh simplification and smoothing and generate a digital surface mesh with fewer degenerate triangles than conventional techniques, thereby improving the digital surface accuracy.

As another example, optional features such as performing triangulation on the subset of digital surface points, selecting a desired level of distance between two or more of the subset of digital surface points, selecting to a desired level based on curvature, and/or excluding one or more noisy regions can also provide an improved digital surface and a digital surface mesh with fewer degenerate triangles over conventional techniques.

As another example, optional features such as selecting a criteria of digital surface optimization on the subset of digital surface points and moving one or more digital surface points to satisfy the criteria of optimum digital surface selection, the criteria of optimum digital surface selection including a maximum of density derivative along a normal of each digital surface point of the digital surface points, and/or moving the one or more digital surface points includes moving one or more digital surface points to the maximum density derivative can improve the accuracy of the desired digital surface position, shape, and topology over conventional technology. Another advantage can be, for example, generating a hole-patched surface with a more accurate topology.

Similarly, as an example, a digital impression processing system that includes a processor and a computer-readable storage medium including instructions executable by the processor to perform any of the features in this disclosure can also provide an improved and more accurate digital surface and digital surface mesh with fewer degenerate triangles over conventional techniques as discussed in the disclosure.

Another advantage of one or more features of the present disclosure can include, for example, an improved digital model generation time. For example, whereas conventional techniques can take up to and including 10 minutes to generate a digital model from a physical impression, one or more features in the present disclosure can reduce the time to generate the digital model to 15 seconds due to the improved digital processing of the physical impression.

One advantage of one or more features of the present disclosure can include, for example, accurate surface representation independent of the iso-selected value and regardless of the thinness of the physical impression scanned.

One or more of the features disclosed herein can be performed and/or attained automatically, without manual or user intervention. One or more of the features disclosed herein are performed by a computer-implemented method. The features-including but not limited to any methods and systems-disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure. Rather, the scope of the invention is defined by all that comes within the scope and spirit of the following claims.

What is claimed is:

1. A computer-implemented method of determining a material surface from a volumetric density file, comprising:
   receiving a volumetric density file of a CT scanned dental impression;
   selecting an iso-value of density for the volumetric density file to provide one or more voxels;
   generating one or more digital surface points in a 3D point cloud for each of one or more voxels;
   selecting a subset of digital surface points from the one or more digital surface points to provide a reduced 3D point cloud;
   selecting a criteria of digital surface optimization on the subset of digital surface points;
   moving one or more digital surface points to satisfy the criteria of optimum digital surface selection; and
   generating a digital surface mesh for the reduced 3D point cloud.

2. The method of claim 1, further comprising generating a density frequency distribution of the volumetric density file.

3. The method of claim 2, wherein generating the density frequency distribution further comprises detecting contaminants in the dental impression.

4. The method of claim 1, wherein the criteria of optimum digital surface selection comprises a maximum of density derivative along a normal of each digital surface point of the digital surface points.

5. The method of claim 1, wherein moving the one or more digital surface points comprises moving one or more digital surface points to the maximum of density derivative.

6. A digital impression processing system for creating a digital model from a CT scan of a physical dental impression, comprising:

a processor;

a computer-readable storage medium comprising instructions executable by the processor to perform steps comprising:

receiving a volumetric density file of a CT scanned dental impression;

selecting an iso-value of density for the volumetric density file to provide one or more voxels;

generating one or more digital surface points in a 3D point cloud for each of one or more voxels;

selecting a subset of digital surface points from the one or more digital surface points to provide a reduced 3D point cloud;

selecting a criteria of digital surface optimization on the subset of digital surface points;

moving one or more digital surface points to satisfy the criteria of optimum digital surface selection; and generating a digital surface mesh for the reduced 3D point cloud.

7. The system of claim 6, further comprising generating a density frequency distribution of the volumetric density file.

8. The system of claim 7, wherein generating the density frequency distribution further comprises detecting contaminants in the dental impression.

9. The system of claim 6, wherein the criteria of optimum digital surface selection comprises a maximum of density derivative along a normal of each digital surface point of the digital surface points.

10. The system of claim 6, wherein moving the one or more digital surface points comprises moving one or more digital surface points to the maximum of density derivative.

11. A non-transitory computer readable medium storing executable computer program instructions for creating a digital model from a CT scan of a physical dental impression, the computer program instructions comprising instructions for:

receiving a volumetric density file of a CT scanned dental impression;

selecting an iso-value of density for the volumetric density file to provide one or more voxels;

generating one or more digital surface points in a 3D point cloud for each of one or more voxels;

selecting a subset of digital surface points from the one or more digital surface points to provide a reduced 3D point cloud;

selecting a criteria of digital surface optimization on the subset of digital surface points;

moving one or more digital surface points to satisfy the criteria of optimum digital surface selection; and generating a digital surface mesh for the reduced 3D point cloud.

12. The medium of claim 11, further comprising generating a density frequency distribution of the volumetric density file.

13. The medium of claim 12, wherein generating the density frequency distribution further comprises detecting contaminants in the dental impression.

14. The medium of claim 11, wherein the criteria of optimum digital surface selection comprises a maximum of density derivative along a normal of each digital surface point of the digital surface points.

15. The medium of claim 11, wherein moving the one or more digital surface points comprises moving one or more digital surface points to the maximum of density derivative.

* * * * *